(12) United States Patent
Anderson

(10) Patent No.: US 11,191,680 B2
(45) Date of Patent: Dec. 7, 2021

(54) APPARATUS AND METHODS FOR ADHESION

(71) Applicant: MicroKoll Inc., San Diego, CA (US)

(72) Inventor: Steven Craig Anderson, Lompoc, CA (US)

(73) Assignee: Microkoll, Inc., San Diego, CA (US)

( * ) Notice: Subject to any disclaimer, the term of this patent is extended or adjusted under 35 U.S.C. 154(b) by 288 days.

(21) Appl. No.: 16/169,150

(22) Filed: Oct. 24, 2018

(65) Prior Publication Data
US 2019/0053961 A1 Feb. 21, 2019

Related U.S. Application Data

(63) Continuation of application No. 15/156,893, filed on May 17, 2016, now Pat. No. 10,149,789, which is a
(Continued)

(51) Int. Cl.
*A61F 13/62* (2006.01)
*A44B 18/00* (2006.01)
(Continued)

(52) U.S. Cl.
CPC ........ *A61F 15/006* (2013.01); *A44B 18/0049* (2013.01); *A44B 18/0061* (2013.01);
(Continued)

(58) Field of Classification Search
CPC .. A61F 15/006; A61F 13/625; A44B 18/0096; A44B 18/0061; Y10T 428/24017
See application file for complete search history.

(56) References Cited

U.S. PATENT DOCUMENTS

| | | | | |
|---|---|---|---|---|
| 6,086,599 A | * | 7/2000 | Lee | A61B 17/12022 606/108 |
| 6,224,807 B1 | * | 5/2001 | Clune | B23H 9/006 219/69.17 |

(Continued)

*Primary Examiner* — Jacob J Cigna
*Assistant Examiner* — Michael W Hotchkiss
(74) *Attorney, Agent, or Firm* — Felix L. Fischer

(57) ABSTRACT

A material engagement element sheet formed from a sheet material (10) incorporates a pattern of material engagement element slots (14), each slot containing an array of material engagement elements (20) which have a tapered distal section (30), a flange section (34) and a proximal section (32) which is attached to an edge of the slots in the sheet material. The material engagement element sheet material may be a single layer of shape memory material, or the sheet material may be a composite of different layers some of which may include pre-strained shape memory materials with distinguishable activation parameters. The material engagement element slot configuration allows for the simultaneous processing of the material engagement elements. The material engagement elements may be processed such that they are in a state that is substantially perpendicular to the surface of the material engagement element sheet. The configuration of the flexible base material and the pattern of the material engagement element slots may be used in order to manufacture various material engagement element devices including a material engagement element pad device (166), a cylindrical material engagement element device (104, 105), and a spherical material engagement element device (152).

20 Claims, 53 Drawing Sheets

Related U.S. Application Data continuation of application No. 14/240,668, filed as application No. PCT/US2012/052307 on Aug. 24, 2012, now Pat. No. 9,364,052.

(60) Provisional application No. 61/527,560, filed on Aug. 25, 2011.

(51) Int. Cl.
| | | |
|---|---|---|
| *C22F 1/00* | (2006.01) | |
| *A61F 15/00* | (2006.01) | |
| *A61F 13/02* | (2006.01) | |
| *A61B 17/00* | (2006.01) | |
| *A61F 13/00* | (2006.01) | |

(52) U.S. Cl.
CPC ........ *A61F 13/025* (2013.01); *A61F 13/0253* (2013.01); *A61F 13/0269* (2013.01); *A61F 13/625* (2013.01); *C22F 1/006* (2013.01); *A61B 2017/00969* (2013.01); *A61F 2013/00425* (2013.01); *Y10T 428/24017* (2015.01)

(56) References Cited

U.S. PATENT DOCUMENTS

| | | | | |
|---|---|---|---|---|
| 6,546,602 B1* | 4/2003 | Eipper | ............... | A44B 18/0003 24/304 |
| 7,020,938 B2* | 4/2006 | Ottaviani | ........... | A44B 18/0003 188/267 |
| 7,052,636 B2* | 5/2006 | Ausen | ................ | A44B 18/0049 264/145 |
| 7,067,185 B2* | 6/2006 | Ausen | ................ | A44B 18/0049 428/100 |
| 7,146,690 B2* | 12/2006 | Stanford, Jr. | ...... | A44B 18/0003 24/451 |
| 7,200,902 B2* | 4/2007 | Browne | ............. | A44B 18/0003 24/442 |
| 7,308,738 B2* | 12/2007 | Barvosa-Carter | ........................... | A44B 18/0003 24/442 |
| 7,478,460 B2* | 1/2009 | Gallant | ............... | A44B 13/0023 24/306 |
| 8,906,046 B2* | 12/2014 | Anderson | ............. | A61B 17/08 606/151 |
| 2002/0125605 A1* | 9/2002 | Lacey | ................ | A44B 18/0049 264/167 |
| 2004/0033336 A1* | 2/2004 | Schulte | .............. | A44B 18/0096 428/100 |
| 2005/0118388 A1* | 6/2005 | Kingsford | ......... | A61M 37/0015 428/99 |
| 2005/0246873 A1* | 11/2005 | Tachauer | ................ | B29C 43/46 24/451 |
| 2009/0208698 A1* | 8/2009 | Langen | .............. | A44B 18/0003 428/100 |
| 2011/0265292 A1* | 11/2011 | Kirby | ................ | A44B 18/0096 24/451 |
| 2015/0327634 A1* | 11/2015 | Kirby | ................ | A44B 18/0053 24/452 |

\* cited by examiner

APPARATUS AND METHODS FOR ADHESION

RELATED APPLICATIONS

This patent application is a continuation of U.S. patent application Ser. No. 15/156,893 which is a continuation of U.S. patent application Ser. No. 14/240,668 which is a US national filing of PCT application serial no. PCT/US12/52307 filed on Aug. 24, 2012 claiming priority of U.S. Provisional Patent Application Ser. No. 61/527,560 filed on Aug. 25, 2011, and is with U.S. patent application Ser. No. 15/601,187 filed on May 22, 2017 having a common assignee with the present application, the disclosures of which are incorporated herein by reference.

SUMMARY

A material engagement element sheet formed from a sheet material incorporates a pattern of material engagement element slots, each slot containing an array of material engagement elements which have a tapered distal section, a flange section and a proximal section which is attached to an edge of the slots in the sheet material. The material engagement element sheet material may be a single layer of shape memory material, or the sheet material may be a composite of different layers some of which may include pre-strained shape memory materials with distinguishable activation parameters. The material engagement element slot configuration allows for the simultaneous processing of the material engagement elements. The material engagement elements may be processed such that they are in a state that is substantially perpendicular to the surface of the material engagement element sheet. The distal sections of the material engagement elements may then be inserted into a temporary stabilizing material; the temporary stabilizing material prevents the premature deployment of the material engagement elements and maintains the position of each tissue engagement relative to the surrounding tissue engagement elements. The proximal sections of the tissue engagement elements may then be suitably encapsulated in a flexible base material. The configuration of the flexible base material and the pattern of the material engagement element slots may be used in order to manufacture various material engagement element devices including a material engagement element pad device, a cylindrical material engagement element device, and a spherical material engagement element device.

DETAILED DESCRIPTION

Figure 1A:
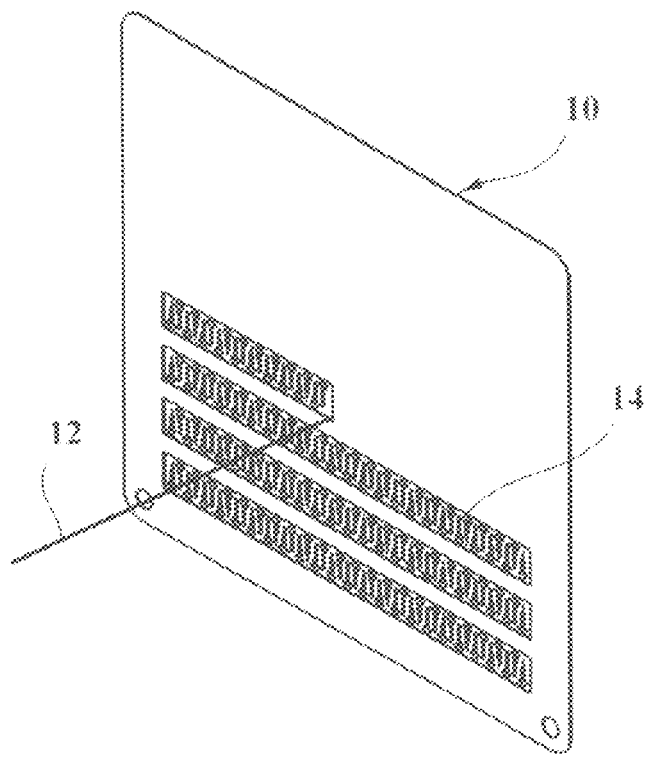
FIG. 1A is a perspective view of a material engagement element sheet embodiment being produced from sheet material.

Example embodiments described herein are directed to an array of engagement elements. Such engagement elements may be produced such that they are arranged within a substantially flat sheet of material, thus creating an engagement element patterned sheet. The sheet material may be comprised of a single layer of shape memory alloy or shape memory polymer, multiple layers of shape memory alloys and/or shape memory polymers with distinguishable activation parameters, or any other suitable material or materials. The engagement elements may be subsequently processed and configured such that they are substantially perpendicular to the surface of the engagement element patterned sheet. The engagement element patterned sheet can then be processed such that the distal and proximal ends of the engagement elements are contained within two separate sections of material or materials, a temporary stabilizing material and a flexible base material respectively. For some embodiments, this process may be a two step mold process. The temporary stabilizing material which incorporates the distal ends of the engagement elements can then be removed prior to the deployment and/or activation of the engagement device. The flexible base material which incorporates the proximal ends of the engagement elements remains with the given apparatus. The pattern of the substantially flat engagement element array may be suitably configured for any engagement device configuration. Therefore, this process may be used in order to create a variety of apparatus, including a flat pad, a cylindrically symmetric tube, a cylindrically symmetric balloon, a spherically symmetric balloon, as well as other configurations of engagement devices. An embodiment of an engagement element configuration wherein the engagement element lies in close proximity to the surface of the flexible base material prior to the deployment of the engagement device is disclosed herein. Embodiments of engagement devices wherein the flexible base material is comprised of skin graft material are disclosed herein. Embodiments wherein a suitable configuration of engagement elements and flexible base material are applied as an adhesive to the surface of a conventional bandage are disclosed herein.

Some embodiments herein describe methods by which the device embodiments described in U.S. application Ser. No. 13/583,199, and U.S. application Ser. No. 13/119,540, now U.S. Pat. No. 8,906,046, may be manufactured. The nomenclature engagement elements used within this document refers to embodiments that can have the same features, dimensions, and materials as embodiments in the documents incorporated by reference referred to as the following: microposts, shape memory microposts, tissue engagement members, tissue engagement elements, shape memory engagement elements, and tissue capture elements. The nomenclature flexible base material used in this document refers to embodiments that can have with the same features, dimensions, and materials as embodiments in the documents incorporated by reference referred to as the following: flexible material and substrate material. The methods discussed herein may be used to manufacture any suitable configuration of engagement devices including an material engagement element pad 78 as shown in FIG. 6D, cylindrical material engagement element devices 104 and 105 as shown in FIGS. 7P and 7Q respectively, a spherical material engagement element device 152 as shown in FIG. 9T, or any other suitable material engagement element device configuration. For some indications which may or may not include medical applications, it can be desirable to scale the engagement elements up such that any suitable devices which incorporate them may be used for purposes of adhesion. The process of adhesion through the use of deployment and activation of engagement elements may also have applications in industry wherein any penetrable material such as rubber, silicone, foam, gauze, or any other suitable material may be adhered to with the use of this technology.

Figure 7A:
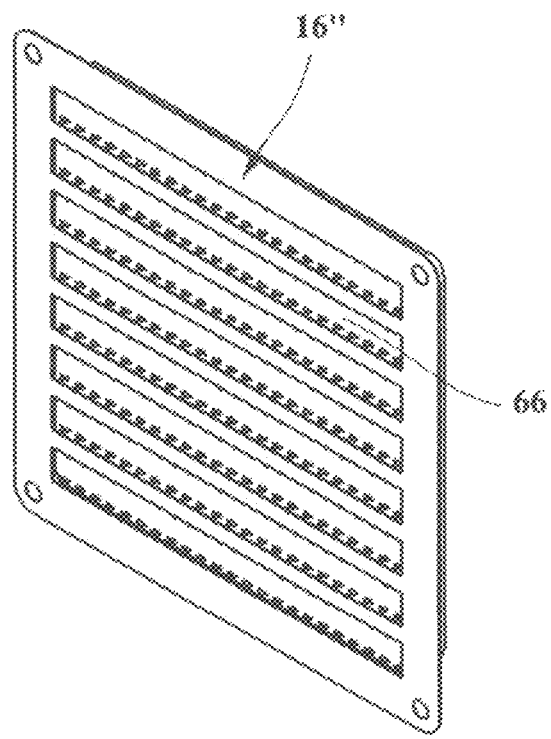
FIG. 7A is a perspective view of an assembly of a material engagement element sheet with the elements in a perpendicular state partially deployed into a temporary stabilizing material.

In PCT/US09/57348 FIG. 7A and paragraph 69 describe a pad comprised of flexible base material and an array of engagement elements, a configuration which will hereto be referred to as a material engagement element pad. The methods discussed herein detail the manufacture of a material engagement element pad. FIG. 1A shows sheet material 10 with a pattern of material engagement element slots 14 being cut into the sheet material 10 by a laser beam 12. The sheet material 10 may be comprised of any suitable single layer of material or any suitable combination of multiple layers of suitable materials. For example the sheet material 10 may be comprised of a single layer of shape memory alloy material or a single layer of shape memory polymer material. It may also be desirable for the sheet material 10 to be comprised of multiple layers of any suitable materials that have been suitably processed. For example, the shape memory polymer composite sheet capable of multiple deflections as described in PCT/US11/02802 FIGS. 7A-7E and paragraph 34. The shape memory materials described in this document may be activated by any of the following activation methods: thermal activation, activation by the application of ultra violet (UV) radiation, activation by surrounding medium PH change, activation by the application of a magnetic field, activation by the application of electric current, activation by the application of radio frequency (RF) energy, or any other suitable shape memory material activation method.

Figure 1B:
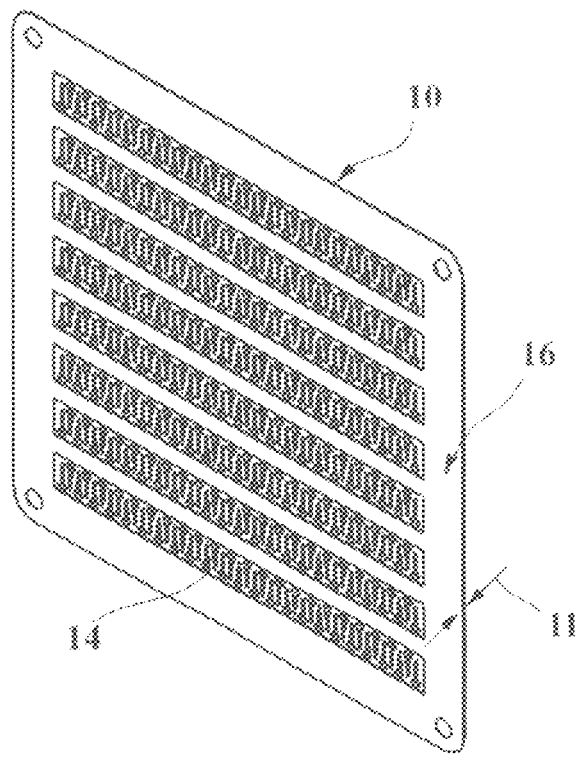
FIG. 1B is a perspective view of a completed material engagement element sheet embodiment.
Figure 1C:
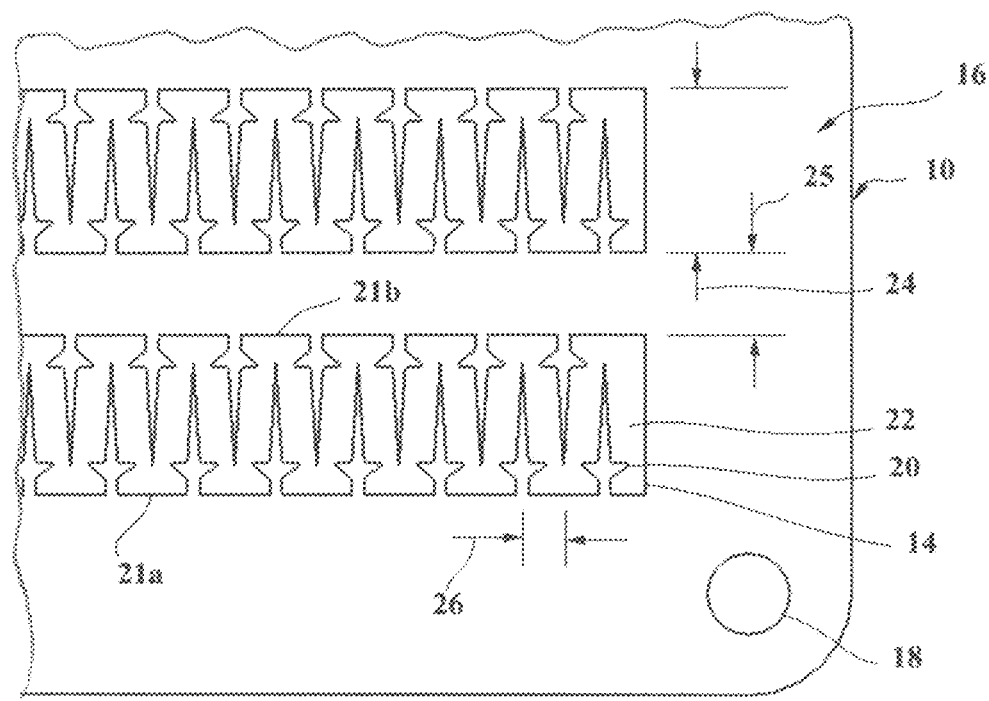
FIG. 1C is an enlarged view of a portion of the material engagement element sheet of FIG. 1B showing the material engagement elements and the material engagement element slots.

FIG. 1B is a perspective view of a completed material engagement element sheet 16 after the cutting process. The material engagement element sheet 16 is comprised of the sheet material 10 and the material engagement element slots 14. The method to cut the material engagement element slots 14 for the described embodiments is laser cutting; however any of the following methods could also be used: waterjet cutting, microstamping, nanostamping, chemical etching, or photochemical etching. Dimension 11, the thickness of the sheet material 10 is also shown in FIG. 1B. FIG. 1C is a close up view of the front surface of the material engagement element sheet 16 which provides a detailed view of the material engagement element slots 14. Material engagement elements 20 extend from the sides 21a, 21b of the material engagement element slots 14 with a gap 22 between the sheet material 10 and the material engagement elements 20. A material engagement element sheet location hole 18 is provided for alignment of the material engagement element sheet 16 during processing. Also shown in FIG. 1C are the following dimensions: dimension 24 is the width dimension W of the material engagement element slot 14, dimension 25 is the width dimension of the sheet material 10 between the material engagement element slots 14, and dimension 26 is the distance between subsequent material engagement elements 20 contained within the material engagement element slots 14. Dimension 11 the thickness of the sheet material 10 is hereto labeled with the parameter t. The parameter t will be used in order to set ranges on the other dimensions. The thickness t (dimension 11) of the sheet material 10 can vary from 1 micron to 1 millimeter. Dimension 24 the width dimension of the material engagement element slot 14 can range from 10*t to 100*t. Once dimension 24 is chosen, dimension 25 can range from 1/10*(dimension 24) to 2*(dimension 24). The distance between subsequent material engagement elements can range from 1/10*(dimension 24) to 2*(dimension 24).

Figure 1D:
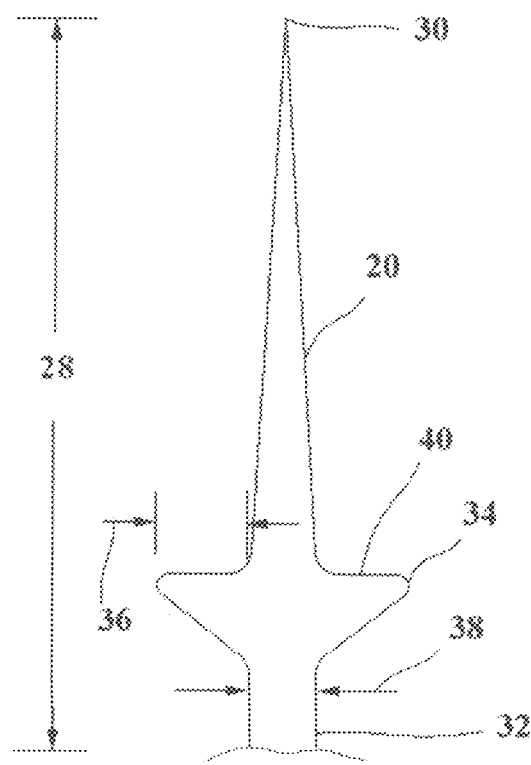
FIG. 1D shows the profile of a material engagement element embodiment that is attached to a material engagement element sheet.

The gap 22 between the sheet material 10 and the material engagement elements 20 and the fact that the material engagement elements 20 remain attached to the sheet material 10 after the cutting process are two significant improvements to this embodiment over previous embodiments of material engagement elements cut from sheet material. As an example, consider the material engagement elements shown in FIG. 9A of PCT/US11/02802; each material engagement element is cut from the sheet material and then has to be individually processed: fixed into the flexible base material and then molded. For the embodiment currently being described, as shown in FIG. 1C, each material engagement element 20 remains attached to the sheet material 10 after the cutting process and the gap 22 isolates each material engagement element 20 from the surrounding sheet material 10. Because the material engagement elements 20 remain attached to the sheet material 10 and are isolated from the sheet material 10 by the gap 22, all of the material engagement elements 20 attached to the material engagement element sheet 16 may be processed simultaneously as opposed to individually. FIG. 1D depicts the profile of a typical material engagement element embodiment 20. The material engagement element 20 tapers to a distal end 30 which provides a sharpened tissue penetrating tip. Dimension 28 is the length of the material engagement element 20. Dimension 28 can range from ½ *(dimension 24) to 1*(dimension 24) where dimension 24 is the dimension of the width W of the material engagement element slot 14. The material engagement element 20 includes two flanges 34, the dimensions of which are represented by dimension 36. Dimension 36 may be 1 to 2× the dimension 38 of the width of the base of the material engagement element 20. Dimension 38 can range from 4*t to 10*t where t is the thickness of the sheet material 10. The flange 34 incorporates flat surface 40, which when potted into the flexible base material 76, prevents the material engagement element 20 from tearing out of the flexible base material 76.

For some embodiments of the sheet material 10 it may be desirable to set an engagement shape into the material engagement elements 20. The material engagement elements 20 can then be flattened in order to continue with processing. The shape setting/flattening process would not be necessary for sheet material 10 embodiments that rely on pre-strained sheets in order to achieve an engagement state; as an example of the pre-strained sheet deflection process see PCT/US11/02802 FIGS. 7A-7E and paragraph 34. Sheet material 10 embodiments that might require the shape setting/flattening process would include a single layer of shape memory alloy such as Nitinol. In this case an "engagement" shape may be set into the Nitonol material with the application of an appropriate thermal cycle. For example, the sheet material 10 may be confined to the desired engagement shape and then heated to a given temperature (e.g. 500° C.) for a given duration (e.g. 10 minutes). This process will set the engagement shape into the shape memory alloy material. When the material is below its transition temperature (Af temperature) it is malleable (Martensite phase) and when it above its transition temperature (Austenite phase) it reverts to the engagement shape. For the case of the material engagement element sheet 16 with sheet material 10 comprised of a single layer of shape memory alloy, it may be desirable to shape set radii into the material engagement elements 20. The shape set radius is the means by which a shape memory alloy material engagement element 20 may assume an engagement state and capture tissue once it is deployed as shown in PCT/US09/57348 FIGS. 2A-2D.

Figure 2A:
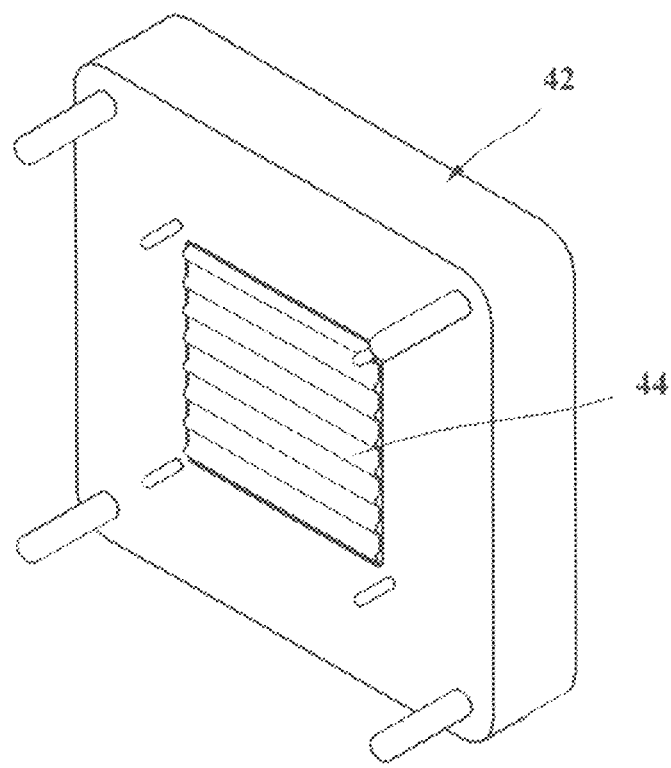
FIG. 2A shows a perspective view of a bottom radius fixture.
Figure 2B:
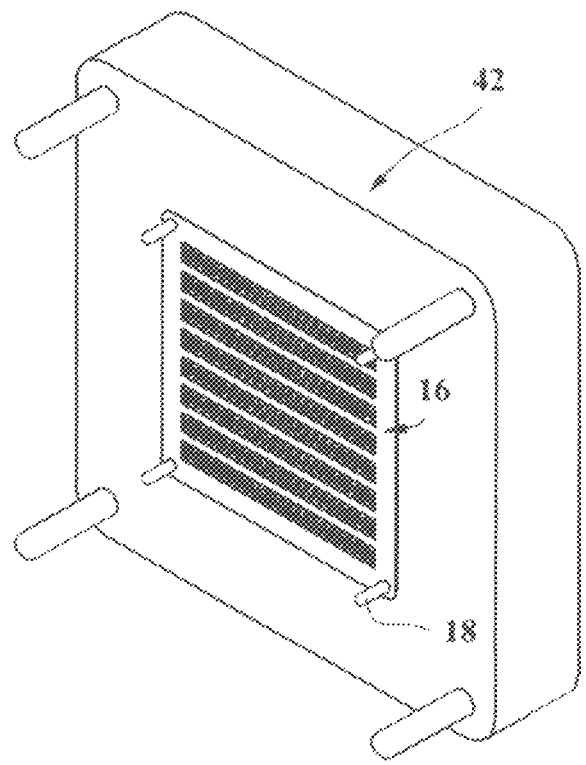
FIG. 2B shows a perspective view of the bottom radius fixture of FIG. 2A with a material engagement element sheet loaded onto it.
Figure 2C:
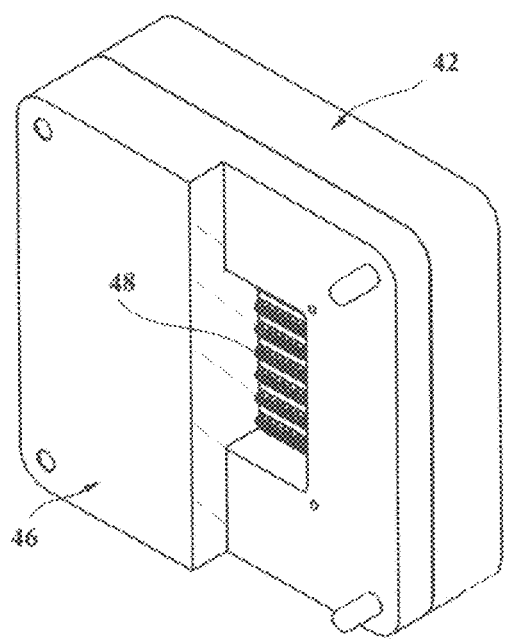
FIG. 2C is a perspective view of a top radius fixture which is shown in section view, the bottom radius fixture of FIG. 2A, and the engagement element patterned sheet.
Figure 2D:
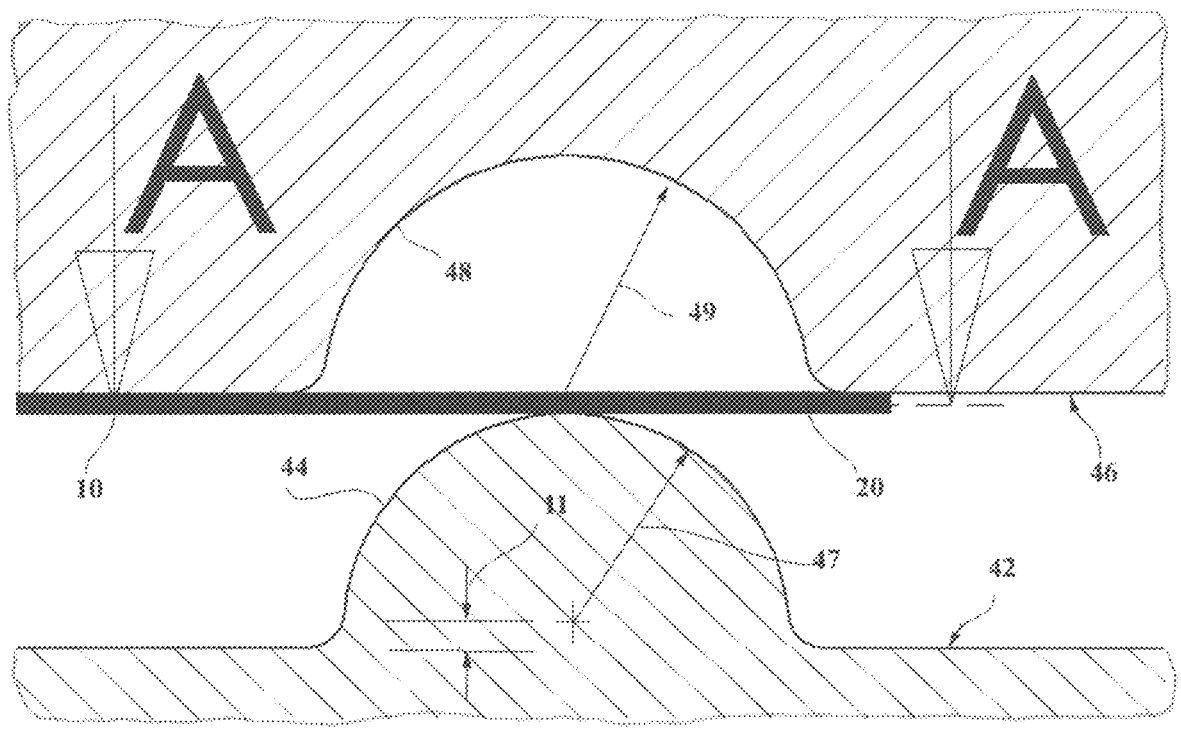
FIGS. 2D-2G show a section of the top radius fixture and bottom radius fixture being forced together in order to shape an engagement element.
Figure 2E:
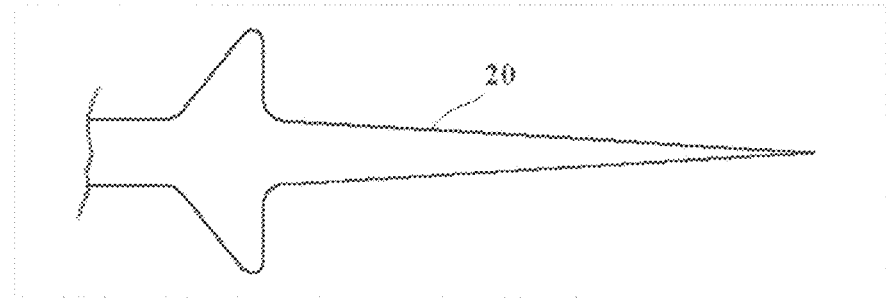
Figure 2F:
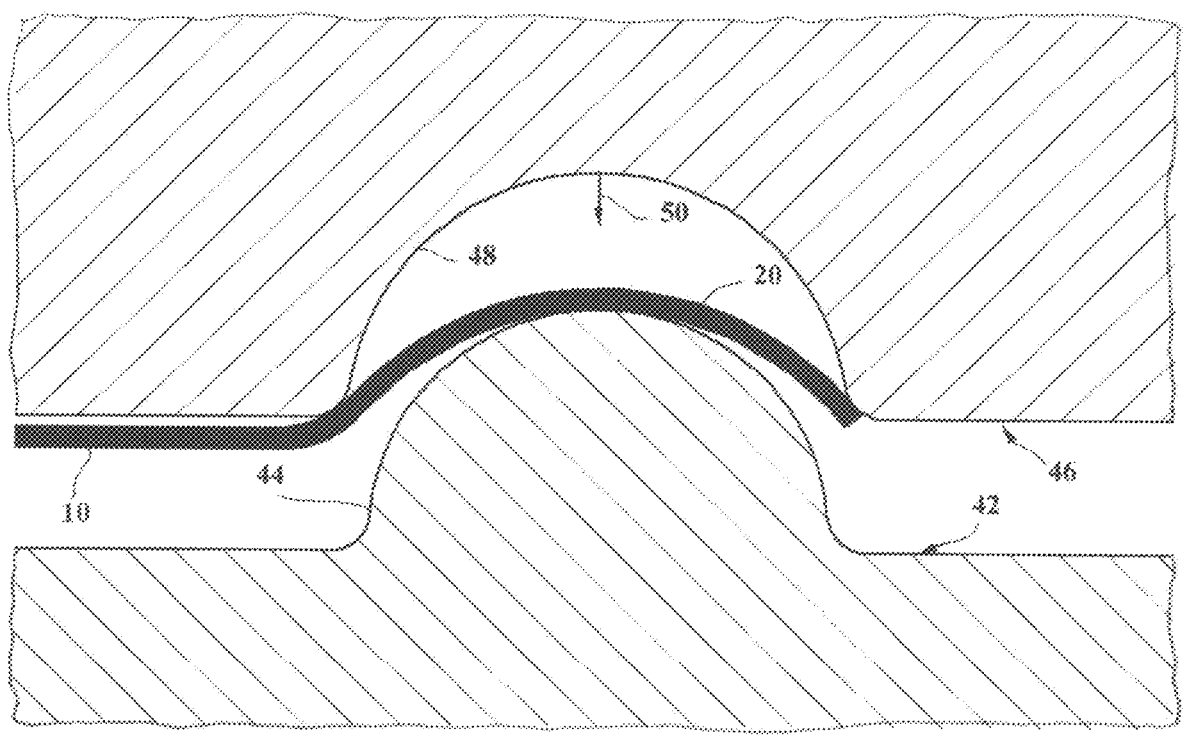
Figure 2G:
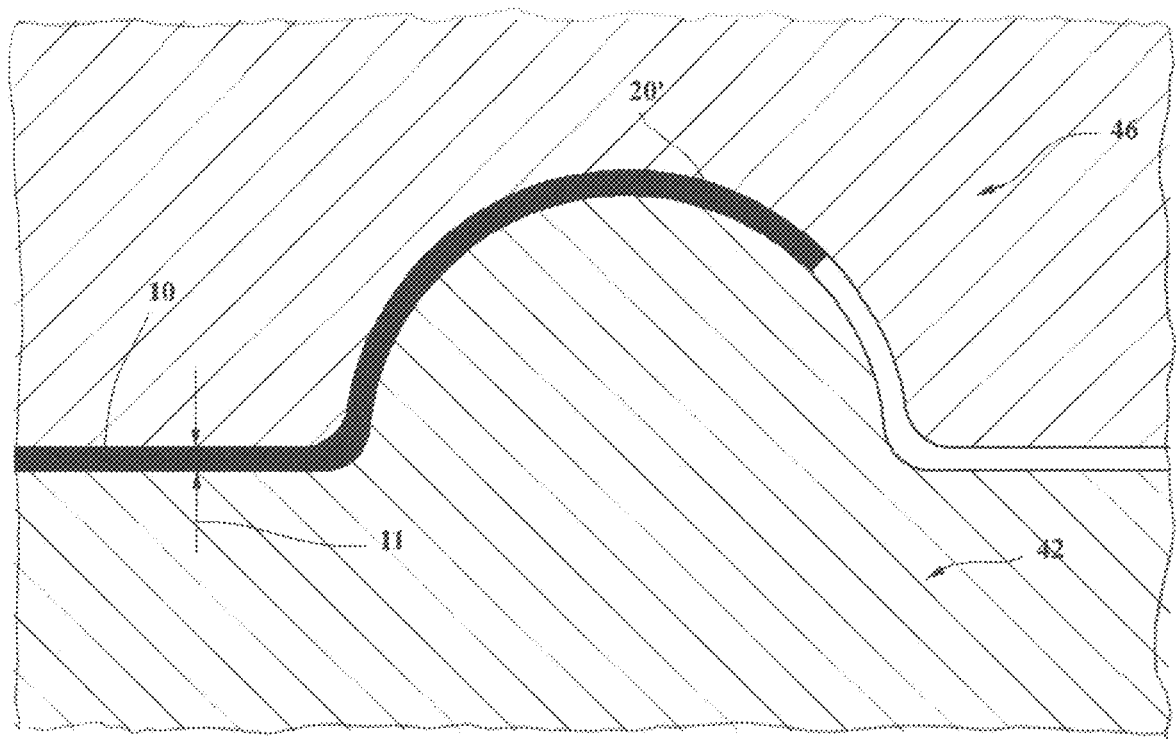
Figure 2H:
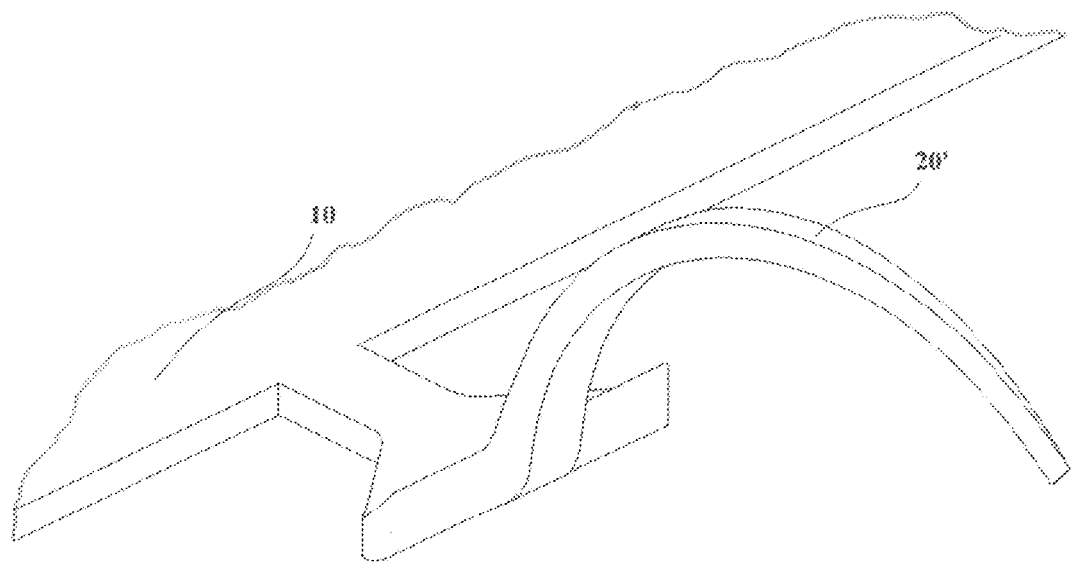
FIG. 2H is a pictorial depiction of the material engagement element in its engagement state.
Figure 2I:
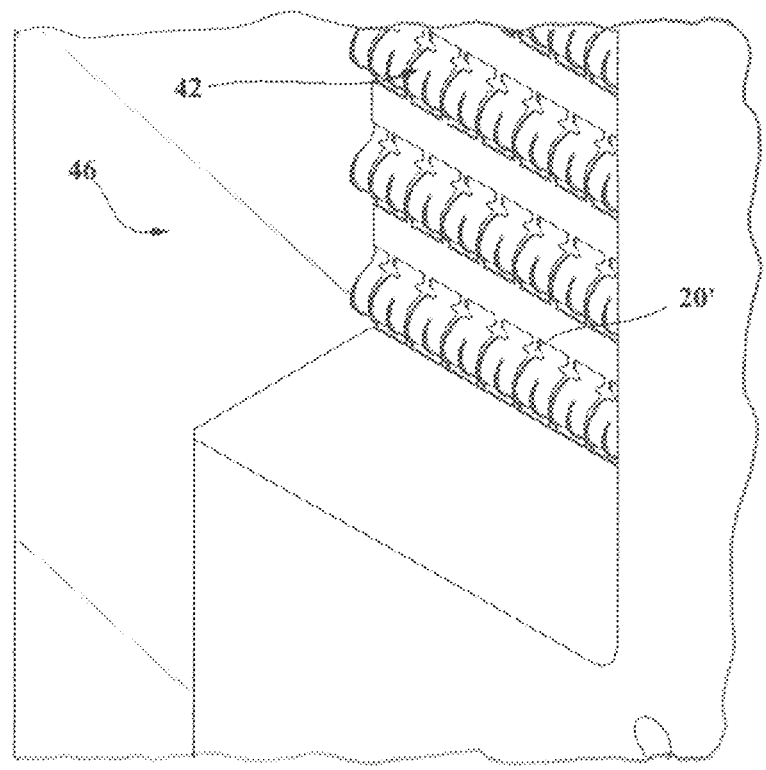
FIG. 2I is an enlarged view of a portion of FIG. 2C.
Figure 2J:
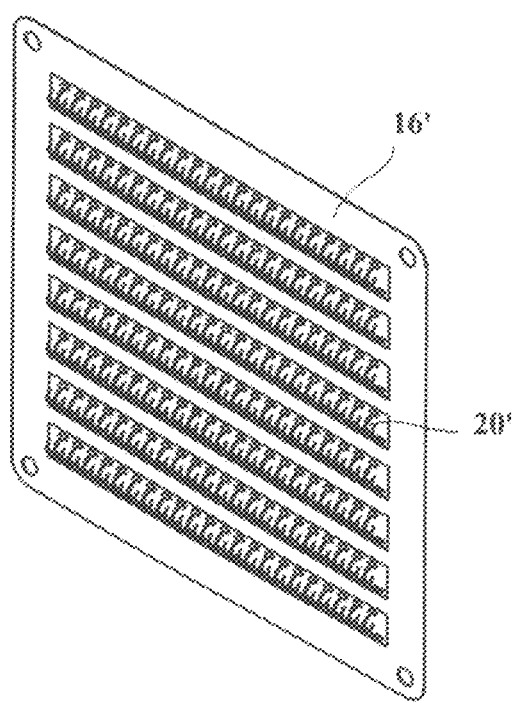
FIG. 2J is a perspective view of the material engagement element sheet of FIG. 1B with the elements in an engagement state.

FIG. 2A depicts a bottom radius fixture 42. The bottom radius fixture 42 incorporates a pattern of positive radii bosses 44, the profiles of which conform to the desired radii to be set into the material engagement elements 20. FIG. 2B shows the material engagement element sheet 16 placed onto the bottom radius fixture 42. The material engagement element sheet location holes 18 are located such that placing the material engagement element sheet 16 over guiding posts on the bottom radius fixture 42 aligns the material engagement element slots 14 with the positive radii bosses 44. FIG. 2C shows a cut away view of the top radius fixture 46 placed into position over the bottom radius fixture 42. The top radius fixture 46 incorporates a pattern of radius slots 48, the profiles of which conform to the desired radii to be set into the material engagement elements 20. FIG. 2D shows a cut away view of the bottom radius fixture 42, the top radius fixture 48, the radius slot 48, a positive radius boss 44, and an individual material engagement element 20. Section A-A in FIG. 2D is through the material engagement element 20, and FIG. 2E shows the orientation of the material engagement element 20 with respect to the bottom radius fixture 42 and top radius fixture 46. As seen in FIG. 2D, the radius dimension 49 (labeled in this text as r1) that defines the profile of the radius slot 48 may be within the range $r1=W/(2*\pi)$ to $r1=W/\pi$, where W is the width dimension 24 of the material engagement element slot 14. Also shown in FIG. 2D is the radius dimension 47 (labeled in this text as r2) which defines the profile of the positive radius boss 44. The radius r2 is defined by the equation $r2=r1-t$ where r1 is the radius of the radius slot 48, and t is the thickness of the sheet material 10. The center of r2 is offset from the surface if the bottom radius fixture 42 by the distance t as shown in FIG. 2D. FIG. 2F shows an applied force 50 squeezing the top radius fixture 46 into the bottom radius fixture 42 thus forcing the material engagement element 20 to begin to conform to the profiles of the radius slot 48 and the positive radius boss 44. FIG. 2G shows the top radius fixture 46 completely deployed onto the bottom radius fixture 42 thus confining the material engagement element 20 to its engagement state 20' as shown in FIG. 2H. FIG. 2I shows a close up view of FIG. 2C with the top radius fixture 46, the bottom radius fixture 42, and the material engagement elements in their engagement state 20'. FIG. 2J shows the material engagement element sheet (elements in engagement state) 16', and the material engagement elements in engagement state 20'. When confined as shown in FIGS. 2C, 2G, and 2I the material engagement element sheet 16 may be shape set with a temperature cycle appropriate to the material. After the engagement shape has been set into the material engagement elements 20', it may be desirable to reshape them back into a flat state before any subsequent processing is performed.

Figure 3A:
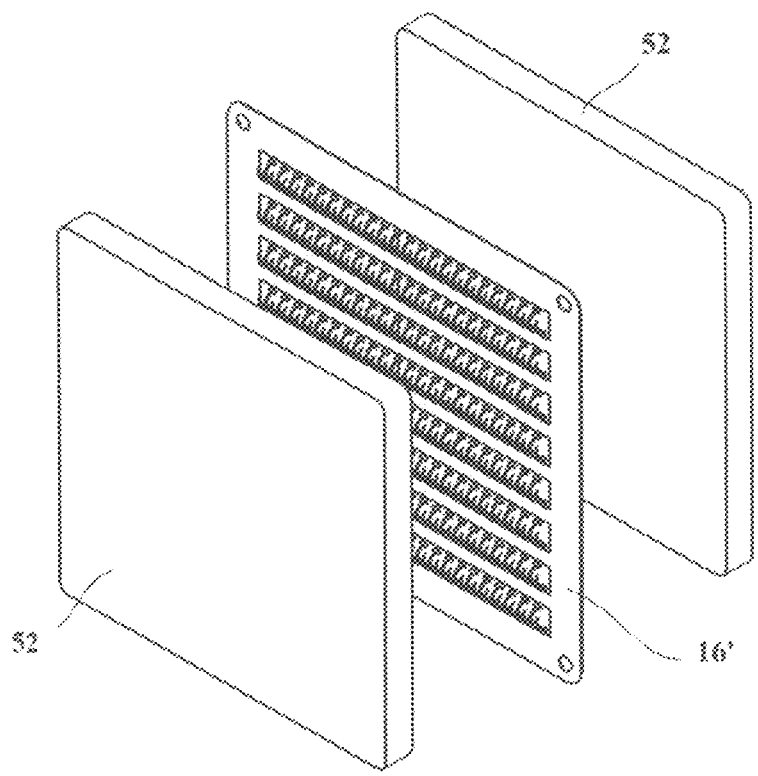
FIGS. 3A-3D depict the material engagement element sheet with the elements in an engagement state of FIG. 2J being transformed into a material engagement element sheet with elements in a flat state via an applied force to two flat plate fixtures.
Figure 3B:
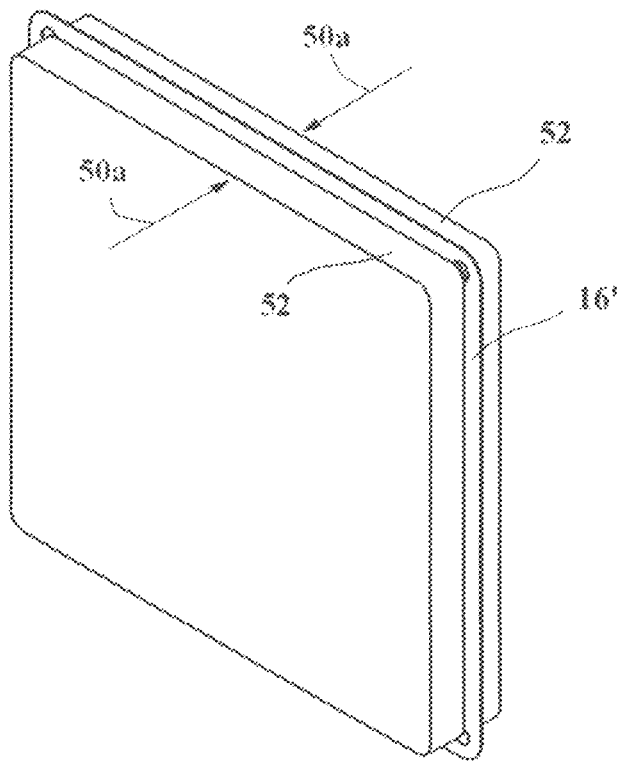
Figure 3C:
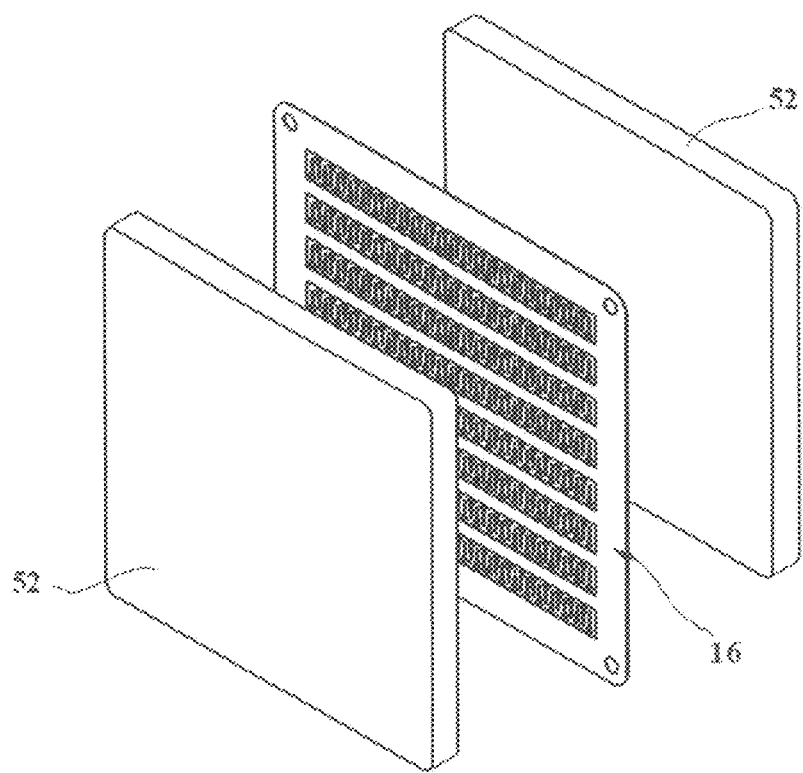
Figure 3D:
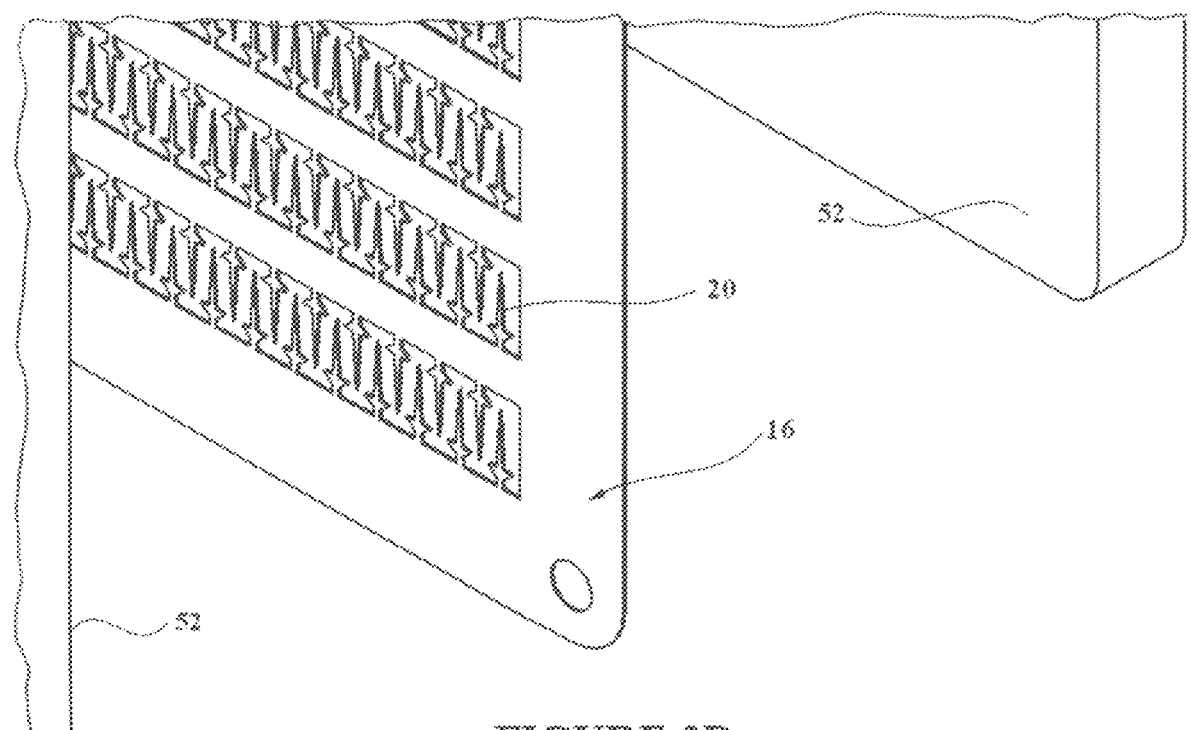

FIG. 3A is a perspective view of the material engagement element sheet (elements in engagement state) 16' and two flat plate fixtures 52. FIG. 3B shows the two flat plate fixtures 52 forced into contact with the material engagement element sheet (elements in engagement state) 16' by an applied force 50a thus forcing the material engagement elements in engagement state 20' into material engagement elements in a flat state 20. FIG. 3C shows the flat plate fixtures 52 being removed and the resulting material engagement element sheet 16. FIG. 3D is a close up view of FIG. 3C showing the flat plate fixtures 52, the material engagement element sheet 16, and the material engagement elements 20 in a flattened state.

Figure 4A:
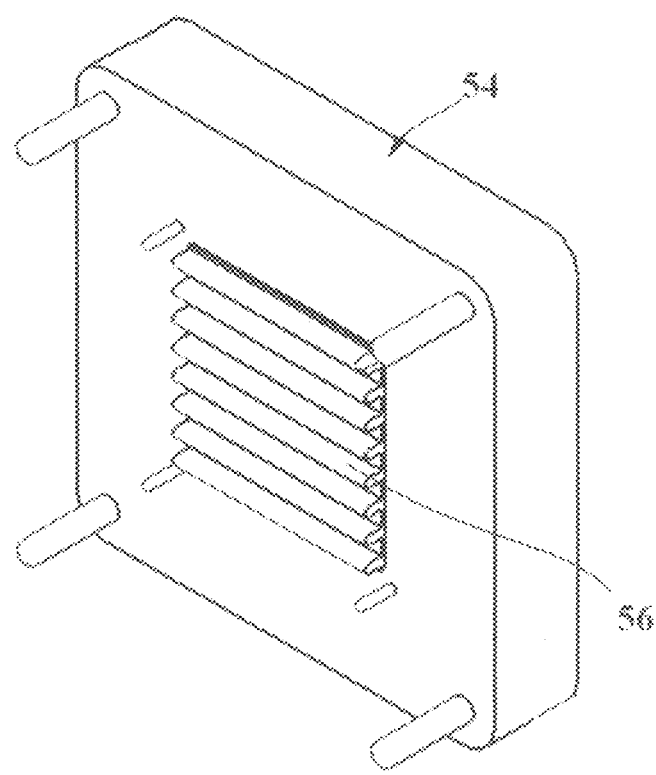
FIG. 4A is a perspective view of a bottom perpendicular fixture.
Figure 4B:
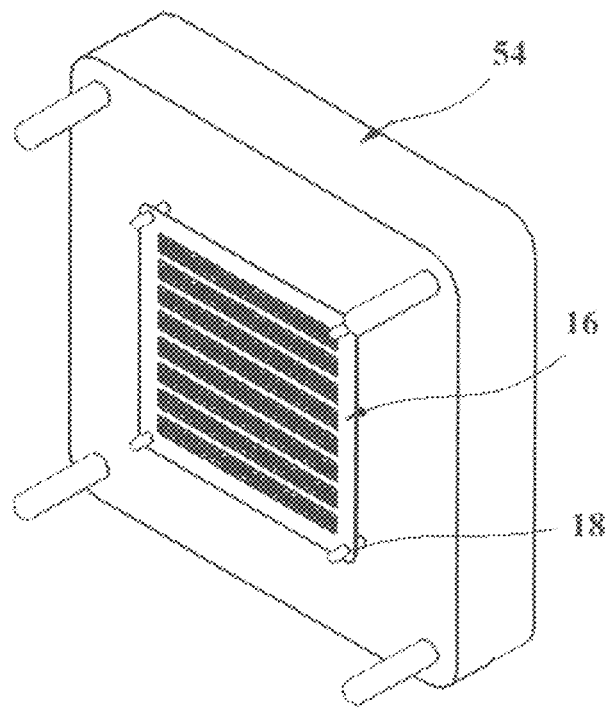
FIG. 4B is a perspective view of the bottom perpendicular fixture of FIG. 4A with the material engagement element sheet placed over it.
Figure 4C:
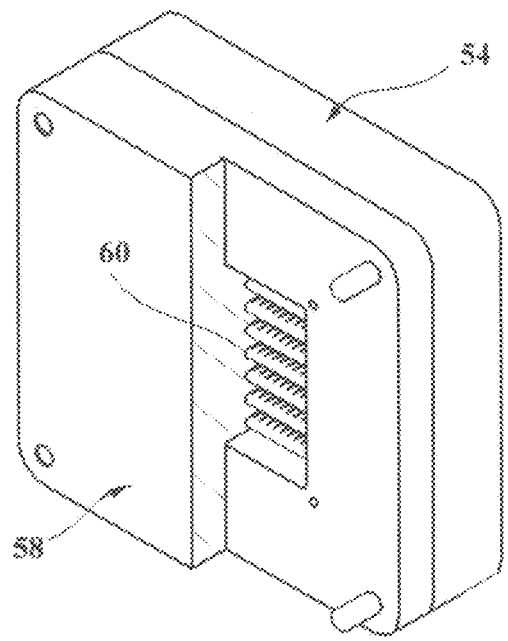
FIG. 4C is a perspective view of the bottom perpendicular fixture which is shown in section view, a top perpendicular fixture, and the material engagement element sheet with the fixtures engaged and the elements in a perpendicular state.
Figure 4D:
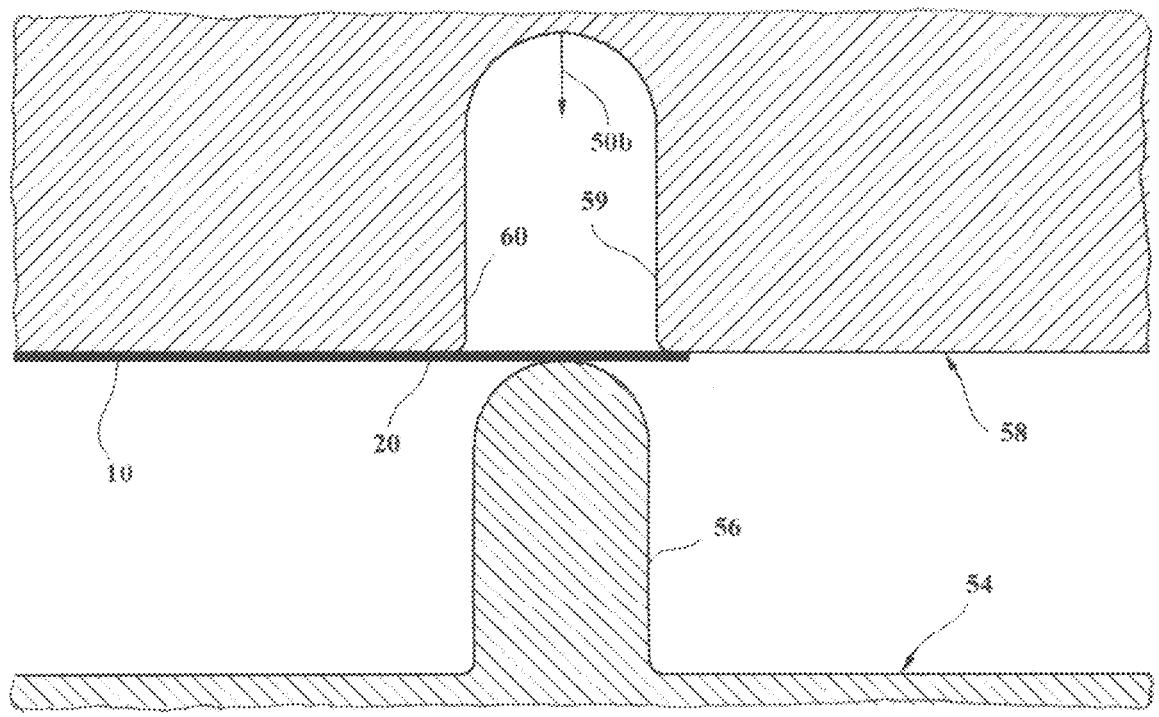
FIGS. 4D and 4E are cut away views of the top and bottom perpendicular fixtures forced together in order to shape an engagement element into a perpendicular state.
Figure 4E:
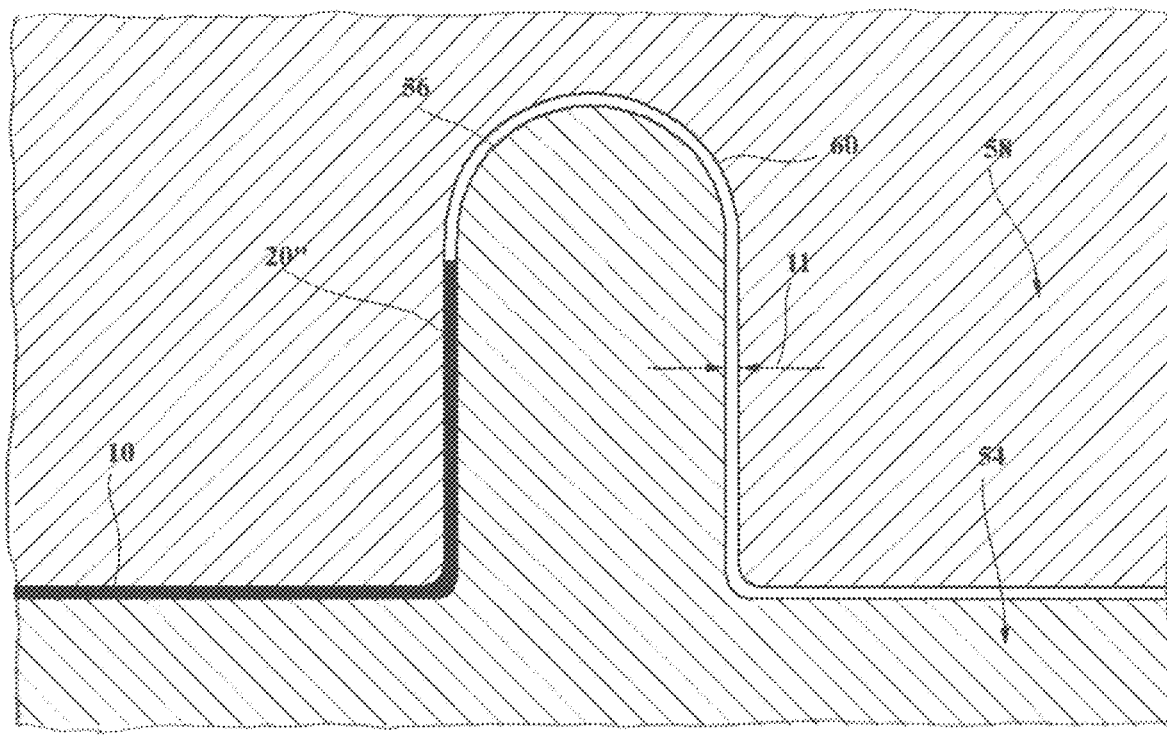
Figure 4F:
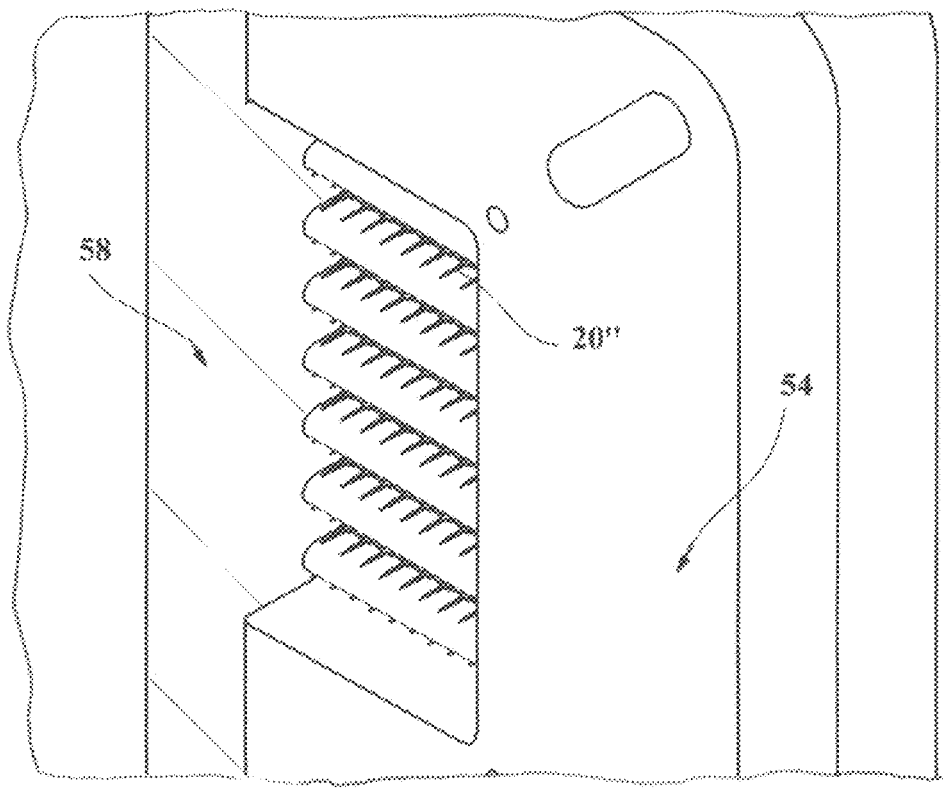
FIG. 4F is an enlarged view of FIG. 4C.
Figure 4G:
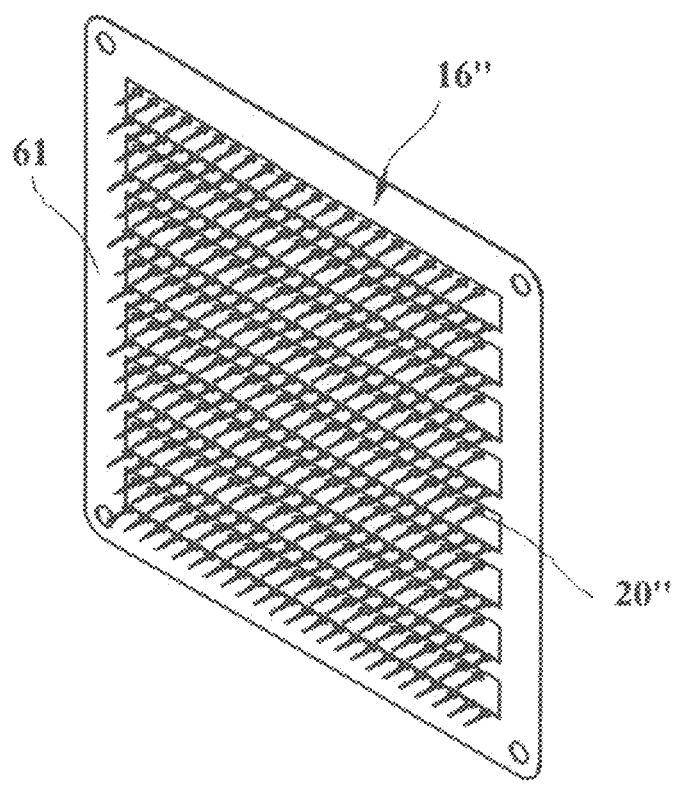
FIG. 4G is a perspective view of the material engagement element sheet with the elements in a perpendicular state.

The methods discussed henceforth to complete the manufacturing of the material engagement element pad apply to all embodiments of the sheet material 10. The material engagement elements 20 can now be manipulated such that they are in a state that is substantially perpendicular to the surface of the sheet material 10. FIG. 4A is a perspective view of a bottom perpendicular fixture 54 which incorporates a pattern of positive perpendicular bosses 56. FIG. 4B shows the material engagement element sheet 16 placed onto the bottom perpendicular fixture 54. The material engagement element sheet location holes 18 are located such that placing the material engagement element sheet 16 over guiding posts on the bottom perpendicular fixture 54 aligns the material engagement element slots 14 with the positive perpendicular bosses 56. The positive perpendicular bosses 56 provide a surface whose profile is perpendicular to the surface of the sheet material 10. FIG. 4C shows a cut away view of the top perpendicular fixture 58 placed into position over the bottom perpendicular fixture 54. FIG. 4D shows a cut away view of the bottom perpendicular fixture 54, the top perpendicular fixture 58, the perpendicular slot 60, a positive perpendicular boss 56, an applied force 50b, and an individual material engagement element 20. The top perpendicular fixture 58 incorporates perpendicular slots 60 the profile of which incorporate a surface 59 that is perpendicular to the surface of the sheet material 10. For purposes of clarity, the material engagement element sheet 16 is hidden and only the individual material engagement element 20 is shown. FIG. 4D shows the applied force 50b squeezing the top perpendicular fixture 58 towards the bottom perpendicular fixture 54. FIG. 4E shows the top perpendicular fixture 58, the bottom perpendicular fixture 54, and the material engagement element 20 forced into a perpendicular state 20" by the application of the force to the fixtures. As shown in FIG. 4E, the gap between the perpendicular slots 60 and the positive perpendicular bosses 56 is the thickness t of the sheet material 10. Only a single material engagement element 20 is shown extending from one side of the slot in the material engagement element sheet. Alternating elements from the opposite side of the slot are received in the opposing side of the gap between the perpendicular slots 60 and positive perpendicular bosses 56. FIG. 4F shows a close up view of FIG. 4C with the top perpendicular fixture 58, the bottom perpendicular fixture 54, and the material engagement elements in their perpendicular state 20". FIG. 4G shows the material engagement element sheet (elements in engagement state) 16", the surface 61 of the sheet material 10, the material engagement elements in perpendicular state 20", and surface 61 the front of the sheet material 10.

Figure 5A:
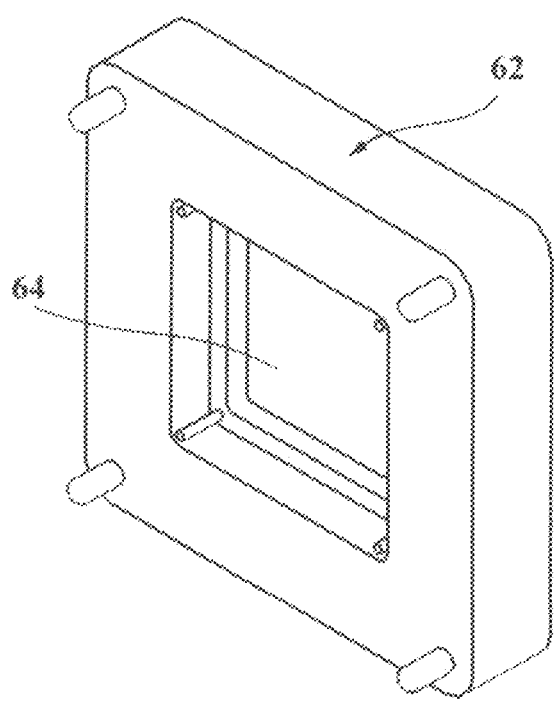
FIG. 5A is a perspective view of a bottom mold fixture which incorporates a temporary stabilizing material mold cavity.
Figure 5B:
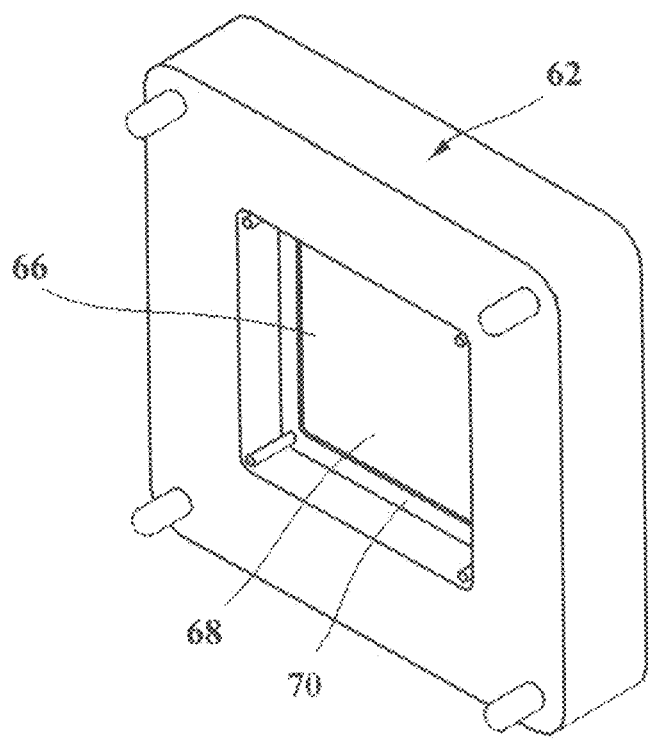
FIG. 5B is a perspective view of the bottom mold fixture of FIG. 5A with the temporary stabilizing material mold cavity partially filled with temporary stabilizing material.
Figure 5C:
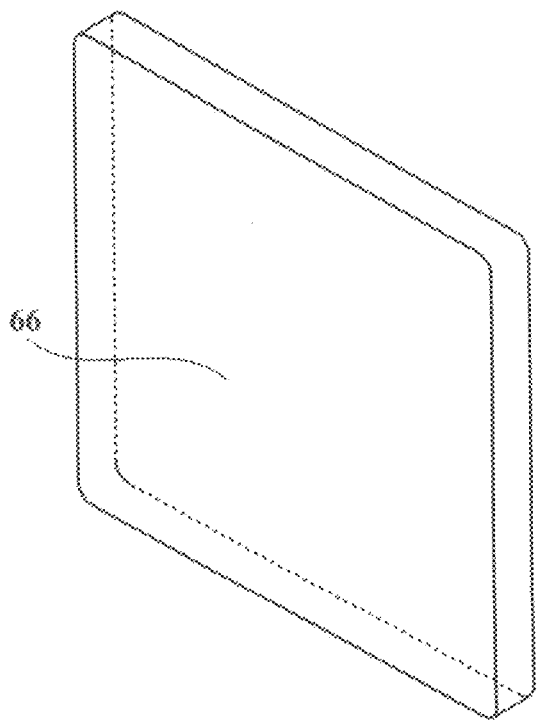
FIG. 5C is a view of the temporary stabilizing material with the bottom mold fixture not shown for clarity of illustration.
Figure 5D:
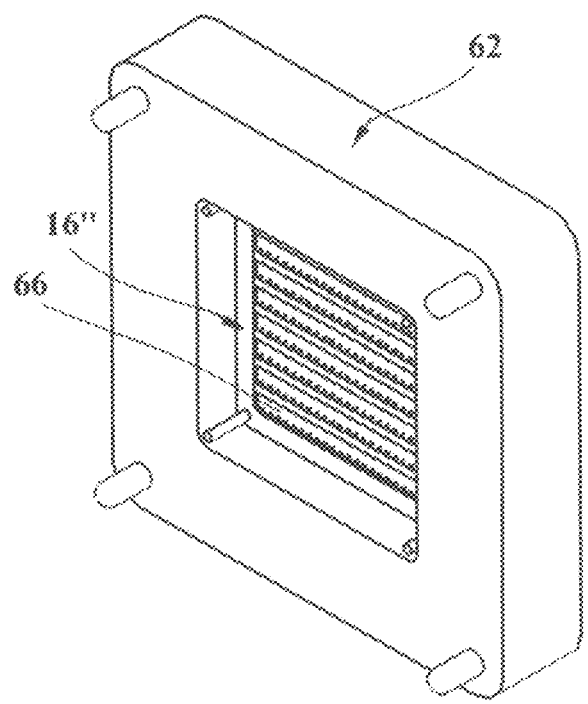
FIG. 5D shows the bottom mold fixture, and the material engagement element sheet with the elements in a perpendicular state partially deployed into the temporary stabilizing material.
Figure 5E:
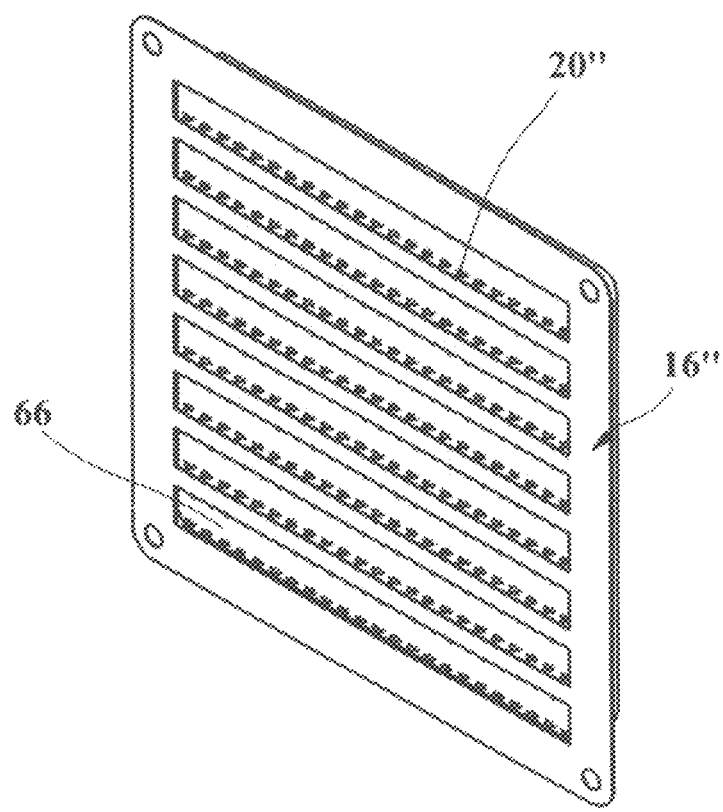
FIG. 5E shows the assembly of FIG. 5D with the bottom mold fixture hidden for clarity of illustration.
Figure 5F:
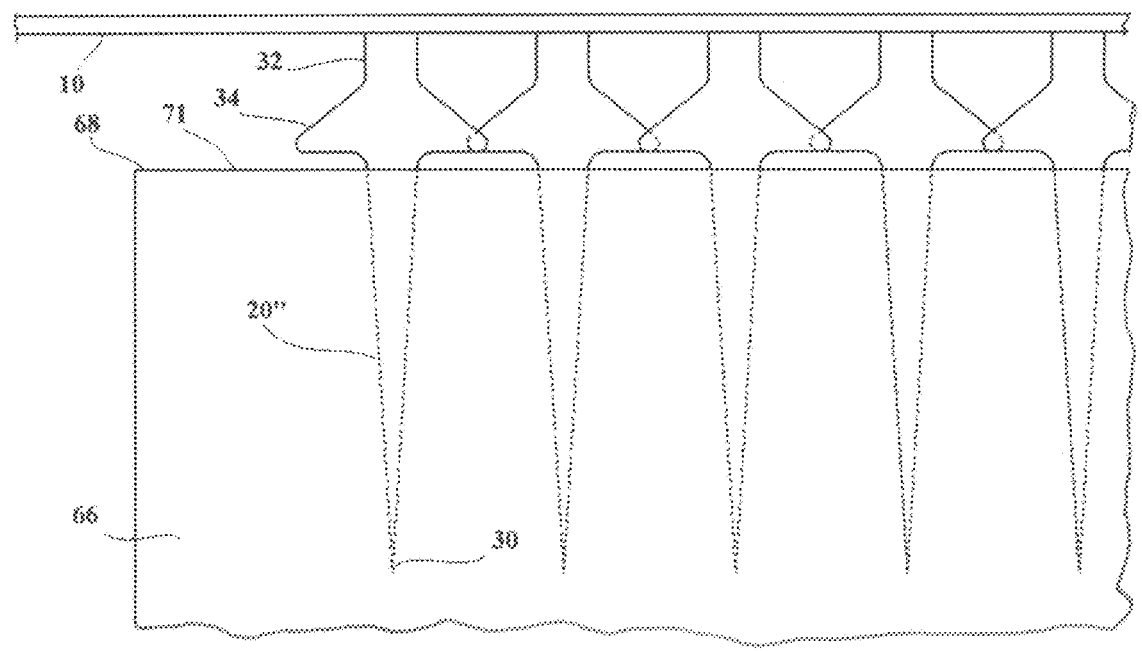
FIG. 5F is an elevation view of the material engagement element sheet with the elements in a perpendicular state, the temporary stabilizing material which surrounds the material engagement element distal ends, and the barrier material.
Figure 5G:
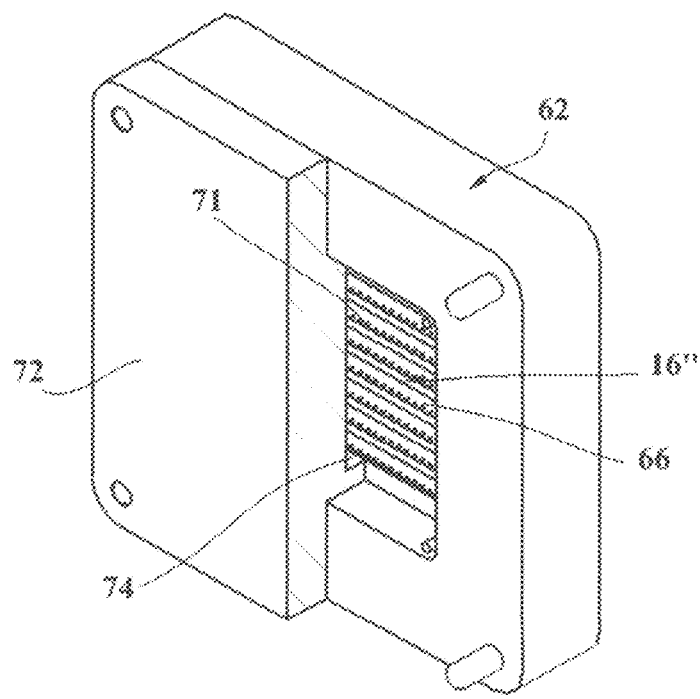
FIG. 5G shows FIG. 5E with the addition of top mold fixture which is shown in a section view.
Figure 5H:
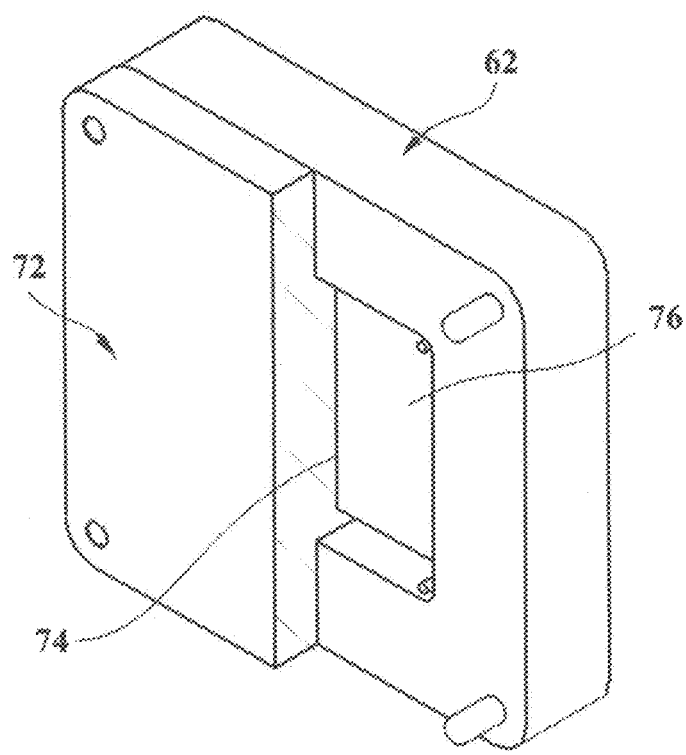
FIG. 5H shows the assembly of FIG. 5G with a flexible base material added to a mold cavity in the top mold fixture which is shown in section view.

For certain example embodiments of the material engagement element pad it is desirable to integrate a flexible base material 76 around the material engagement element proximal ends 32, while leaving the material engagement element distal ends 30 free from flexible base material 76. The use of a temporary stabilizing material 66 is one method by which this may be accomplished. FIG. 5A is a perspective view of a bottom mold fixture 62. The bottom mold fixture 62 incorporates the temporary stabilizing material cavity 64. FIG. 5B depicts the temporary stabilizing material cavity 64 partially filled with temporary stabilizing material 66. There is a gap between the upper surface 68 of the temporary stabilizing material 66 and the upper surface of the temporary stabilizing material cavity 70. The temporary stabilizing material 66 may be comprised of any penetrable material such as a polymer, a rubber, a foam, a gauze, or any other suitable material. The temporary stabilizing material may be a solid material, or a liquid material that cures into a solid. For some embodiments it may be desirable to have a the temporary stabilizing material 66 comprised of a liquid that cures into a solid at room temperature such as a room temperature vulcanization (RTV) silicone, or an RTV urethane. FIG. 5C is a perspective view of the temporary stabilizing material 66 with the bottom mold fixture 62 hidden. FIG. 5D is a perspective view of the bottom mold fixture 62, the material engagement element sheet (elements in perpendicular state) 16", and the temporary stabilizing material 66. The surface 61 of the material engagement element sheet (elements in perpendicular state) 16" and the upper surface of the temporary stabilizing material cavity 70 are coincident in the figure. FIG. 5E the same view as FIG. 5D showing the material engagement element sheet (elements in perpendicular state) 16" and the temporary stabilizing material 66 with the bottom mold fixture 62 hidden. As may be seen in FIG. 5E, the material engagement elements in perpendicular state 20" are partially deployed onto the temporary stabilizing material 66. FIG. 5F is a close up view FIG. 5E showing the material engagement elements in perpendicular state 20" and the temporary stabilizing material 66. The gap between the upper surface 68 of the temporary stabilizing material 66 and the upper surface of the temporary stabilizing material cavity 70 results in the partial deployment of the material engagement elements in perpendicular state 20" into the temporary stabilizing material 66. This leaves the material engagement element proximal ends 32, and the material engagement element flanges 34 outside of the temporary stabilizing material 66, while the material engagement element distal ends 30 are encapsulated in the temporary stabilizing material 66. Also shown in FIG. 5F is a barrier material 71 applied to surface 68 of the temporary stabilizing material 66. The barrier material 71 prevents the bonding of any material applied to surface 68 of the temporary stabilizing material 66. The barrier material 71 may be a spray on material such as mold release or a Teflon coating, or the barrier material 71 could be a bond resistant sheet material such as Teflon sheet. FIG. 5H shows a cut-away of the top mold fixture 72 in place over the bottom mold fixture 62, the top mold fixture mold cavity 74, the material engagement element sheet (elements in perpendicular state) 16", the top mold fixture mold cavity filled with flexible base material 76, and the barrier material 71. The flexible base material 76 may be any material that cures from a liquid state to a solid state such as silicone, a two part urethane, a curable foam, or any other suitable material.

Figure 5I:
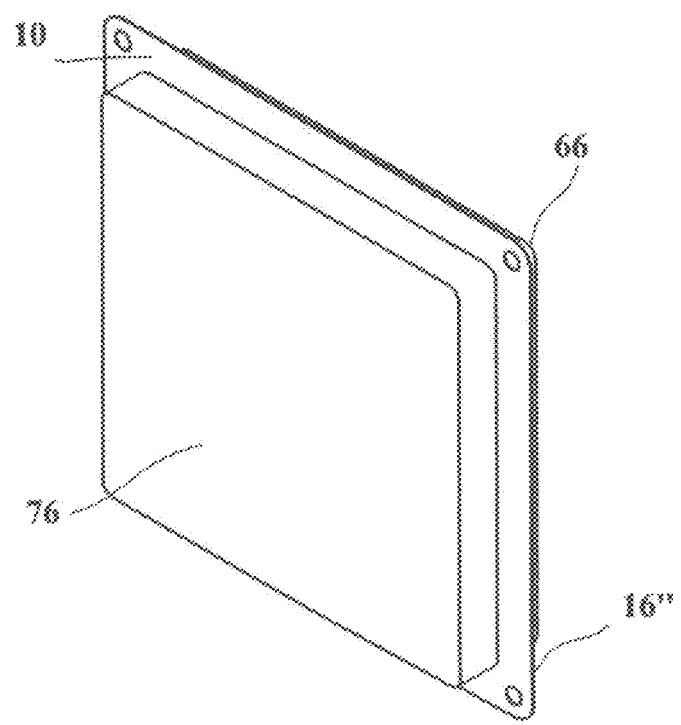
FIG. 5I shows the assembly of FIG. 5H with the top and bottom mold fixtures hidden for clarity of illustration.
Figure 5J:
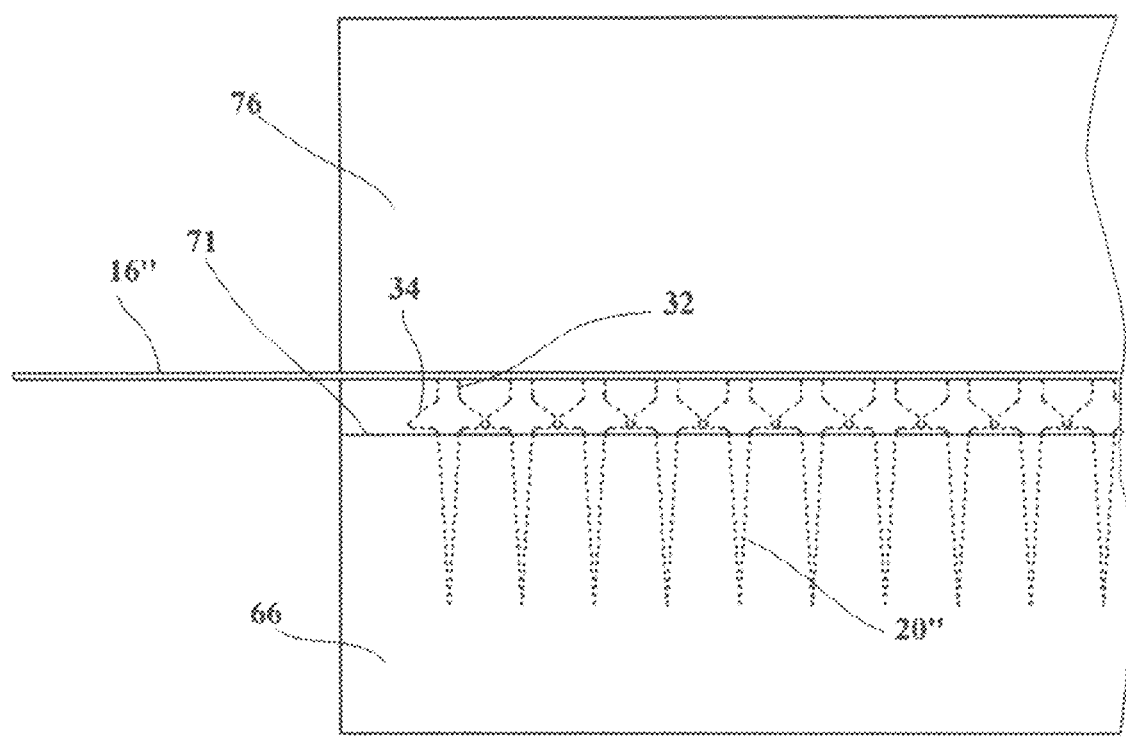
FIG. 5J is an elevation view of the material engagement element sheet with the elements in a perpendicular state, the temporary stabilizing material, the flexible base material, and the barrier material.

FIG. 5I is a perspective view of an embodiment showing the material engagement element sheet with elements perpendicular 16", the temporary stabilizing material 66, the flexible base material 76, and the sheet material 10 which remains beyond the temporary stabilizing material 66 and the flexible base material 76 once the embodiment has been removed from bottom mold fixture 62 and the top mold fixture 72. FIG. 5J is a close up hidden lines shown view of the embodiment of FIG. 5I showing the stabilizing material 66, the flexible base material 76, the barrier material 71, the material engagement element sheet with elements perpendicular 16", the material engagement elements in perpendicular state 20", and the sheet material 10 which remains beyond the temporary stabilizing material 66 and the flexible base material 76. As can be seen in the figure, the flexible base material 76 encompasses the material engagement element proximal ends 32 and the material engagement element flanges 34 thus mechanically fixing the material engagement elements in perpendicular state 20" into the flexible base material 76.

Figure 6A:
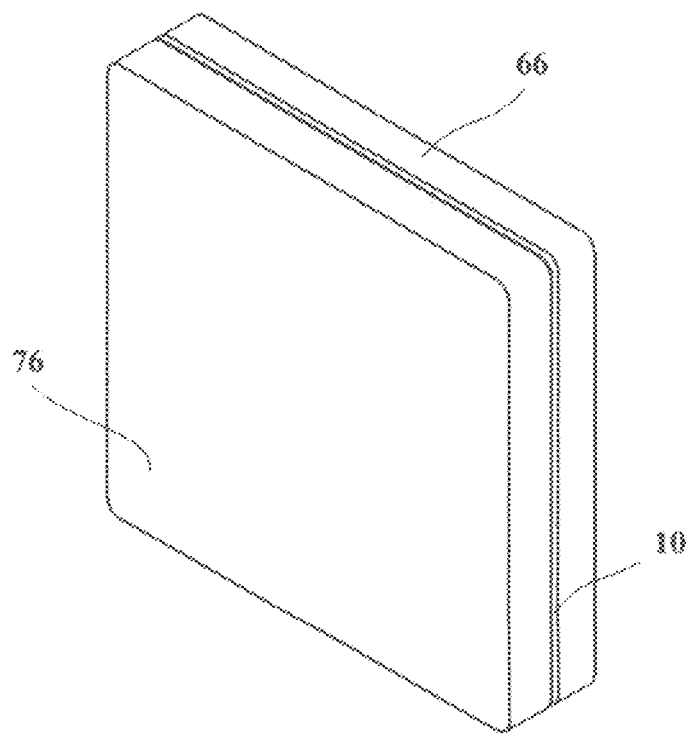
FIG. 6A illustrates the assembly of FIG. 5J with the excess sheet material trimmed after the assembly has been removed from the top mold fixture and the bottom mold fixture.
Figure 6B:
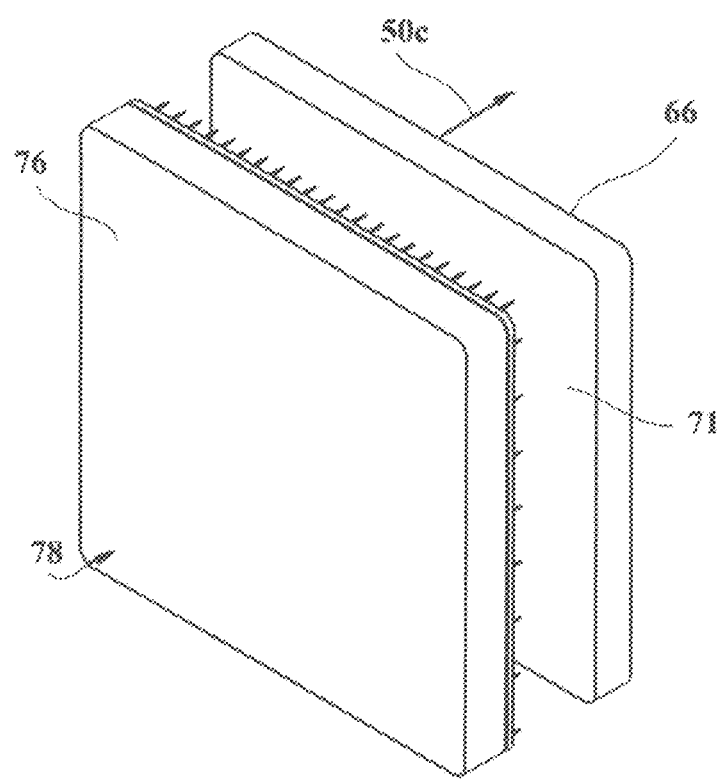
FIGS. 6B and 6C illustrate the removal of the temporary stabilizing material from the material engagement element pad assembly.
Figure 6C:
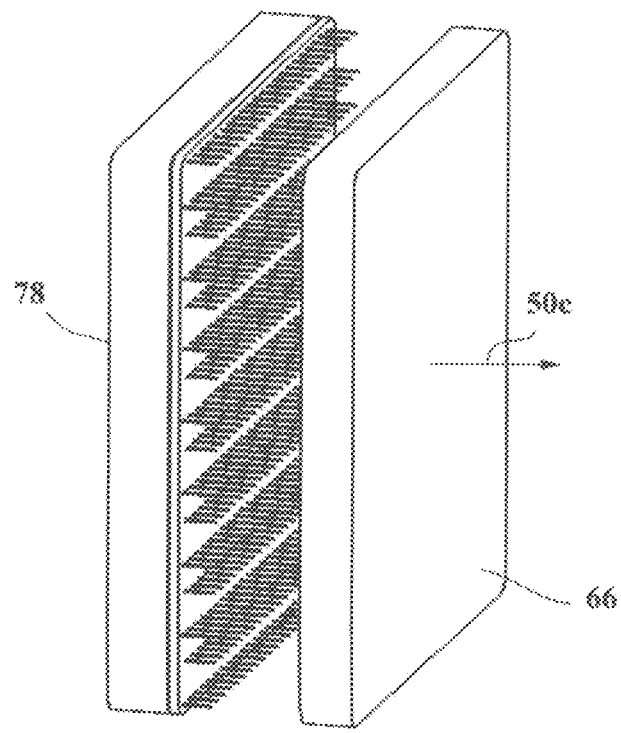
Figure 6D:
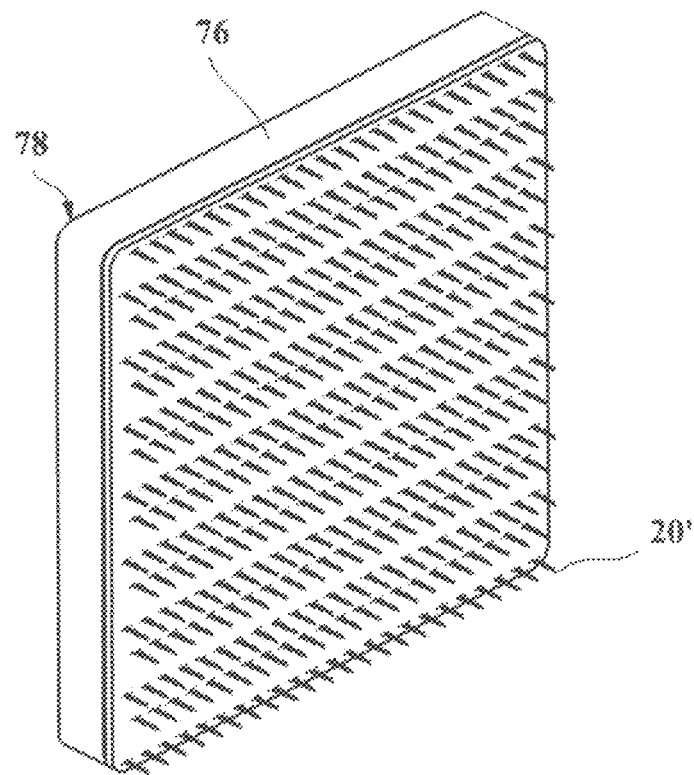
FIG. 6D is a perspective view of an engagement pad assembly ready for deployment.

FIG. 6A is a perspective view of the embodiment of FIGS. 5I and 5J showing the temporary stabilizing material 66, the flexible base material 76, and the sheet material 10 which remained beyond the temporary stabilizing material 66 and the flexible base material 76 trimmed off such that the sheet material 10 is flush with the profiles of the temporary stabilizing material 66 and the flexible base material 76. FIG. 6B is a perspective view of the temporary stabilizing material 66 being removed from the material engagement pad element assembly 78 through an applied force 50c. The barrier material 71 prevents the temporary stabilizing material 66 from adhering to the flexible base material 78. FIG. 6C is another view of FIG. 6B, showing the temporary stabilizing material 66 being removed from the engagement pad assembly by an applied force 50c. The temporary stabilizing material 66 would be removed just prior to the deployment of the material engagement element pad assembly 78. FIG. 6D is a perspective view of the engagement pad assembly 78 including the flexible base material 76 and the material engagement elements in perpendicular state 20".

Figure 7B:
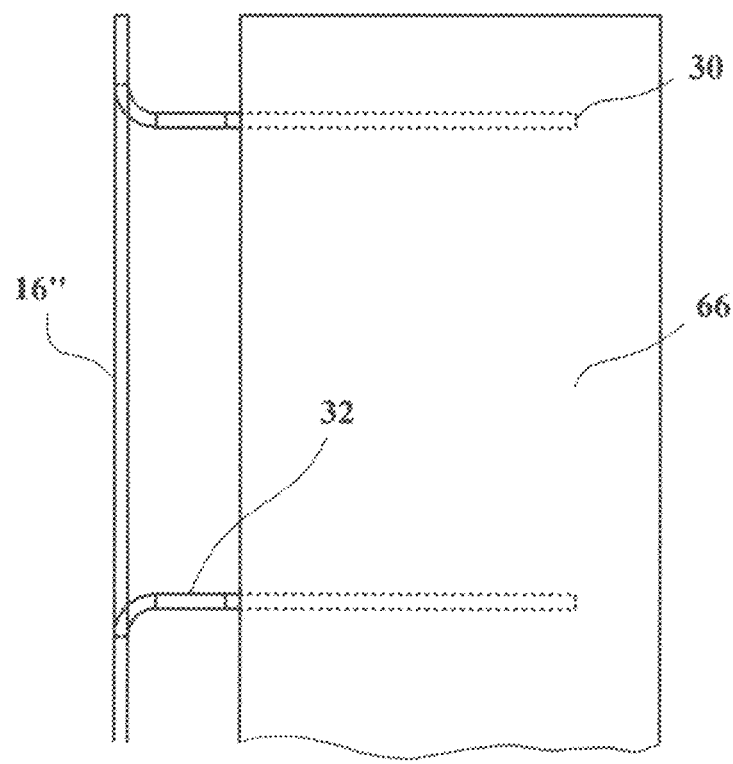
FIG. 7B is an enlarged view of the assembly of FIG. 7A.
Figure 7C:
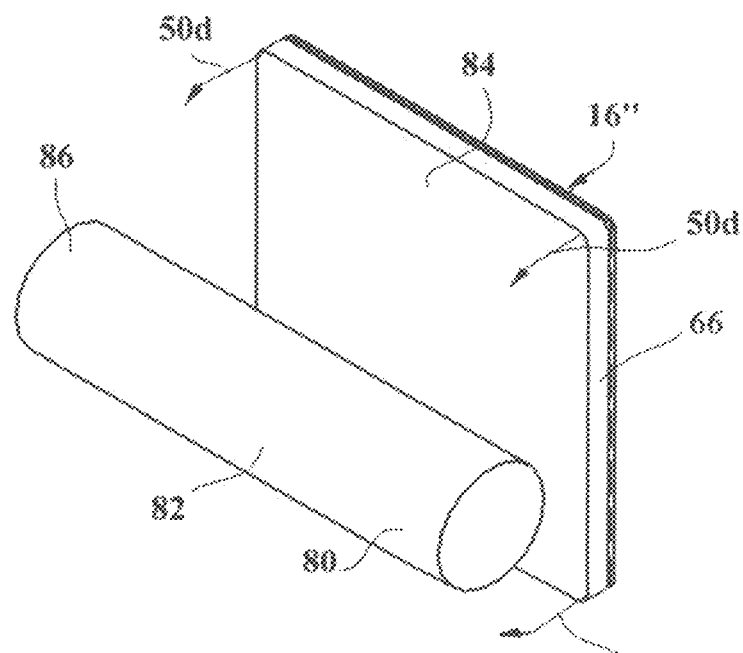
FIG. 7C depicts a cylindrical mandrel and the assembly of FIGS. 7A and 7B.
Figure 7D:
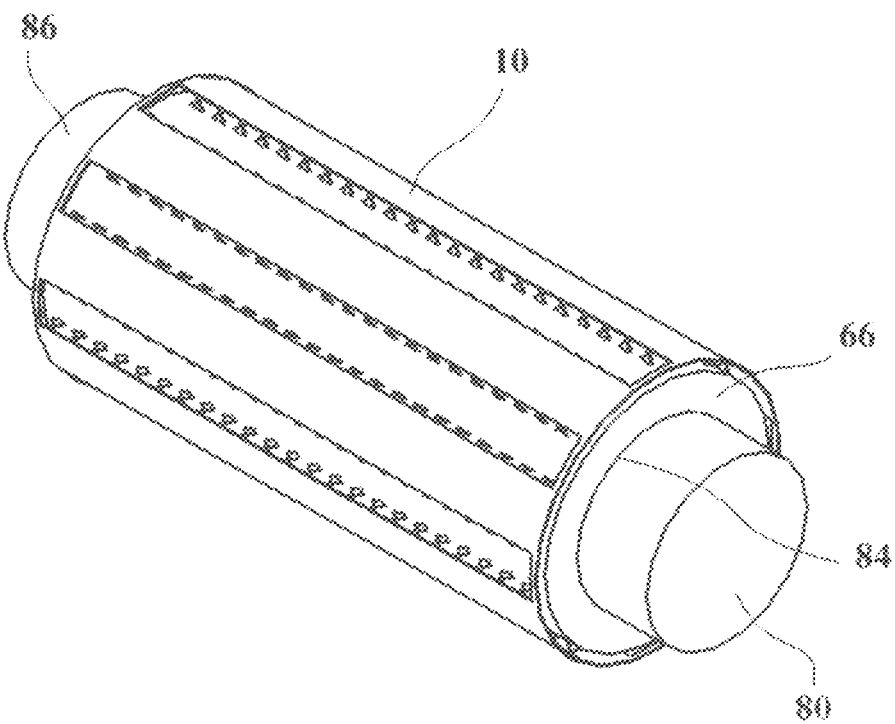
FIG. 7D illustrates the assembly of FIGS. 7A and 7B wrapped around the cylindrical mandrel.
Figure 7E:
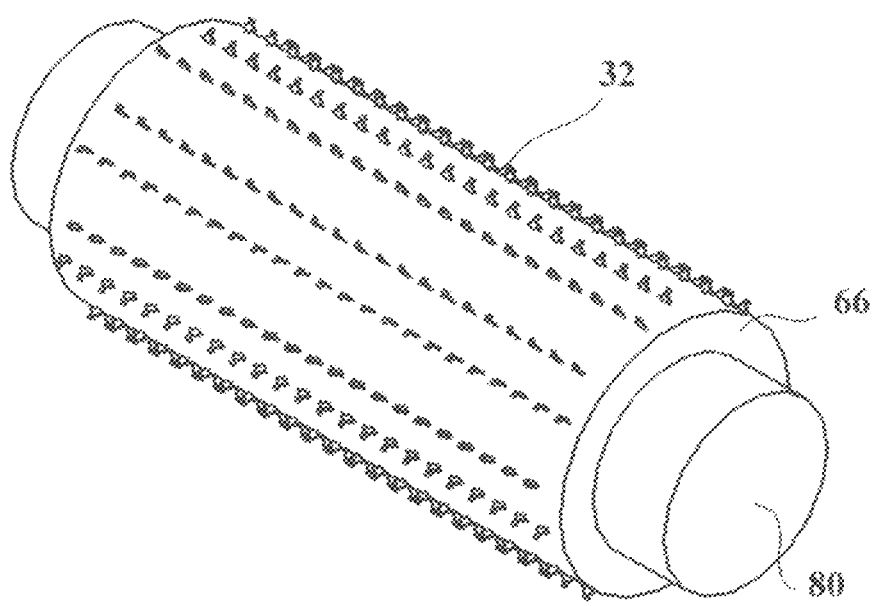
FIG. 7E is the assembly shown in FIG. 7D with the excess sheet material trimmed off of the material engagement element sheet with elements in perpendicular state.
Figure 7F:
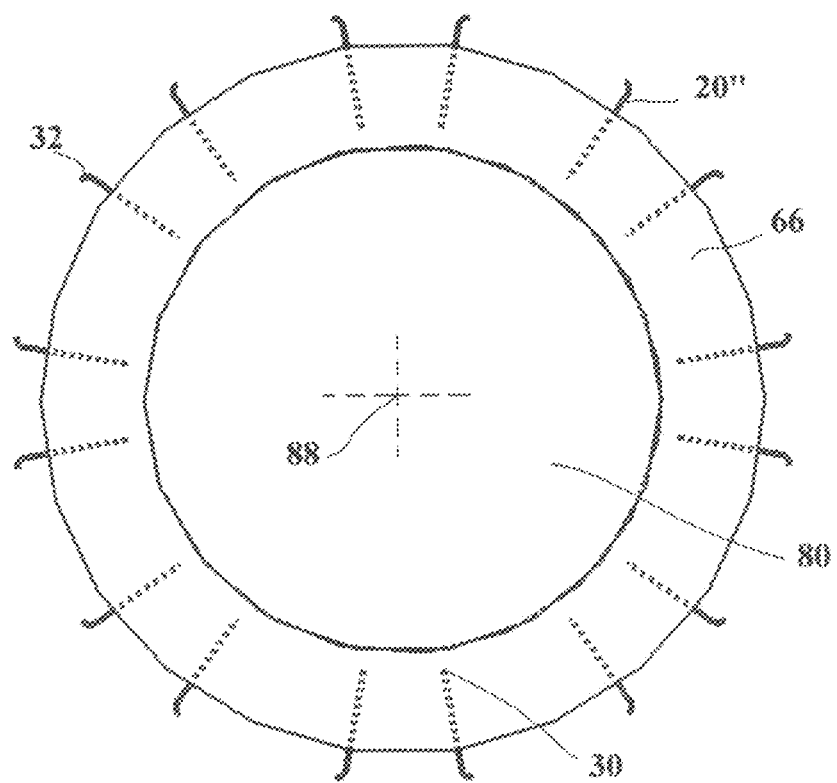
FIG. 7F is a cross section view of the assembly of FIG. 7E showing the material engagement element distal tips pointing inward toward the axis of the cylindrical mandrel.
Figure 7G:
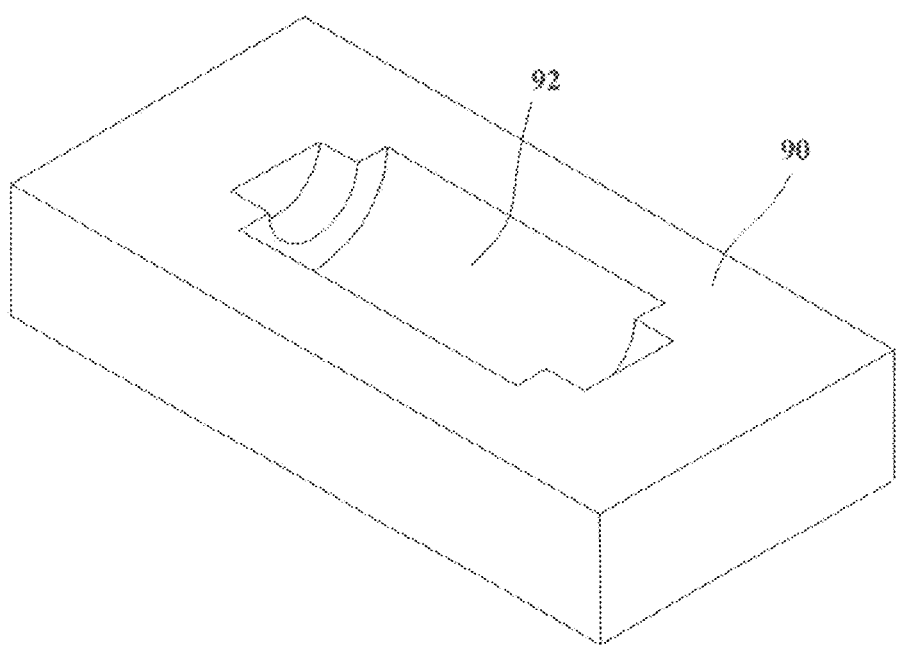
FIG. 7G shows a bottom cylindrical mold.
Figure 7H:
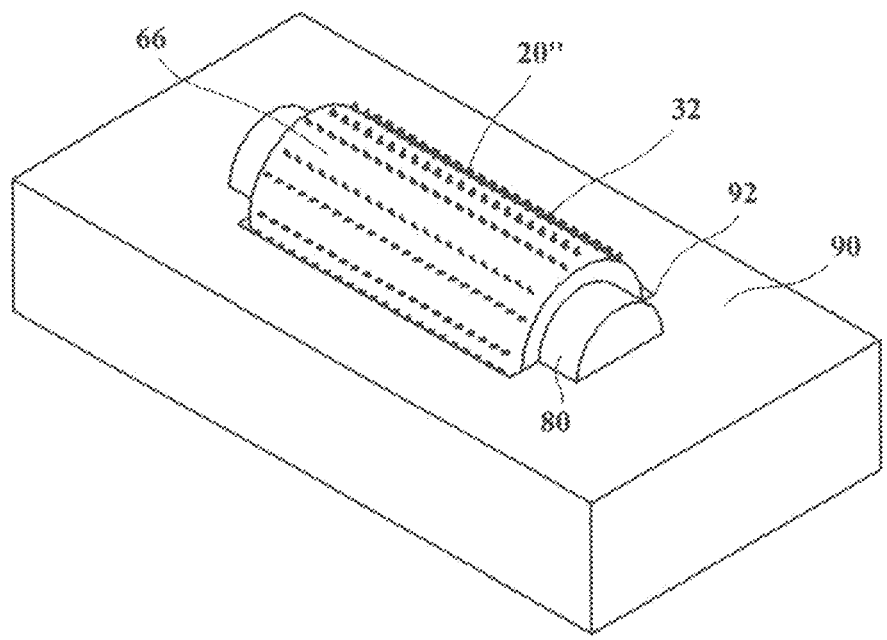
FIG. 7H shows the assembly of FIG. 7E loaded into the bottom cylindrical mold of FIG. 7G.
Figure 7I:
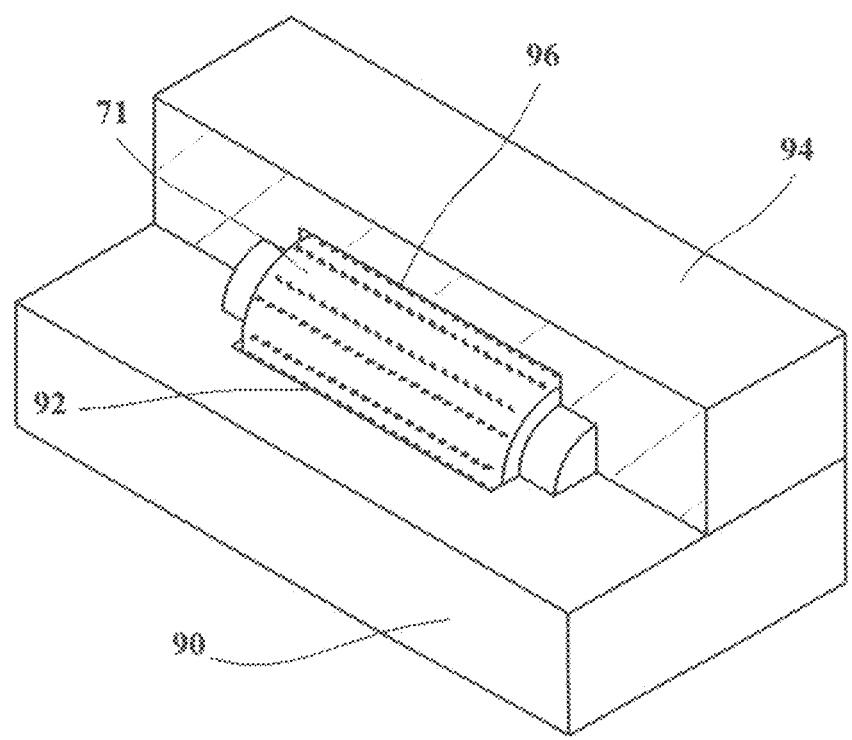
FIG. 7I illustrates the assembly of FIG. 7H with the addition of a top cylindrical mold which is shown in section view and which is engaged with the bottom cylindrical mold.
Figure 7J:
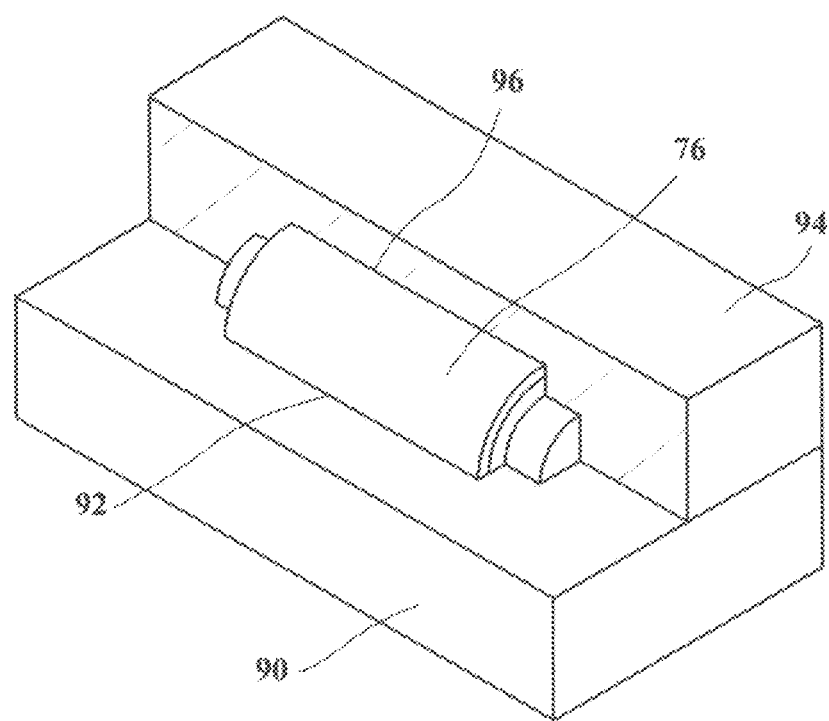
FIG. 7J shows the assembly of FIG. 7I with the addition of a flexible base material added to the top cylindrical mold cavity and the bottom cylindrical mold cavity.
Figure 7K:
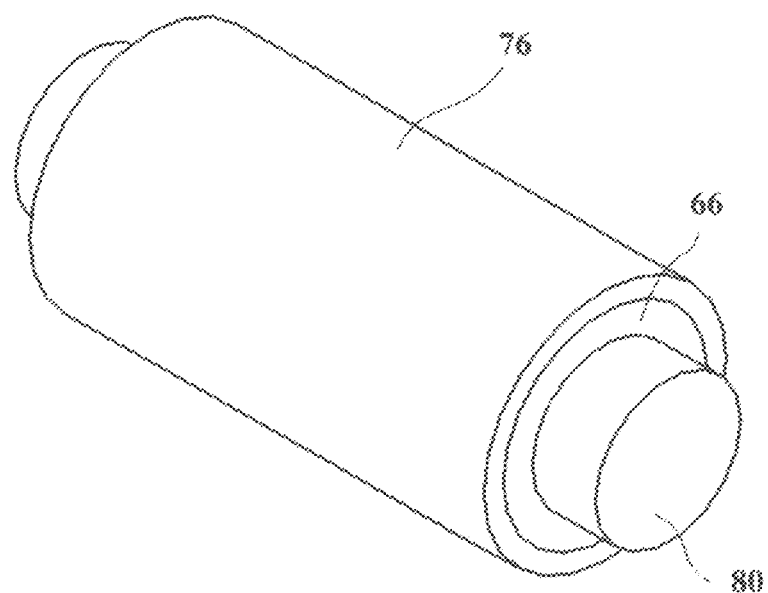
FIG. 7K illustrates an assembly of the temporary stabilizing material, the flexible base material, and the cylindrical mandrel after the assembly has been removed top cylindrical mold and the bottom cylindrical mold.
Figure 7L:
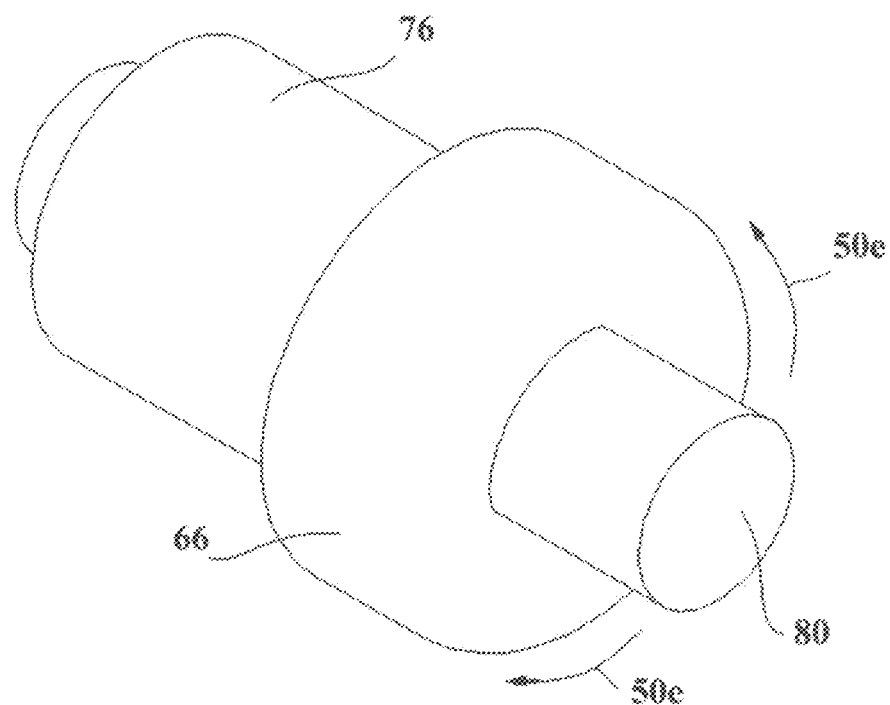
FIGS. 7L and 7M depict the removal and inversion of the temporary stabilizing material and flexible base material from the cylindrical mandrel.
Figure 7M:
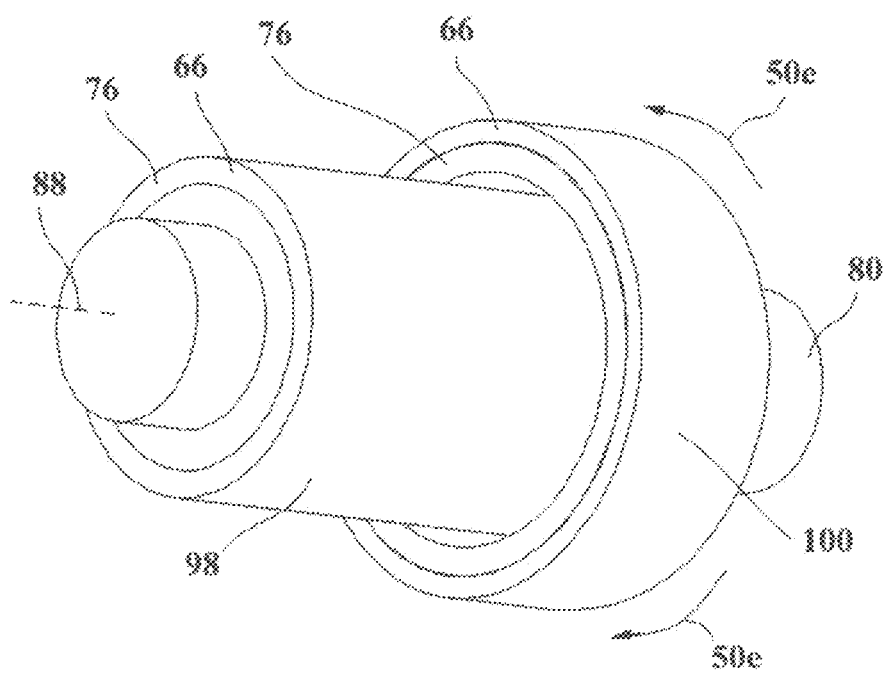
Figure 7N:
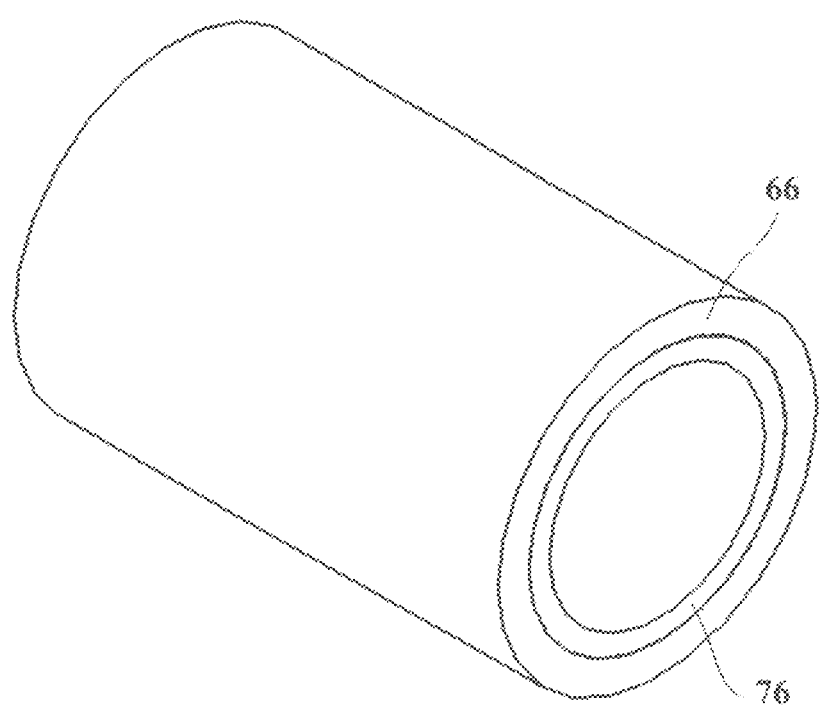
FIG. 7N shows the inverted flexible base material and temporary stabilizing material assembly.
Figure 7O:
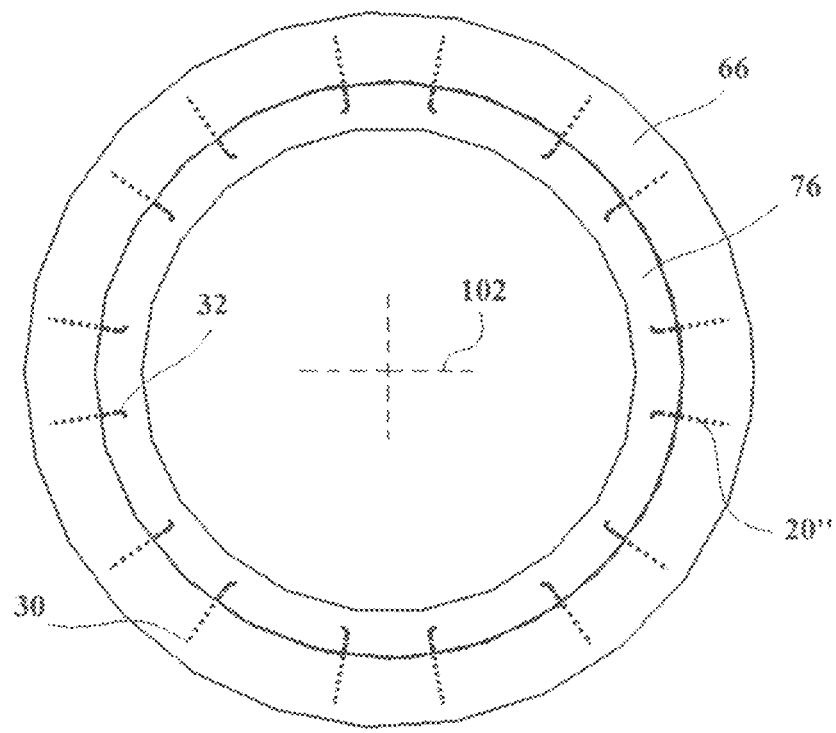
FIG. 7O is a cut away view of the assembly of FIG. 7N showing the material engagement element distal ends pointing away from the central axis of the assembly.
Figure 7P:
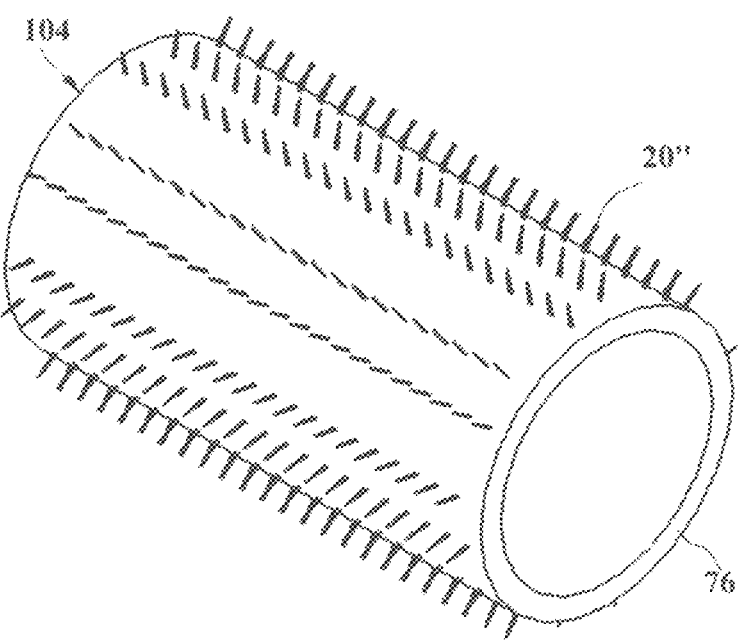
FIG. 7P is the cylindrical material engagement element device after the temporary stabilizing material has been removed.
Figure 7Q:
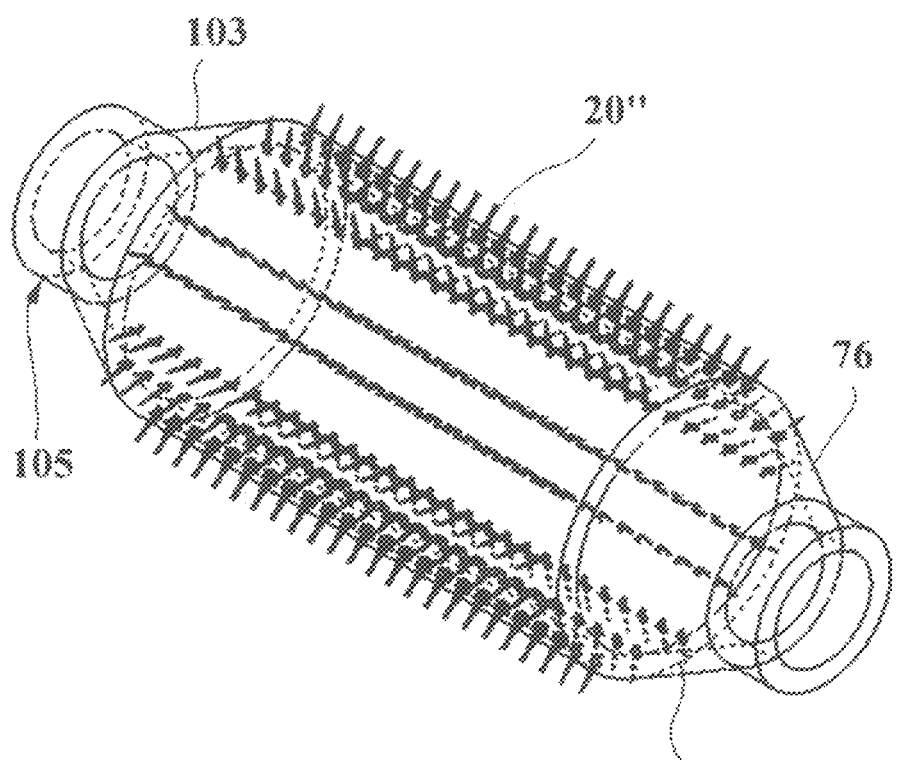
FIG. 7Q is another embodiment of the cylindrical material engagement element device wherein the flexible base material is configured as a balloon.
Figure 9A:
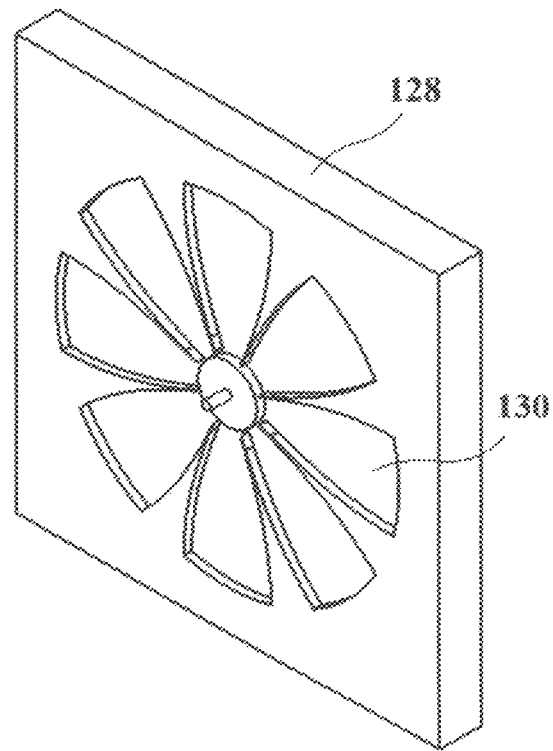
FIG. 9A shows a spherical flat mold fixture.

In PCT/US09/57348 FIG. 9A and paragraph 72 describe a cylindrical tube comprised of flexible base material and an array of engagement elements, a configuration which will hereto be referred to as a cylindrical material engagement element device. The methods discussed herein detail the manufacture of a cylindrical material engagement element device. FIG. 7A shows an embodiment including the material engagement element sheet (elements perpendicular) 16", and the temporary stabilizing material 66. This embodiment is equivalent to the configuration shown in FIG. 5E, and the embodiment shown in FIG. 7A has been processed as shown in FIGS. 1A-5D in a manner equivalent to the processing of the embodiment shown in FIG. 5E. FIG. 7B is a close up hidden lines visible view of the embodiment in FIG. 7A showing the temporary stabilizing material 66, and the material engagement element sheet (elements perpendicular) 16". As is made clear by the figure, the material engagement element distal ends 30 are embedded in the temporary stabilizing material 66 while the material engagement element proximal ends 32 remain free of the temporary stabilizing material 66. FIG. 7C shows the embodiment of FIGS. 7A and 7B: the temporary stabilizing material 66 and the material engagement element sheet (elements perpendicular) 16", and a cylindrical mandrel 80 the surface of which is covered with a temporary adhesive 82. FIG. 7C shows applied force lines 50d which indicate the directions of force applied to the embodiment shown in FIGS. 7A and 7B in order to conform the surface 84 of the temporary stabilizing material 66 to the surface 86 of the cylindrical mandrel 80. FIG. 7D shows the embodiment from FIGS. 7A and 7B with the surface 84 of the temporary stabilizing material 66 coincident with the surface 86 of the cylindrical mandrel 80. Surface 84 and surface 86 are held together by the temporary adhesive 82. The temporary adhesive 82 may be any weak adhesive such as a pressure sensitive adhesive. In yet another embodiment of the temporary adhesive 82, surface 84 and surface 86 may be held together by a mechanical means such as a vacuum. Also shown in FIG. 7D is the sheet material 10 which is outside of the material engagement element slots 14. FIG. 7E shows the embodiment of FIG. 7D with the sheet material 10 which was outside of the material engagement element slots 14 removed leaving the material engagement element proximal ends 32 exposed. The removal of the sheet material 10 which was outside of the engagement element patterned slots 14 may be accomplished through laser cutting, mechanical cutting, or any other suitable cutting method. FIG. 7F is a cross section view of the embodiment shown in FIG. 7E showing the material engagement elements in perpendicular state 20", the temporary stabilizing material 66, and the cylindrical mandrel 80. The material engagement element distal ends 30 point toward the cylindrical mandrel axis 88, and the material engagement element proximal ends 32 remain exposed. In this configuration the material engagement element proximal ends 32 may be encapsulated in flexible base material 76 in a manner such that the flexible base material 76 is contiguous. FIG. 7G shows the bottom cylindrical mold 90 and the bottom cylindrical mold cavity 92. FIG. 7H shows the embodiment from FIGS. 7E and 7F having the elements in perpendicular state 20", the temporary stabilizing material 66, and the cylindrical mandrel 80 inserted into the bottom cylindrical mold cavity 92 of the bottom cylindrical mold 90. FIG. 7I is identical to FIG. 7H with exception of the addition of the top cylindrical mold (shown in cut away view), which incorporates the top cylindrical mold cavity 96. Also, barrier material 71 has been applied to the surface of the temporary stabilizing material 66. FIG. 7J is identical to FIG. 7I with the exception that flexible base material 76 has been molded onto the bottom cylindrical mold cavity 92 and the top cylindrical mold cavity 96. The flexible base material 76 encapsulates the material engagement element proximal ends 32 in a contiguous manner as it is molded. FIG. 7K shows the embodiment for a cylindrical material engagement element device including the flexible base material 76, the temporary stabilizing material 66, the cylindrical mandrel 80, and (hidden from view) the material engagement elements in a perpendicular state 20". The embodiment shown in FIG. 7K has been removed from the bottom cylindrical mold 90 and the top cylindrical mold 94. FIG. 7L shows the embodiment of FIG. 7K with applied forces 50e being used in order to peel the cylindrical material engagement element device having the flexible base material 76, the temporary stabilizing material 66, and (hidden from view) the material engagement elements in perpendicular state 20" off of the cylindrical mandrel 80. FIG. 7M is FIG. 7L from a different perspective. FIG. 7M shows that as the cylindrical material engagement element device having flexible base material 76, the temporary stabilizing material 66, and the material engagement elements in perpendicular state 20' (hidden from view) is peeled off of the cylindrical mandrel 80, the cylindrical material engagement element device is inverted. As shown in FIG. 7M, as the embodiment is peeled off the order of the materials with regard to their distance from the cylindrical axis 88 is reversed. In the section 98 which has not been peeled, the temporary stabilizing material 66 is closest to the cylindrical axis 88 and the flexible base material 76 is farthest from cylindrical axis 88. In the peeled section 100, the order is inverted that is to say that the flexible base material 76 is closest to the cylindrical axis 88, and temporary stabilizing material 66 is the farthest from the cylindrical axis 88. FIG. 7N shows the cylindrical material engagement element device having the temporary stabilizing material 66, the flexible base material 76, and (hidden from view) the elements in perpendicular state 20" after it has been peeled off of the cylindrical mandrel 88 and inverted. FIG. 7O is a hidden lines shown cross section of FIG. 7N showing the temporary stabilizing material 66, the flexible base material, and the elements in perpendicular state 20". When FIG. 7O is compared to FIG. 7F, it may be seen that in FIG. 7O the material engagement element distal tips 30 now point away from the center of the cylindrical axis formed by the temporary stabilizing material 66 and the flexible base material 76. FIG. 7P is the embodiment of the cylindrical material engagement element device shown in FIG. 7N after the temporary stabilizing material 66 has been removed, this leaving the flexible base material 76 and the engagement elements in perpendicular state 20". The embodiment shown in FIG. 7P is the completed cylindrical material engagement element device 104. FIG. 7Q is yet another embodiment 105 of the cylindrical material engagement element device wherein the flexible base material 76 is configured as a balloon. The flexible base material 76 incorporates tapered sections 103, the forms for which would be incorporated into a cylindrical balloon bottom and top mold assembly. Other than the addition of the tapered sections, the methods used to create the embodiment 105 in FIG. 7Q would be identical to those used to create the cylindrical material engagement element device 104 shown on FIG. 7P.

Figure 8A:
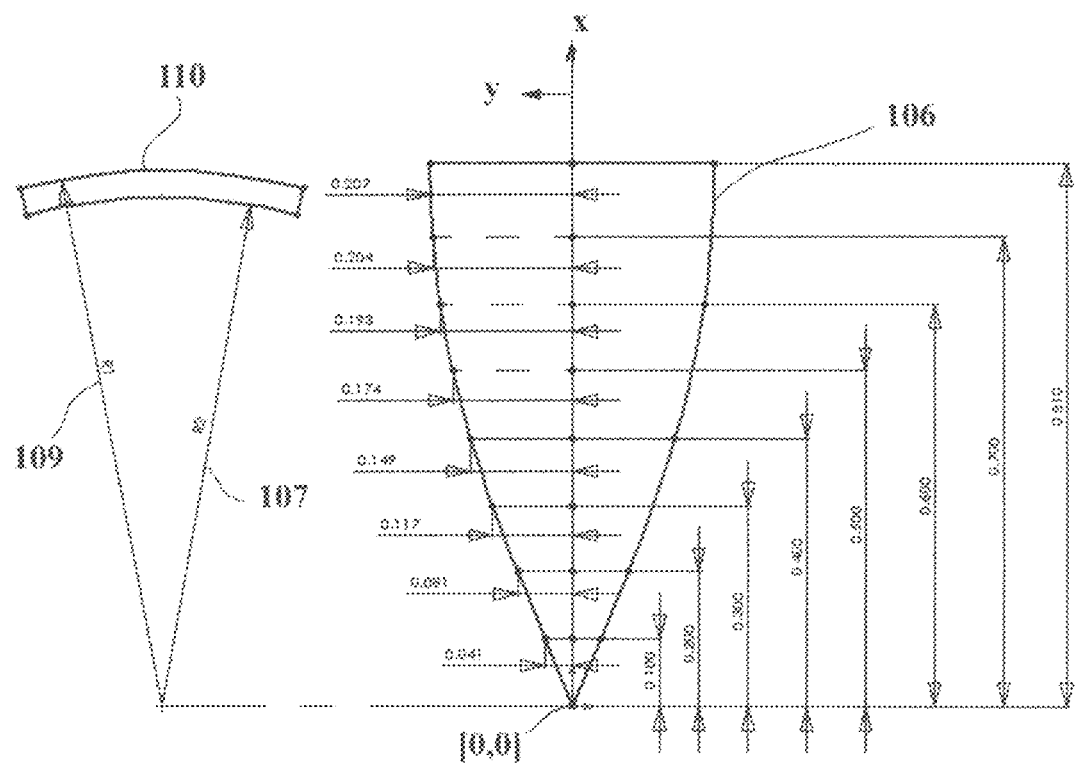
FIG. 8A shows a spherical gore profile with numerical values and the profile of a spherical material engagement element slot.
Figure 8B:
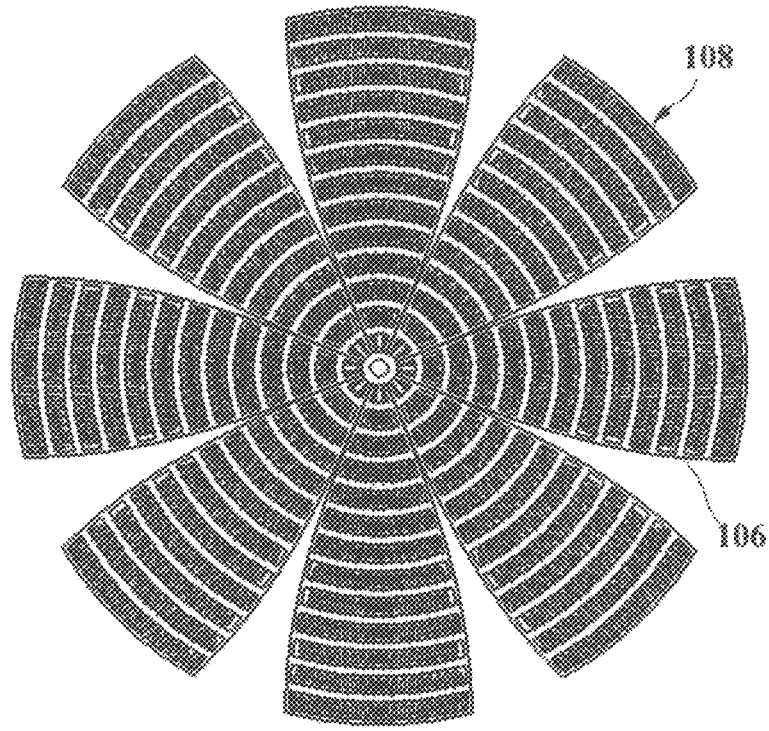
FIG. 8B shows a spherical material engagement element sheet formed with 8 gore profiles.
Figure 8C:
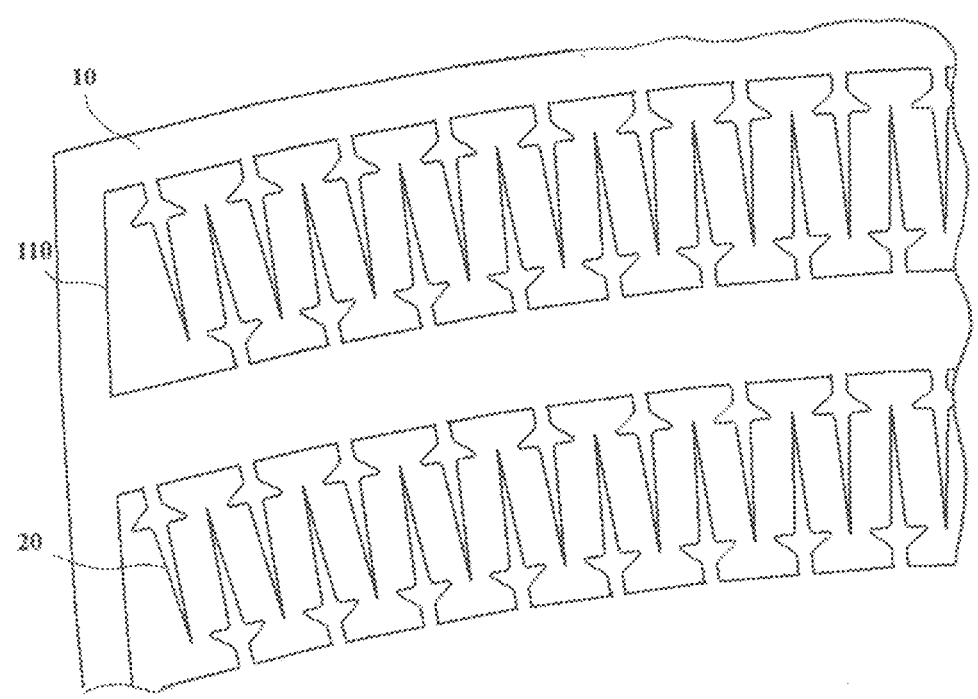
FIG. 8C is an enlarged view of FIG. 8B, showing material engagement elements and spherical material engagement element slots.

In PCT/US09/57348 FIG. 8A and paragraph 71 describe a spherical balloon comprised of flexible base material and an array of engagement elements, a configuration which will hereto be referred to as a spherical material engagement element device. The methods discussed herein detail the manufacture of a spherical material engagement element device. Globe makers frequently use mathematical devices called gores in order to map topographical data displayed on a flat surface into date that may be displayed onto the surface of a sphere. The mathematical formula for a gore is shown below:

$$y = \pm r * \tan\frac{\varphi}{2} * \sin\frac{x}{r} \quad (1)$$

Where r is the radius of the sphere, φ is the angle of the gore, and x varies from 0 to ¼ the circumference of the sphere or ½*π*r. FIG. 8A shows numerical values for x and y in the above gore equation using the following values: sphere diameter=1" (r=0.5"), and φ=45° which means that there a total of 365°/45°=8 gores. FIG. 8A also shows a gore profile 106, and the profile of a spherical material engagement element slot 110. As may be seen in FIG. 8A, the upper and lower profiles of the spherical material engagement element slot 110 are created using their radial distances (radial dimension 109 and radial dimension 107 respectively) from the origin [0,0] of the gore profile 106 shown in FIG. 8A. FIG. 8B shows a frontal view of spherical material engagement element sheet 108 with 8 gore profiles 106 cut using the gore formula (1) and the above parameters. The number of gores in a in a spherical material engagement element sheet 108 can range from 4 to 12. FIG. 8C is a close up view of FIG. 8B showing the spherical material engagement element slots 112, the material engagement elements 20, and the sheet material 10. The sheet material 10 may be comprised of a single layer of shape memory alloy or shape memory polymer, or multiple layers of pre-strained shape memory alloys and/or shape memory polymers with distinguishable activation parameters, or any other suitable material or materials.

Figure 8D:
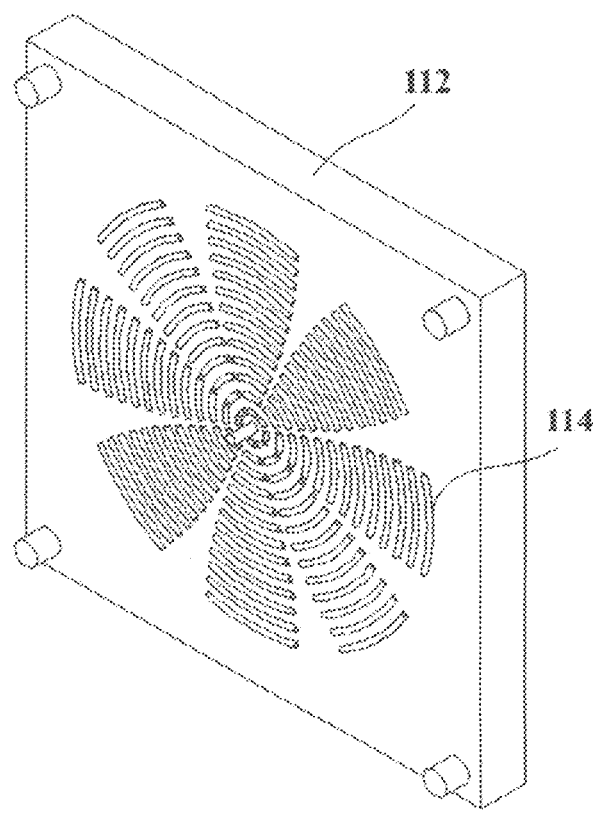
FIG. 8D shows a spherical bottom radius fixture.
Figure 8E:
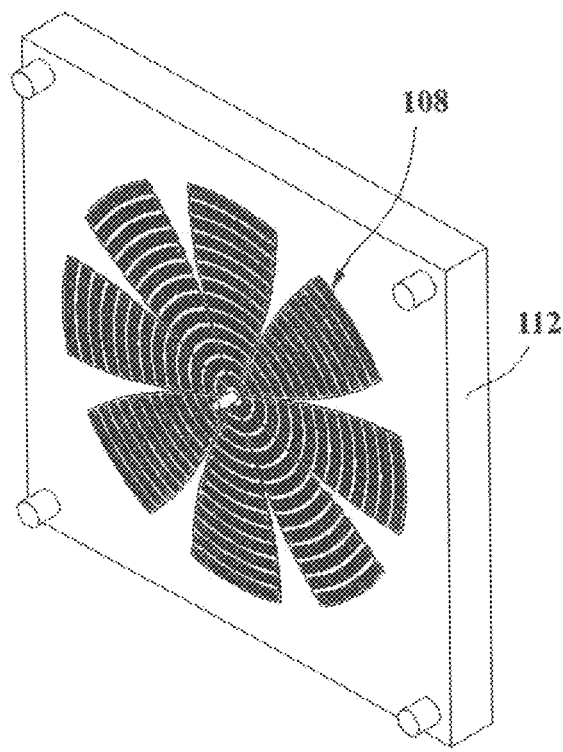
FIG. 8E shows the spherical bottom radius fixture of FIG. 8D with the spherical material engagement element sheet of FIG. 8B placed on it.
Figure 8F:
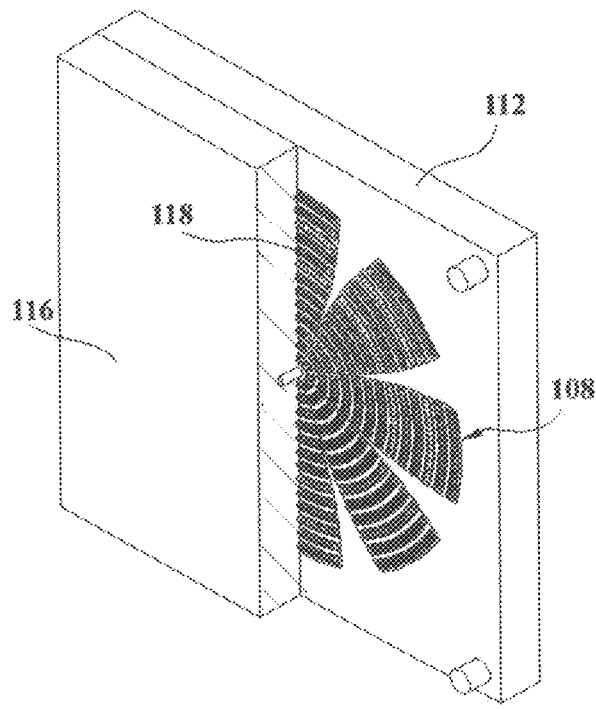
FIG. 8F illustrates the assembly of FIG. 8E with the addition of a spherical top radius fixture which is shown in section view and which is engaged with the spherical bottom radius fixture.
Figure 8G:
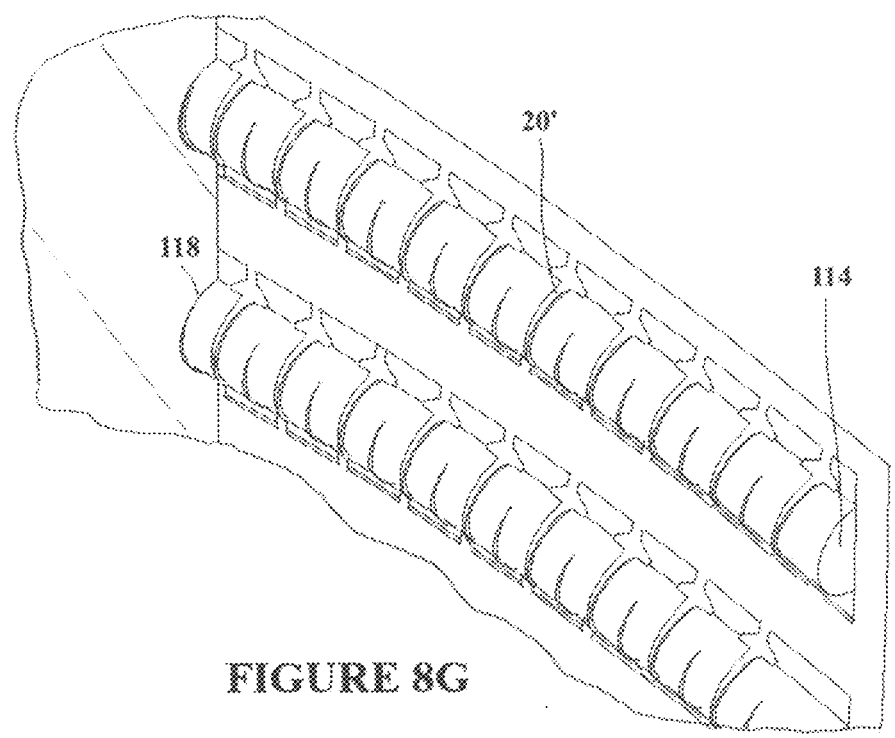
FIG. 8G is an enlarged view of FIG. 8F showing the material engagement elements configured in the engagement state.
Figure 8H:
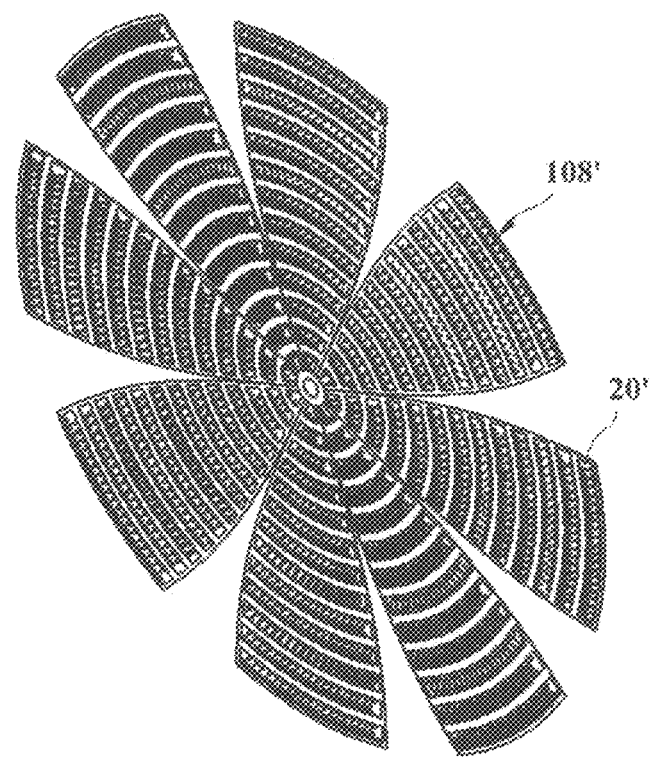
FIG. 8H shows the spherical material engagement element sheet with the elements in the engagement state.
Figure 8I:
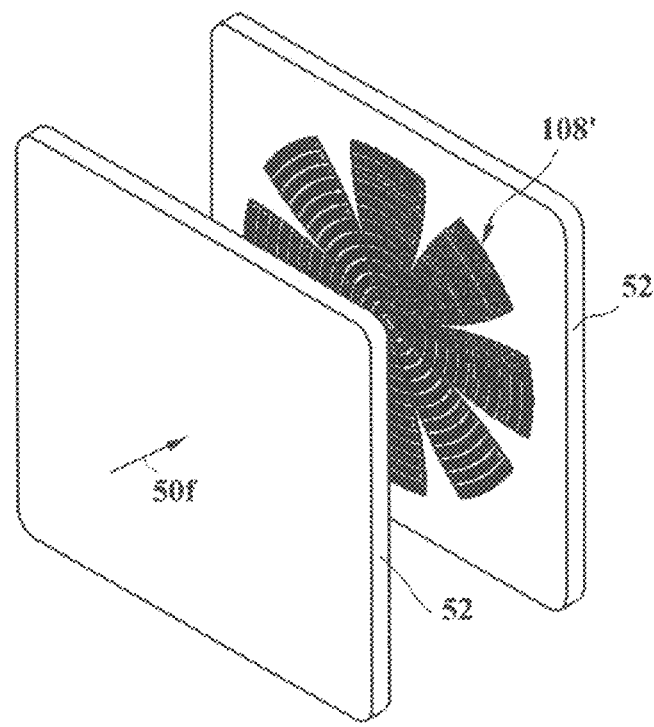
FIGS. 8I-8J depict the flattening of the spherical material engagement element sheet with the elements in the engagement state.
Figure 8J:
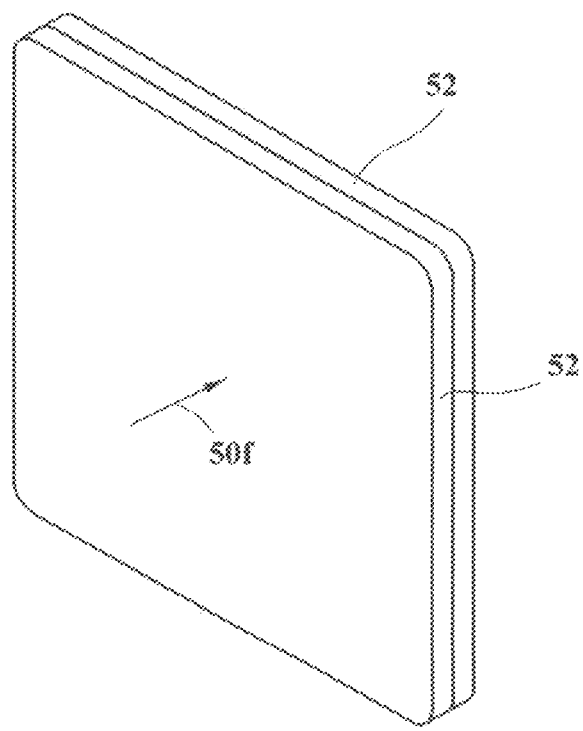
Figure 8K:
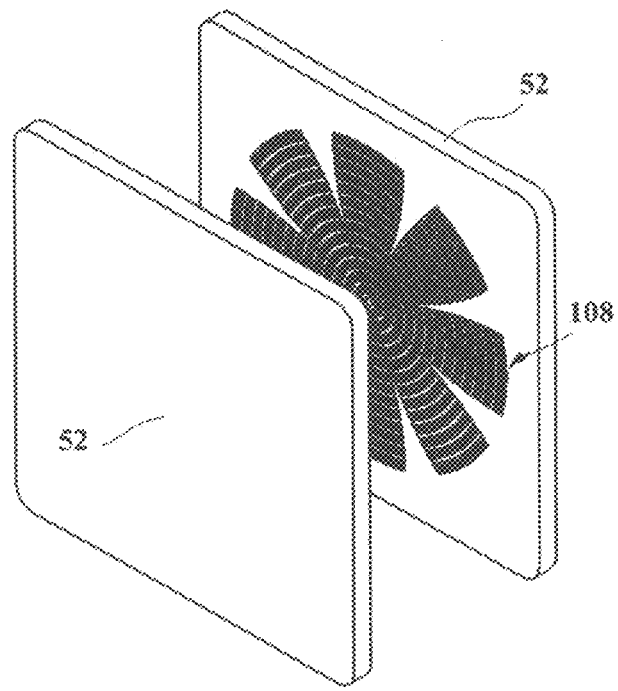
FIG. 8K depicts the flattened spherical material engagement element sheet with elements in the engagement state.

For some embodiments of the sheet material 10 such as a single sheet of shape memory alloy material, it may be desirable to shape set the material engagement elements 20 into material engagement elements in engagement state 20', and then return the material engagement elements to a flattened state 20. FIG. 8D depicts a spherical bottom radius fixture 112. The spherical bottom radius fixture 112 incorporates a pattern of spherical positive radii bosses 114, the profiles of which conform to the desired radii to be set into the material engagement elements 20. FIG. 8E shows the spherical material engagement element sheet 108 placed onto the spherical bottom radius fixture 112. The spherical material engagement element slots 112 are aligned with the spherical positive radii bosses 114. FIG. 8F shows a cut away view of the spherical top radius fixture 116 placed into position over the spherical bottom radius fixture 112. The spherical top radius fixture 116 incorporates a pattern of spherical radius slots 118, the profiles of which conform to the desired radii to be set into the material engagement elements 20. The spherical radius slots 118 have a profile defined by a radius r1 (see dimension 49 in FIG. 2D) within the range r1=W/(2*π) to r1=W/π where W is the width of the spherical material engagement element slot. The spherical positive boss radii bosses 114 have a profile defined by a radius r2 (see dimension 47 in FIG. 2D) the equation for which is r2=r1-t. The spherical top radius fixture 116 is forced down into contact with the spherical bottom radius 112 thus forming radii into the material engagement elements 20 exactly as shown in FIGS. 2D-2G. FIG. 8G is a close up view of the spherical positive radii bosses 114, the spherical radius slots 118, and the material engagement elements in the engagement state 20'. FIG. 8H shows the spherical engagement element patterned sheet (elements in engagement state) 108', and the engagement elements in engagement state 20'. FIG. 8I shows the spherical material engagement element sheet (elements in engagement state) 108', two flat plate fixtures 52, and an applied force 50*f* which forces the two flat plate fixtures 52 together as shown in FIG. 8J thus flattening the spherical material engagement element sheet (elements in engagement state) 108' as shown in FIG. 8K.

Figure 8L:
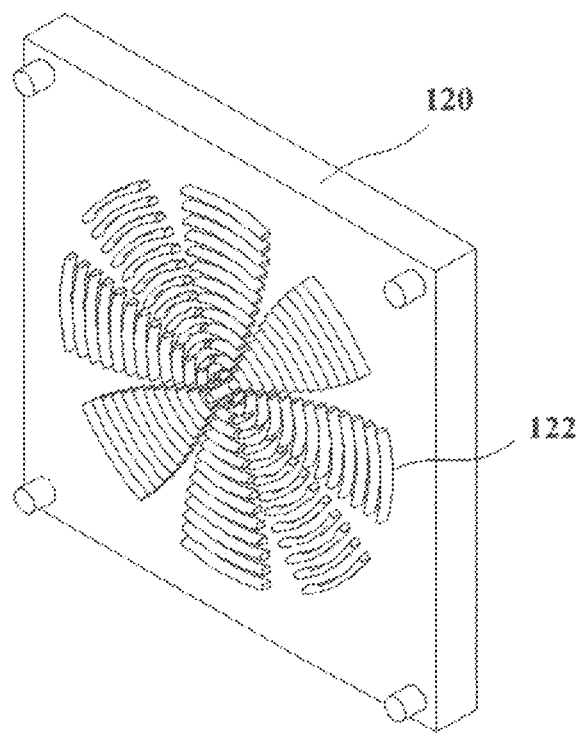
FIG. 8L shows a spherical bottom perpendicular fixture.
Figure 8M:
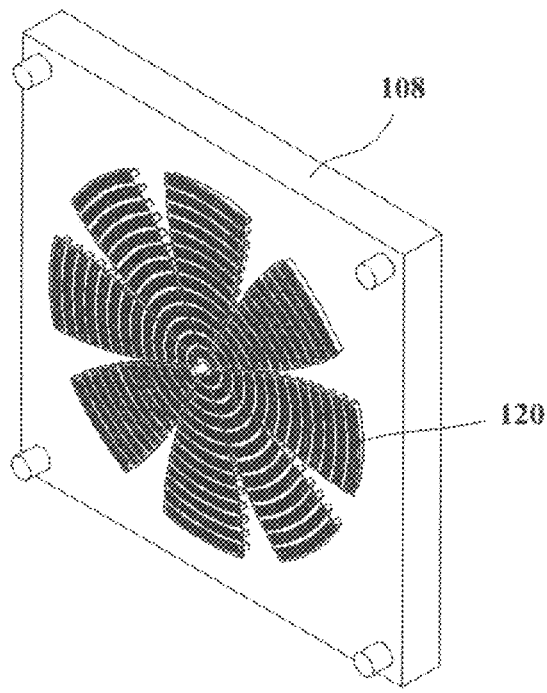
FIG. 8M shows the spherical material engagement element sheet on place over the spherical bottom perpendicular fixture of FIG. 8L.
Figure 8N:
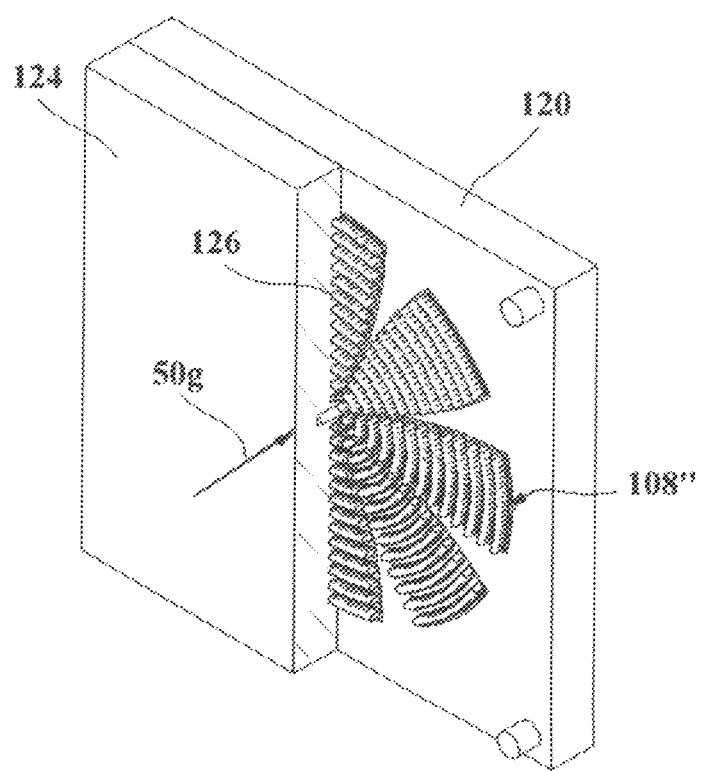
FIG. 8N illustrates the assembly of FIG. 8M with the addition of a spherical top perpendicular fixture which is shown in section view and which is engaged with the spherical bottom perpendicular fixture.
Figure 8O:
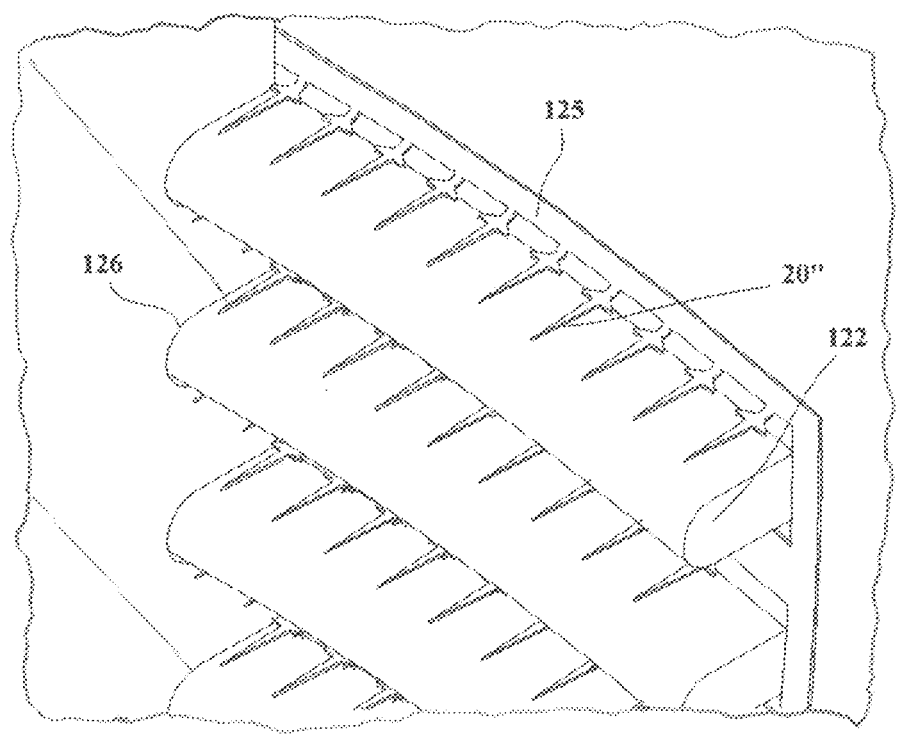
FIG. 8O is an enlarged view of FIG. 8N.

The material engagement elements 20 can now be manipulated such that they are in a state that is substantially perpendicular to the surface of the sheet material 10 of the spherical material engagement element sheet 108. FIG. 8L is a perspective view of a spherical bottom perpendicular fixture 120 which incorporates spherical positive perpendicular bosses 122. FIG. 8M shows the spherical material engagement element sheet 108 placed onto the spherical bottom perpendicular fixture 120. FIG. 8N shows the spherical top perpendicular fixture 124 (which incorporates spherical perpendicular slots 126) being forced into the spherical bottom perpendicular fixture 120 by an applied force 50*g*. This forces the material engagement elements 20 into perpendicular state 20" exactly as shown in FIGS. 4D and 4E thus creating the spherical material engagement element sheet (elements in perpendicular state) 108". The gap between the spherical positive perpendicular bosses 122 and the spherical perpendicular slots 126 is t the thickness of the sheet material just as shown in FIG. 4E. FIG. 8O is a close up of FIG. 8N showing the spherical positive perpendicular bosses 122, the spherical perpendicular slots 126, surface 125, and the material engagement elements in a perpendicular state 20".

Figure 9B:
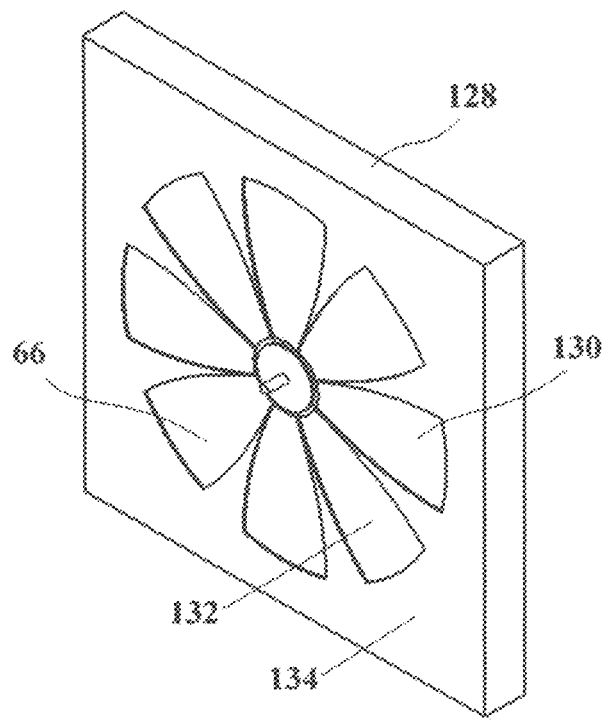
FIG. 9B shows the spherical flat mold fixture of FIG. 9A partially filled with a temporary stabilizing material.
Figure 9C:
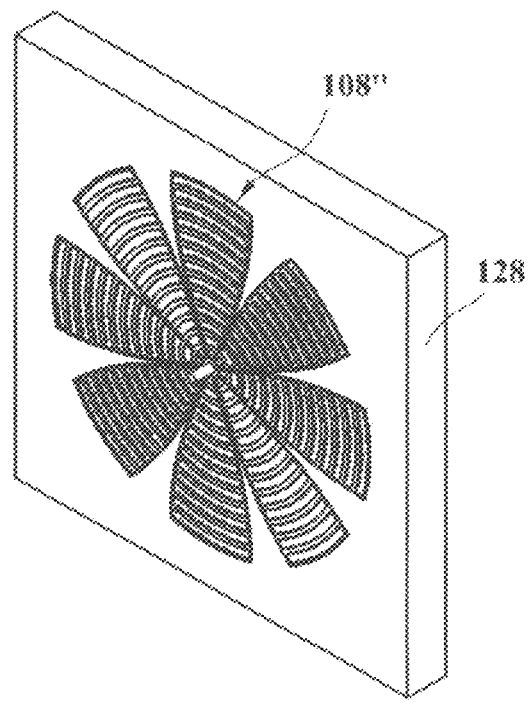
FIG. 9C shows the assembly of FIG. 9B with a spherical material engagement element sheet with the elements in the perpendicular state deployed into the temporary stabilizing material.
Figure 9D:
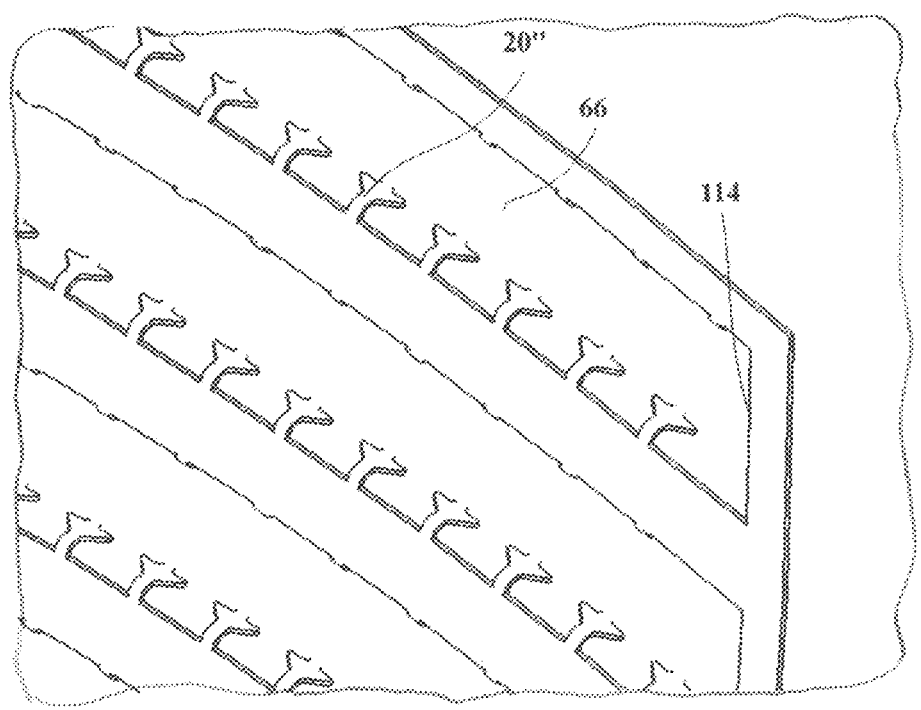
FIG. 9D is an enlarged view of FIG. 9C showing the material engagement elements in the perpendicular state partially deployed into the temporary stabilizing material.
Figure 9E:
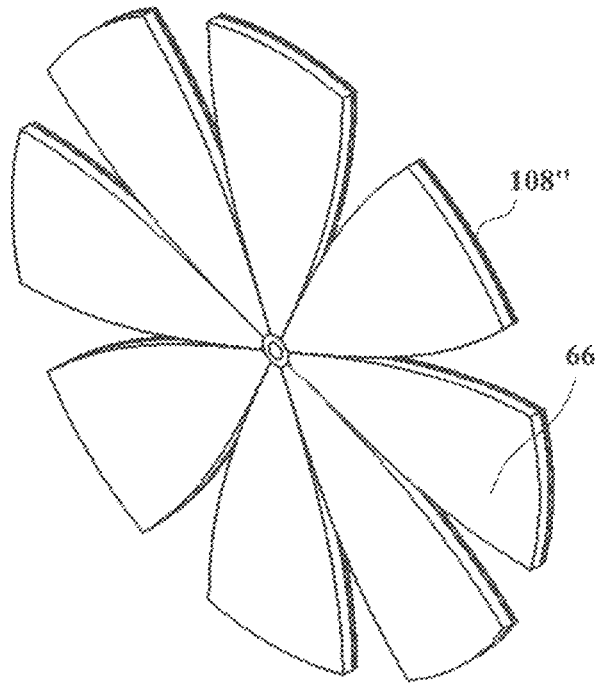
FIGS. 9E and 9F show the assembly comprised of the spherical material engagement element sheet with the elements in the perpendicular state and the temporary stabilizing material removed from the spherical flat mold fixture.
Figure 9F:
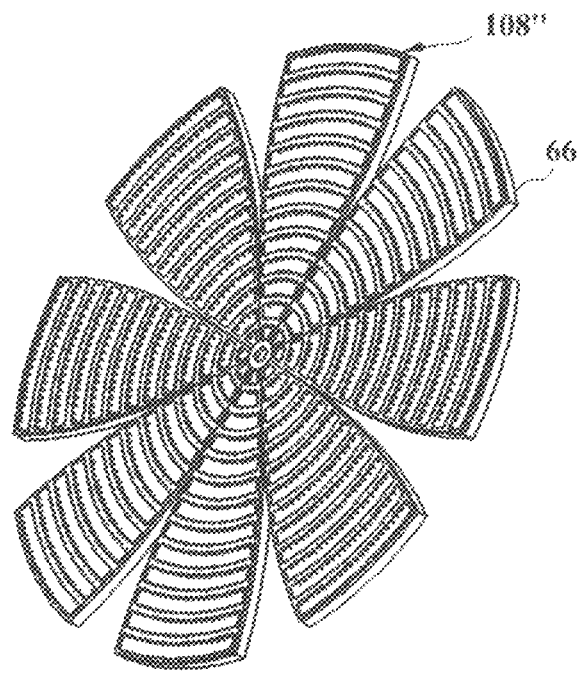
Figure 9G:
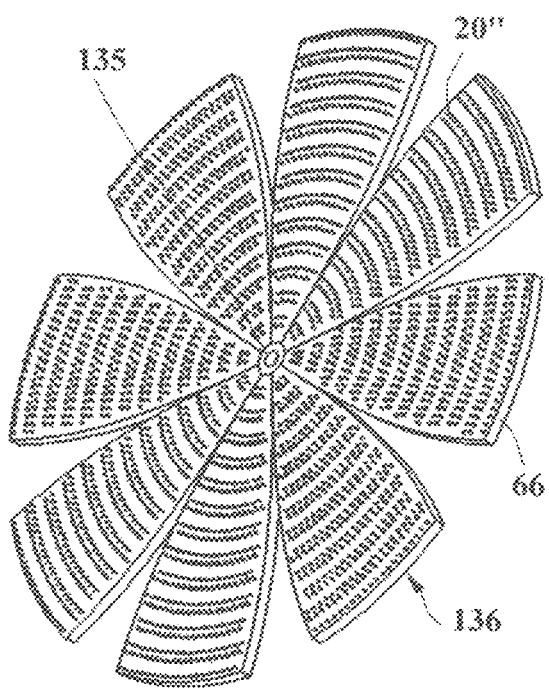
FIG. 9G shows the assembly of FIGS. 9E and 9F with the excess sheet material trimmed.
Figure 9H:
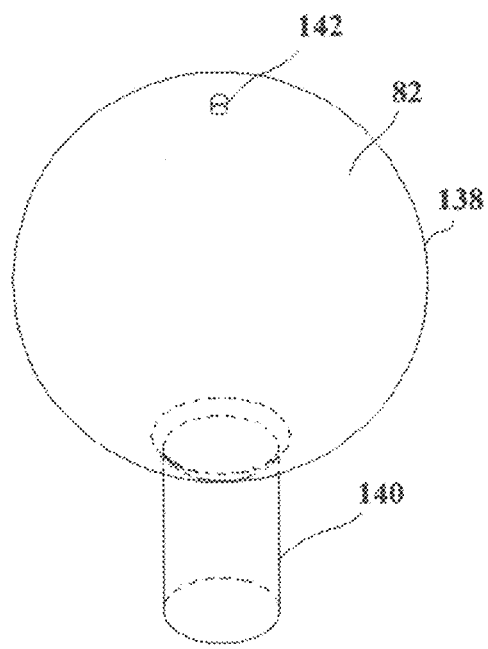
FIG. 9H shows a spherical mold.
Figure 9I:
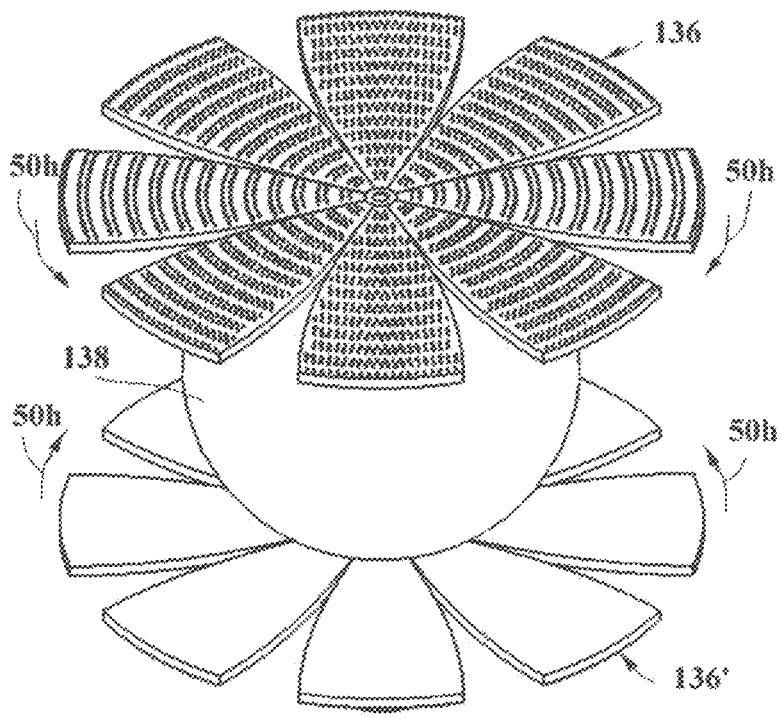
FIG. 9I shows the assembly of FIG. 9G and an assembly similar to it being applied to the surface of the spherical mold.
Figure 9J:
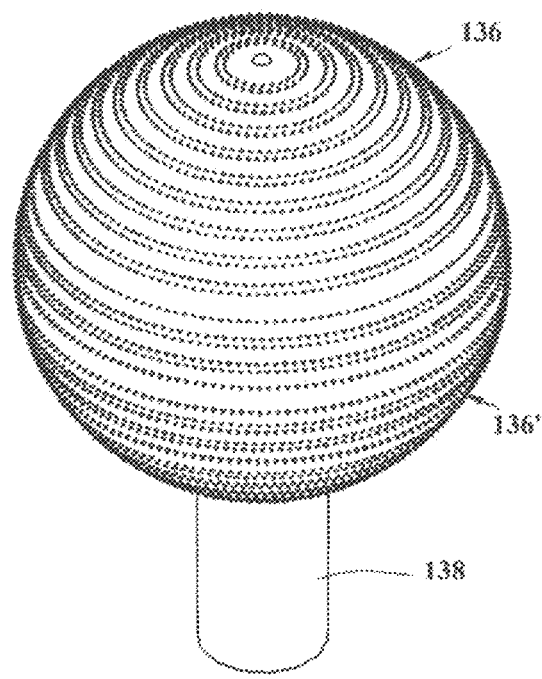
FIG. 9J shows the assembly of FIG. 9G and an assembly similar to it after the application to the spherical mold.
Figure 9K:
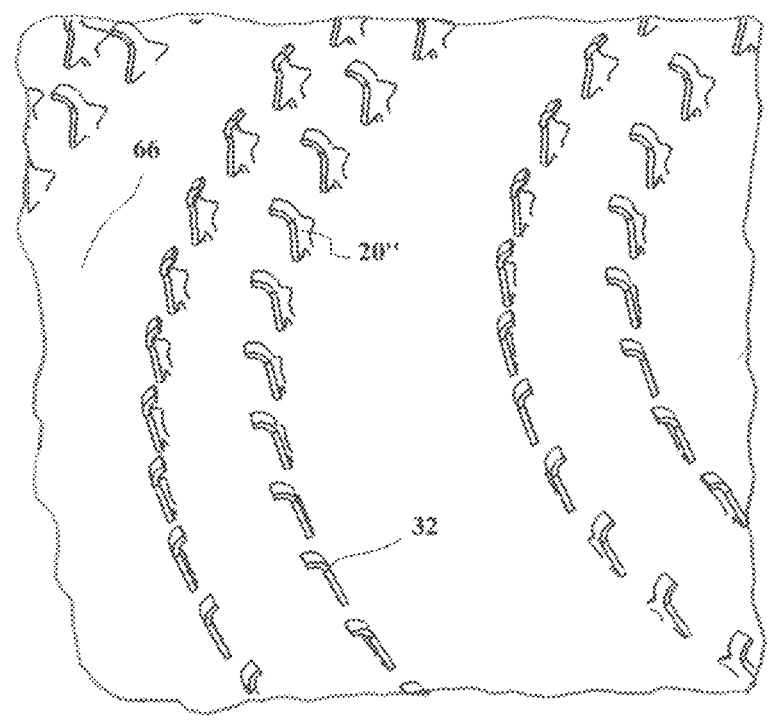
FIG. 9K is an enlarged view of FIG. 9J.
Figure 9L:
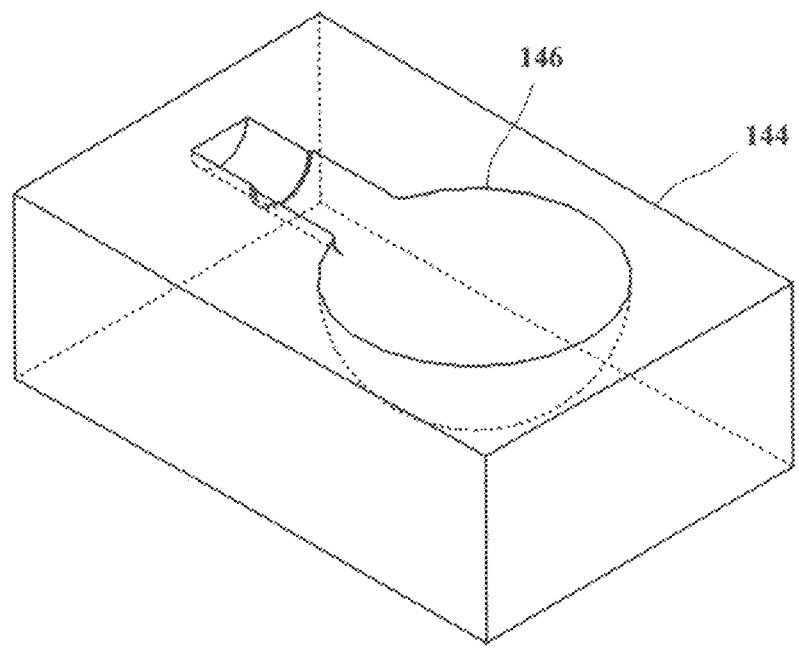
FIG. 9L shows a spherical bottom mold fixture.
Figure 9M:
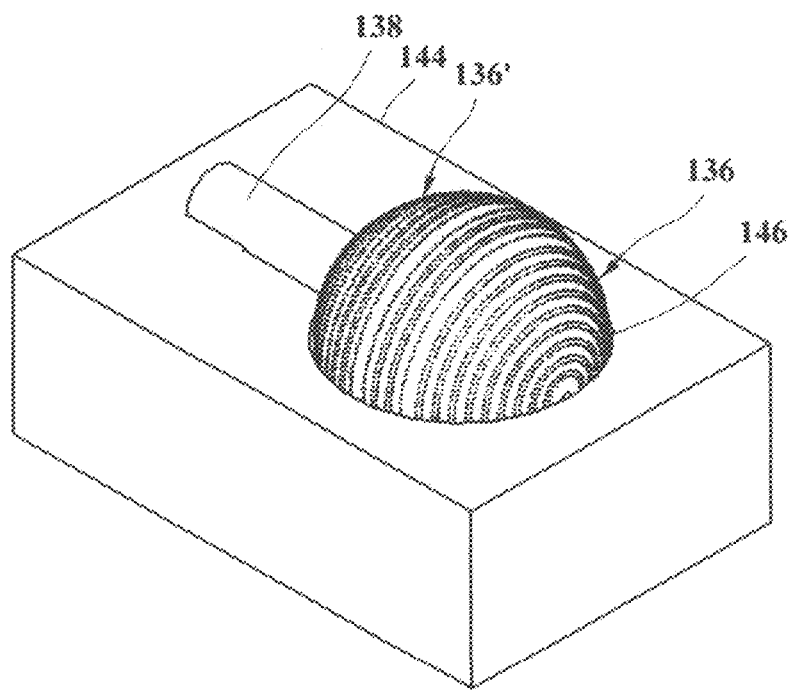
FIG. 9M shows the assembly from FIG. 9J inserted into the spherical bottom mold fixture.
Figure 9N:
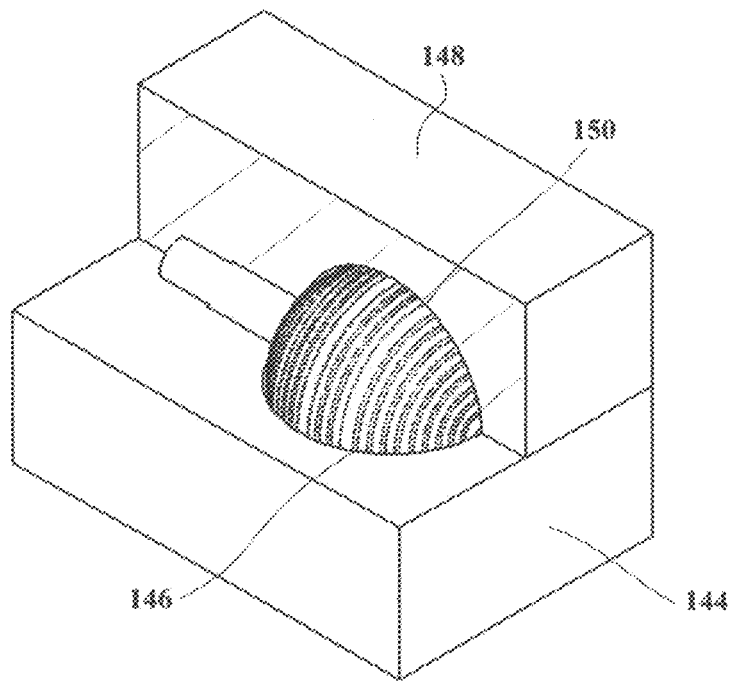
FIG. 9N illustrates the assembly of FIG. 9M with the addition of a spherical top mold fixture which is shown in section view and which is engaged with the spherical bottom mold fixture.
Figure 9O:
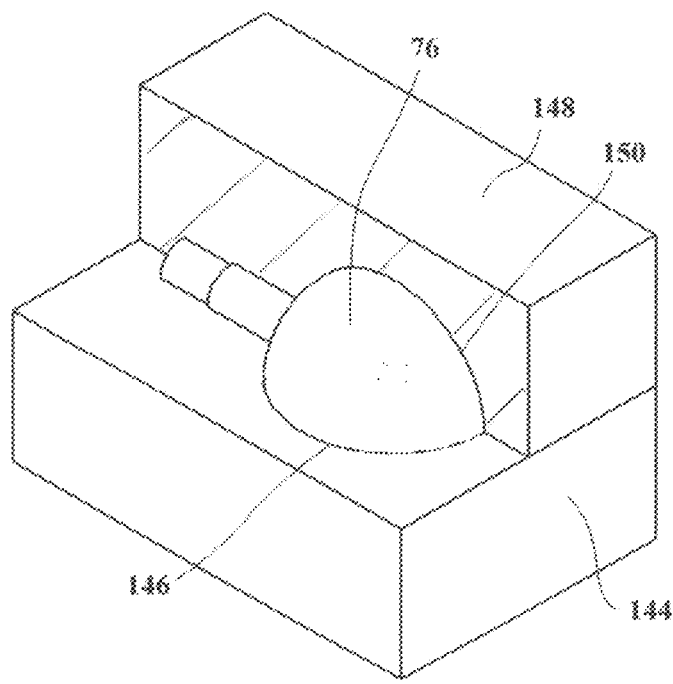
FIG. 9O shows the assembly of FIG. 9N with flexible base material molded into the bottom spherical flexible base material mold cavity and top spherical flexible base material mold cavity.
Figure 9P:
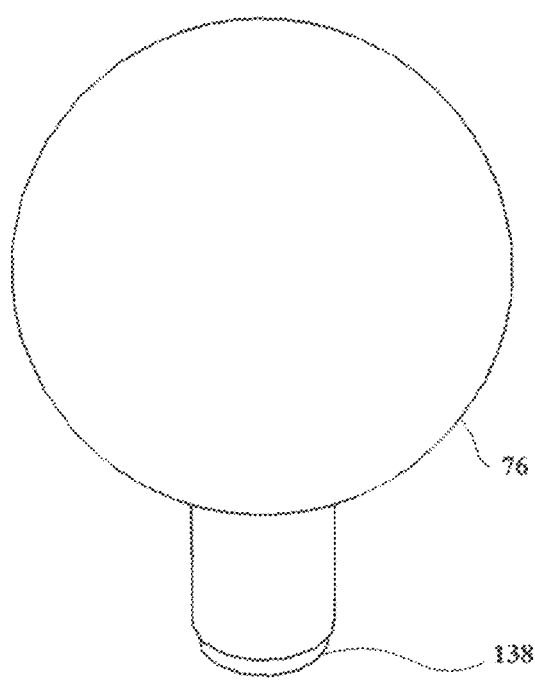
FIG. 9P shows the assembly comprised of the material engagement elements in the perpendicular state, the temporary stabilizing material, the flexible base material, and the spherical mold.
Figure 9Q:
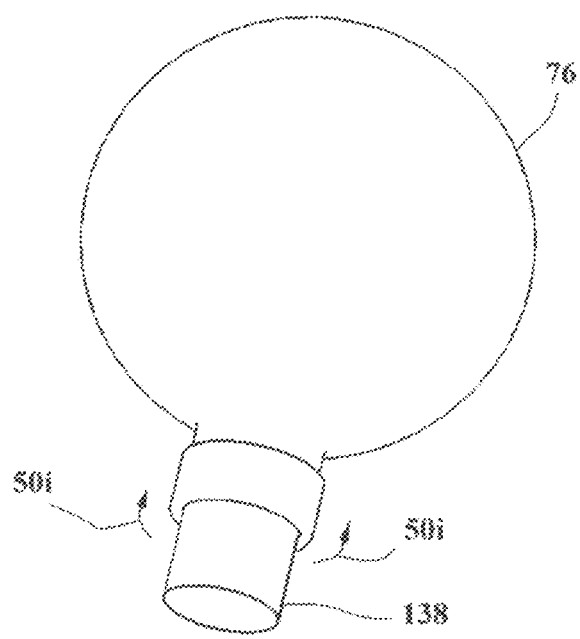
FIG. 9Q shows assembly comprised of the material engagement elements in the perpendicular state, the temporary stabilizing material, and the flexible base material being removed and inverted from the spherical mold.
Figure 9R:
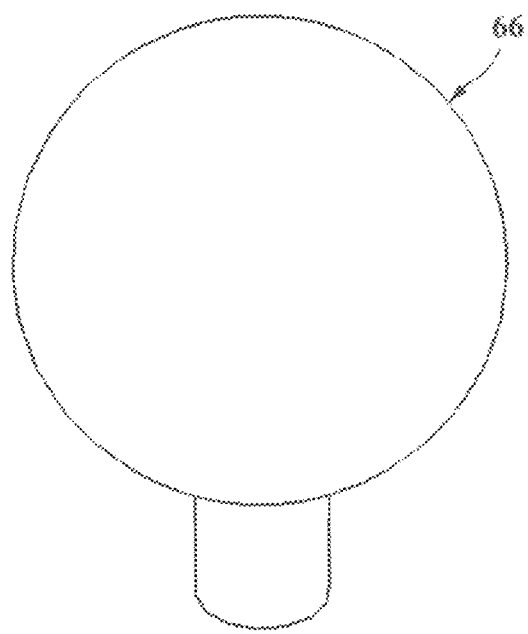
FIG. 9R shows the assembly comprised of the material engagement elements in the perpendicular state, the temporary stabilizing material, and the flexible base material.
Figure 9S:
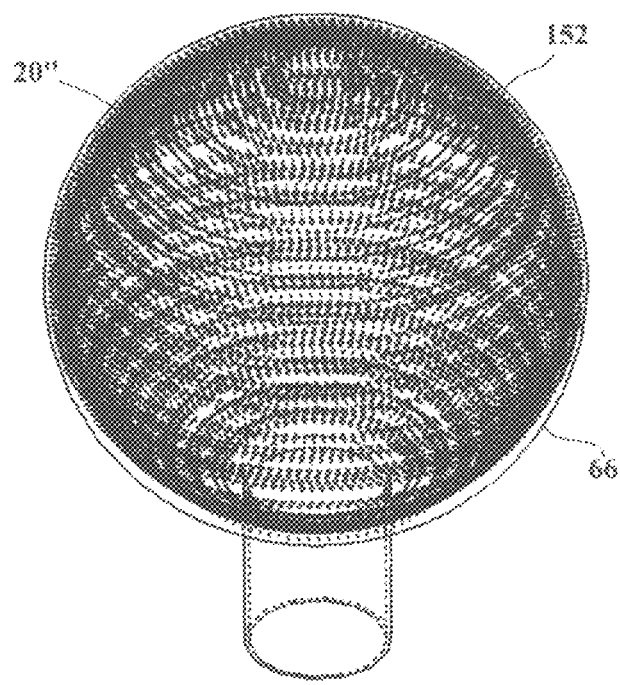
FIG. 9S is a hidden lines shown view of FIG. 9R showing the material engagement elements in a perpendicular state.
Figure 9T:
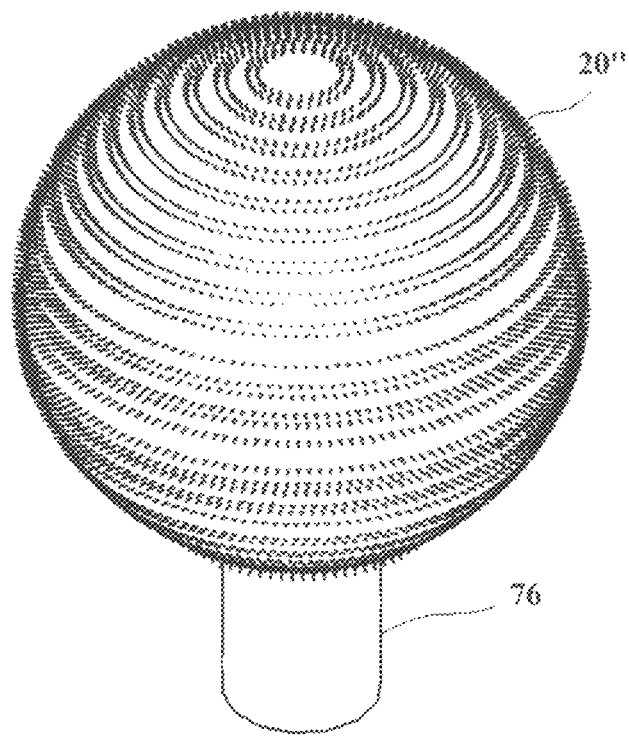
FIG. 9T shows the assembly from FIG. 9S after the temporary stabilizing material had been removed thus leaving the spherical material engagement element device.
Figure 9U:
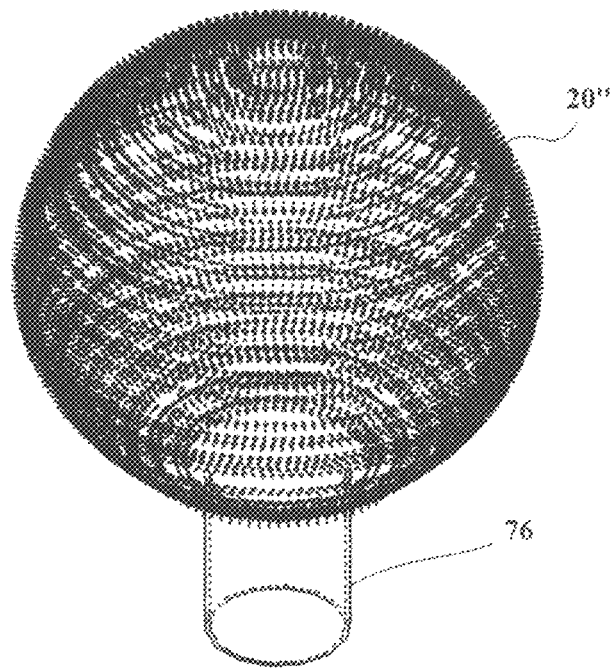
FIG. 9U is a hidden lines view of FIG. 9T the spherical material engagement element device.
Figure 9V:
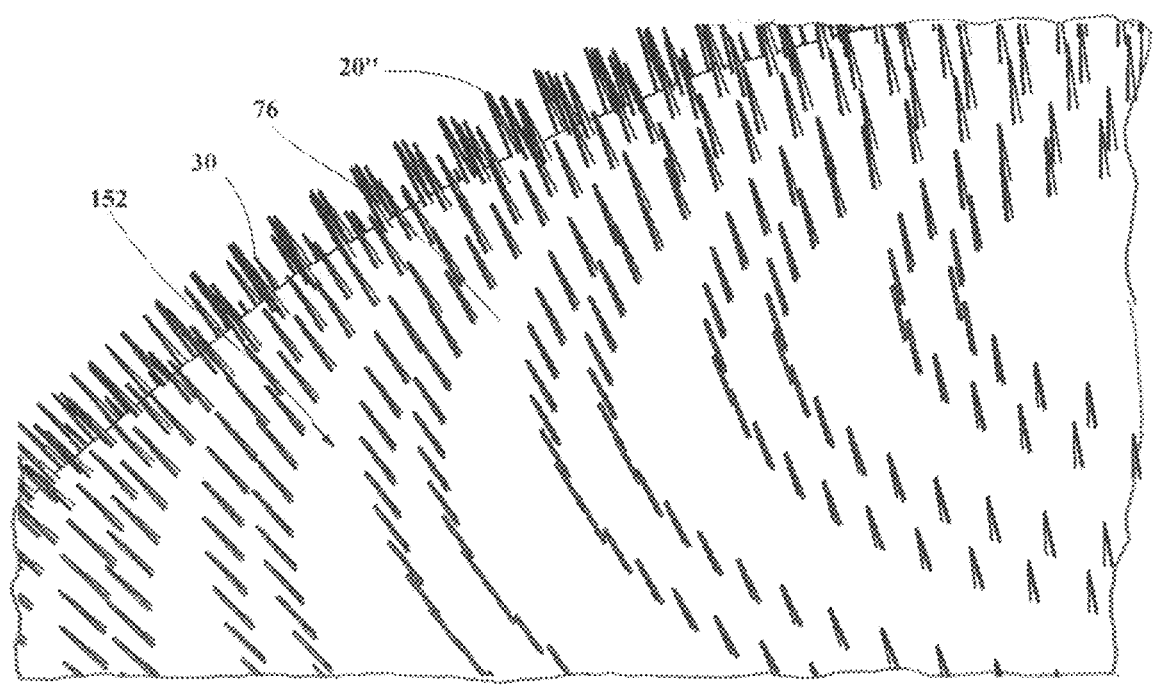
FIG. 9V is an enlarged view of FIG. 9T.

The spherical material engagement element sheet (elements in perpendicular state) 108" can now be appropriately inserted into a suitable configuration of temporary stabilizing material 66. FIG. 9A is a perspective view of a spherical flat mold fixture 128 which incorporates spherical temporary stabilizing material cavities 130. FIG. 9B shows the temporary stabilizing material 66 partially filling the spherical temporary stabilizing material cavities 130 of the spherical flat mold fixture 128. The spherical temporary stabilizing material cavities 130 are partially filled with the temporary stabilizing material 66, that is there is a gap between the upper surface 132 of the temporary stabilizing material 66, and the upper surface 134 of the spherical flat mold fixture 128. FIG. 9C shows the spherical material engagement element sheet (elements in perpendicular state) 108" inserted into the temporary stabilizing material 66. Surface 125 (shown in FIG. 8O) of the spherical material engagement element sheet (elements in perpendicular state) 108" is coincident with surface 134 of the spherical flat mold 128. FIG. 9D is a close up view of FIG. 9C showing the spherical material engagement element slots 114, and the material engagement elements in perpendicular state 20" partially inserted into the temporary stabilizing material 66. FIG. 9E shows the embodiment comprised of the spherical material engagement element sheet (elements in perpendicular state) 108" and the molded temporary stabilizing material 66. FIG. 9F is a view of the rear of the embodiment shown in FIG. 9E comprised of the spherical material engagement element sheet (elements in perpendicular state) 108" and the molded temporary stabilizing material 66. FIG. 9G shows the embodiment of FIGS. 9E and 9F with the sheet material 10 which was outside of the spherical material engagement slots 110 trimmed off leaving the material engagement elements in a perpendicular state 20". FIG. 9G also shows a location hole 135 and the temporary stabilizing material 66. This embodiment will be referred to as configuration 136. The trimming of the sheet material 10 may be accomplished through laser cutting, mechanical cutting, or any other suitable means. FIG. 9H is a hidden lines view of a spherical mold 136 which incorporates the spherical mold base 140 and the location post 142. The surface of the spherical mold is covered with temporary adhesive 82. FIG. 9I shows the embodiment 136 placed over the spherical mold such that the position hole 135 is concentric with the spherical mold location post 142. The embodiment 136 is forced onto the upper surface of the spherical mold 138 by applied forces 50h. A configuration 136' identical to embodiment 136 except that the position hole 135' is large enough to encompass the spherical mold base 140 is similarly applied to the lower surface of the spherical mold 140 by applied forces 50h. FIG. 9J shows the spherical mold 138, and the upper and lower configurations 136 and 136' held into place by the temporary adhesive 82. FIG. 9K is a close up view of the surface of the embodiment shown in FIG. 9J showing the temporary stabilizing material 66, the material engagement elements in a perpendicular state 20", and the exposed material engagement element proximal ends 32. FIG. 9L is a hidden lines shown view if a bottom spherical mold fixture 144 which incorporates the bottom spherical flexible base material mold cavity 146. FIG. 9M shows the embodiment shown in FIG. 9J inserted into the bottom spherical flexible base material mold cavity 146. The embodiment for forming the spherical material engagement element device shown in FIG. 9J includes the spherical mold 138, and the upper and lower configurations 136 and 136'. FIG. 9N is identical to FIG. 9M with the exception of the addition of the top spherical mold fixture 148 (shown in cut away view) which incorporates the top spherical flexible base material mold cavity 150. FIG. 9O shows flexible base material 76 molded into the bottom spherical flexible base material mold cavity 146 and the top spherical flexible base material mold cavity 150 of the bottom spherical mold fixture 144 and the top spherical mold fixture 148. FIG. 9P is the spherical material engagement element device with the temporary stabilizing material 66 (hidden from view in the figure), the flexible base material 76, the material engagement elements in a perpendicular state 20" (hidden from view in the figure), and the spherical mold 138. FIG. 9Q shows the embodiment of the spherical material engagement element device with the temporary stabilizing material 66 (hidden from view in the figure), the flexible base material 76, and the engagement elements in a perpendicular state 20" (hidden from view in the figure) being removed from the spherical mold 138 by applied forces 50i. As may be seen from the figure, the spherical material engagement element device with the temporary stabilizing material 66 (hidden from view in the figure), the flexible base material 76, and the material engagement elements in a perpendicular state 20" (hidden from view in the figure) is inverted as it is removed from the spherical mold 138. This process is analogous to the removal process detailed in FIGS. 7L-7N for the cylindrical material engagement element device 104. FIG. 9R shows the embodiment for the spherical material engagement element device with the temporary stabilizing material 66, the flexible base material 76 (hidden from view in the figure), and the material engagement elements in a perpendicular state 20" (hidden from view in the figure) after it has been removed from the spherical mold 138 and inverted. FIG. 9S is a hidden lines shown view of the embodiment of FIG. 9R showing the temporary stabilizing material 66, the flexible base material 76, and the material engagement elements in a perpendicular state 20". FIG. 9T is the embodiment depicted in FIG. 9S after the removal of the temporary stabilizing material 66, thus leaving the spherical material engagement element device 152 which incorporates flexible base material 76 and material engagement elements in a perpendicular state 20". FIG. 9U is a hidden lines shown view of FIG. 9T. FIG. 9V is a close up view of the surface of the spherical material engagement element device 152 showing the material engagement elements in a perpendicular state 20", and the flexible base material 76. As can be seen in FIG. 9V, after the inversion process shown in FIG. 9Q the engagement material element distal ends 30 point away from the center of the spherical material engagement element device 152. Compare this to FIG. 9K which shows the material engagement element proximal ends 32 pointing away from the center of the spherical material engagement element device 152.

Figure 10A:
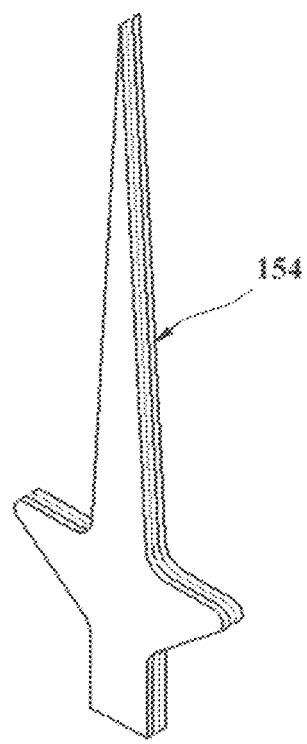
FIG. 10A is a perspective view of a deployable material engagement element.
Figure 10B:
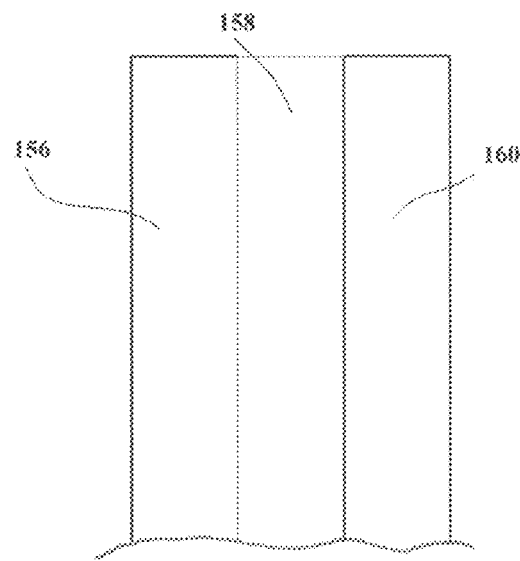
FIGS. 10B-10H depict the deployment and removal sequence for the deployable material engagement element.
Figure 10C:
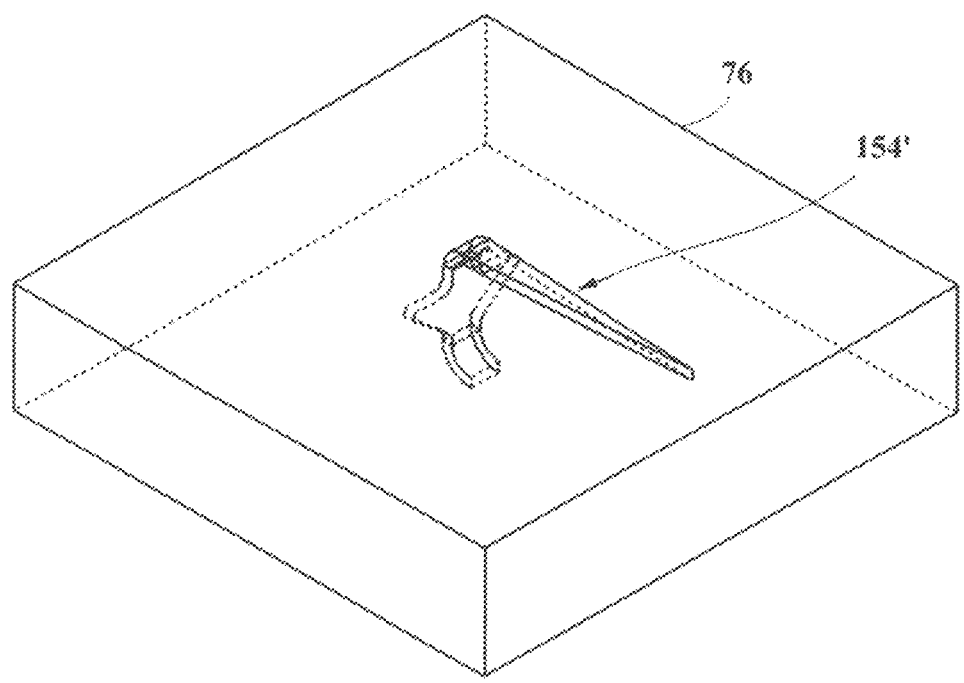
Figure 10D:
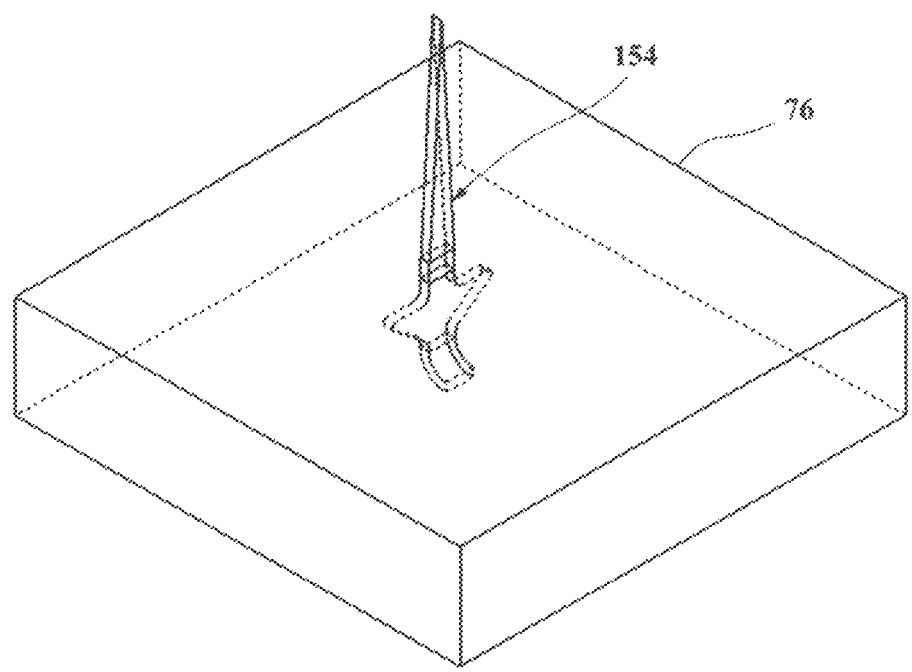
Figure 10E:
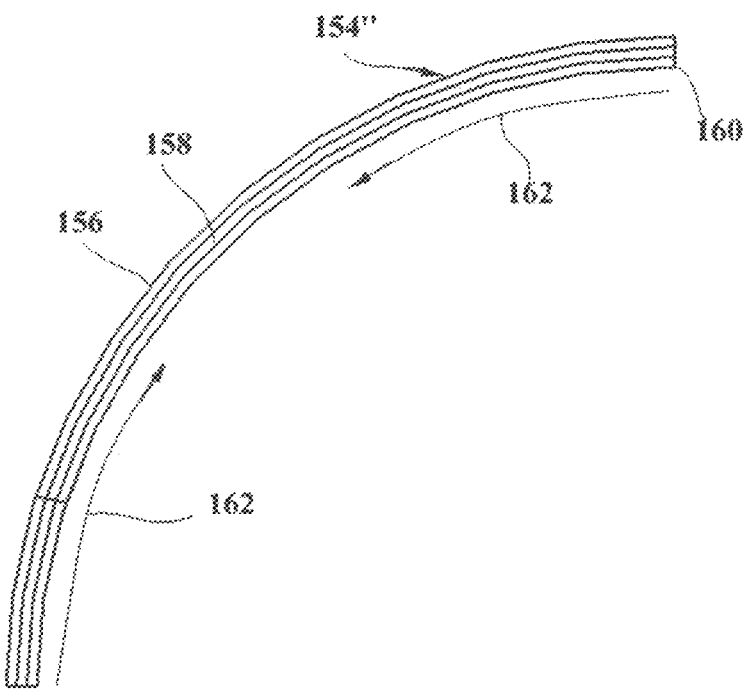
Figure 10F:
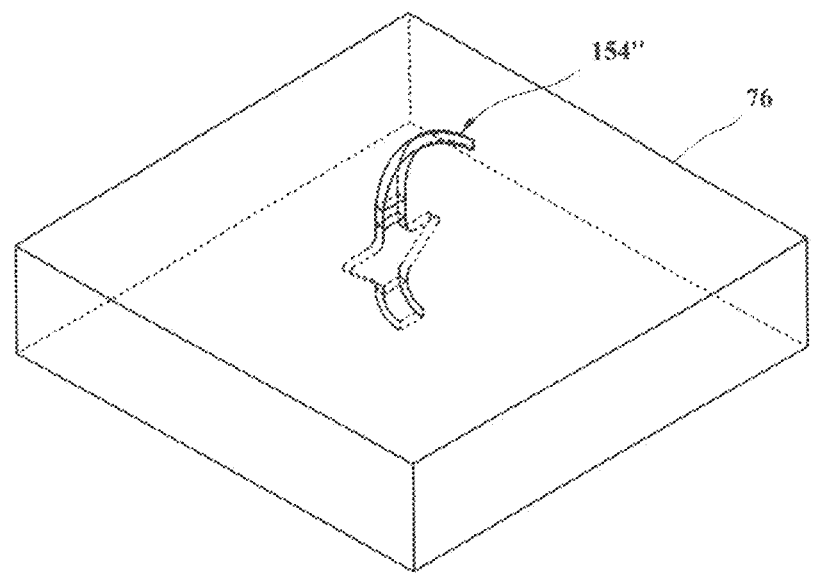
Figure 10G:
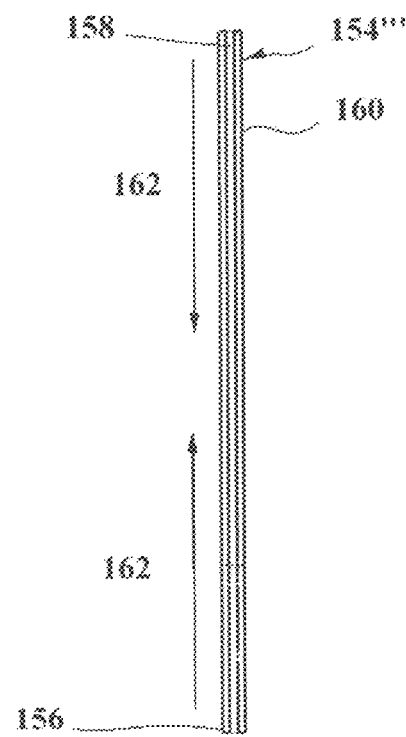
Figure 10H:
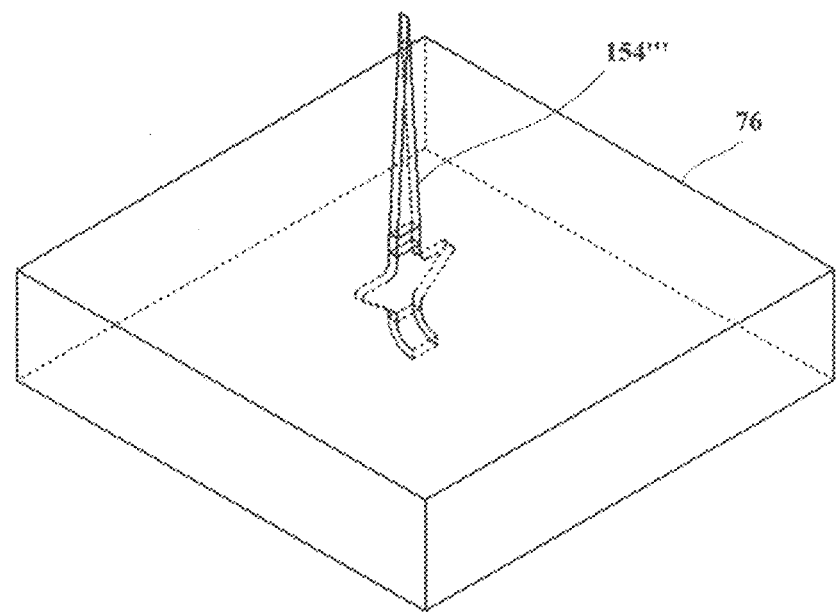

An embodiment of an material engagement element 20 that lies in close contact to the flexible base material 76 prior to the deployment of the given material engagement element device is disclosed hereafter. The material engagement element would assume a "deployment" state once the material engagement element device is ready to deploy. This embodiment would be advantageous when incorporated into material engagement element devices which are to be deployed into completely fluid environments. For example, a cylindrical material engagement element device 104 which is to be deployed into an artery which contains blood. FIG. 10A shows an embodiment of a deployable material engagement element 154. The deployable material engagement element 154 is cut from sheet material 10 that is comprised of multiple layers of materials. For example, the sheet material 10 could be comprised of multiple layers of shape memory materials with different activation parameters as described in PCT/US11/02802 FIGS. 7A-7E and paragraph 34. FIG. 10B shows a cross section view of the deployable material engagement element 154. The element is comprised of three layers, layer 156, layer 158, and layer 160. For this example it is assumed that layers 156 and 160 are pre-stressed shape memory polymers with different activation parameters. Layer 158 may be a shape memory alloy with a body temperature activation shape set in a straight configuration 154 as shown in FIG. 10A. FIG. 10C shows the deployable engagement element 154 in a state 154' such that it lies in close proximity to the flexible base material 76. FIG. 10B shows the deployable material engagement element 154 after the given material engagement element device had been deployed into a body temperature fluid environment thus transforming the deployable material engagement element 154 to its deployment state. The deployable material engagement element can then be transformed to its engagement state 154" through the activation of layer 160 as shown in FIG. 10E. FIG. 10E shows compression lines 162 which indicate the compression of the material 160 which cause the deflection of the deployable material engagement element to the state 154 as shown in FIG. 10F. Layer 156 may be activated as shown in FIG. 10G. Compression lines 162 indicate the compression of the material 156 thus deforming the deployable material engagement element to the state 154''' shown in FIGS. 10G and 10H allowing for the removal of the deployable material engagement element 154'''.

Figure 11A:
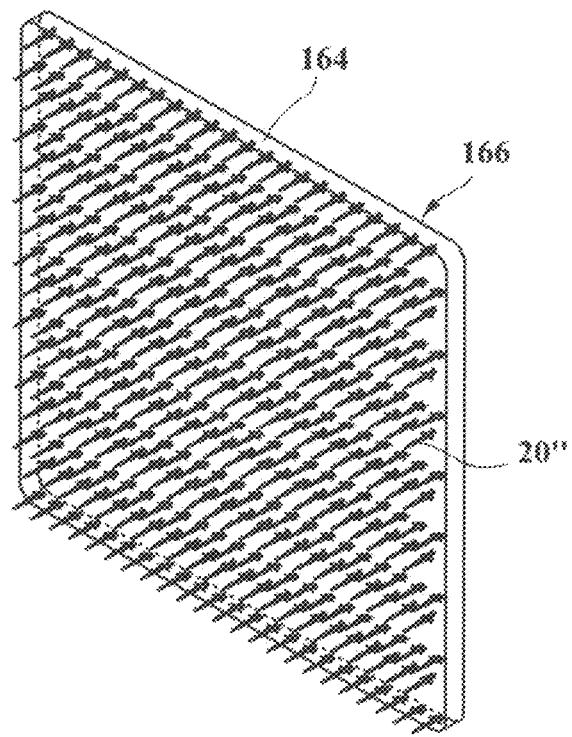
FIGS. 11A and 11B depict a material engagement element pad device with skin graft material replacing the flexible base material.
Figure 11B:
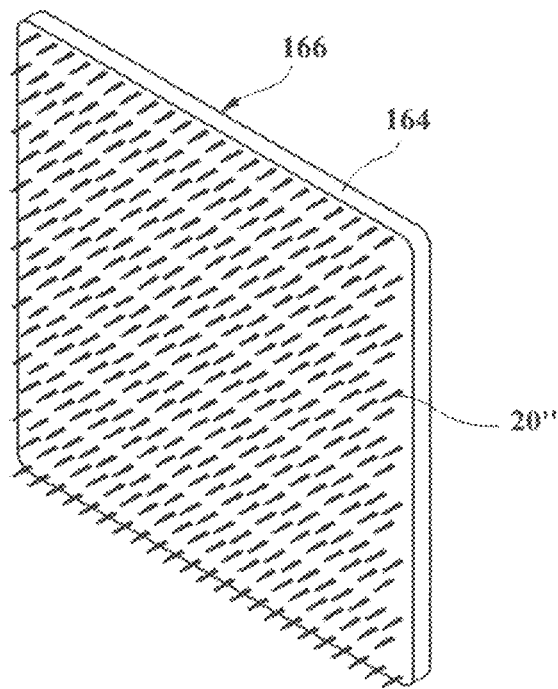

Embodiments of material engagement element devices wherein the flexible base material is comprised of skin graft material are disclosed hereafter. FIG. 11A is a hidden lines shown view of a material engagement element pad 166 incorporating material engagement elements in the perpendicular state 20", and skin graft material 164. The skin graft material 164 may be any of the following: autograft material, allogenic material, or any other suitable skin graft material. The tissue graft material could be cultured around any suitable configuration of material engagement element sheet with the engagement elements in perpendicular state 20". The use of any of these skin graft materials 164 as a replacement for the flexible base material 76 could thus be applied to material engagement element device configurations including the cylindrical material engagement element devices (FIGS. 7P and 7Q), the spherical material engagement element device (FIG. 9T), or any other suitable material engagement element device configuration.

Figure 12A:
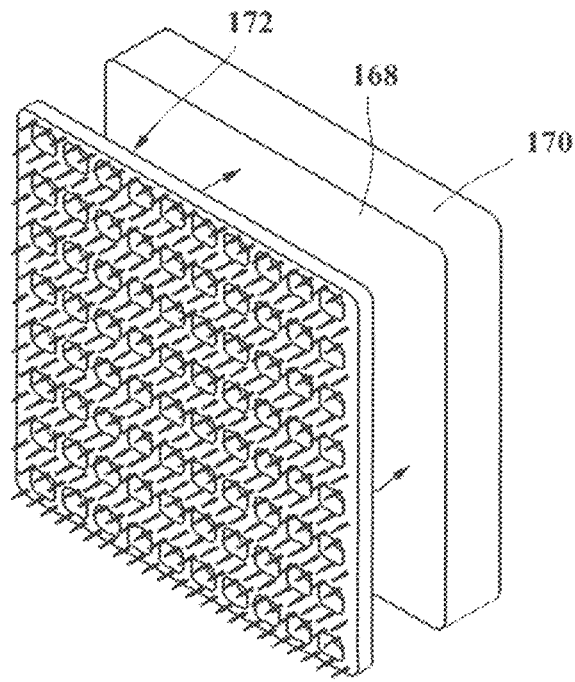
FIGS. 12A-12C depict a material engagement element pad device configuration used as an adhesive for a conventional bandage.
Figure 12B:
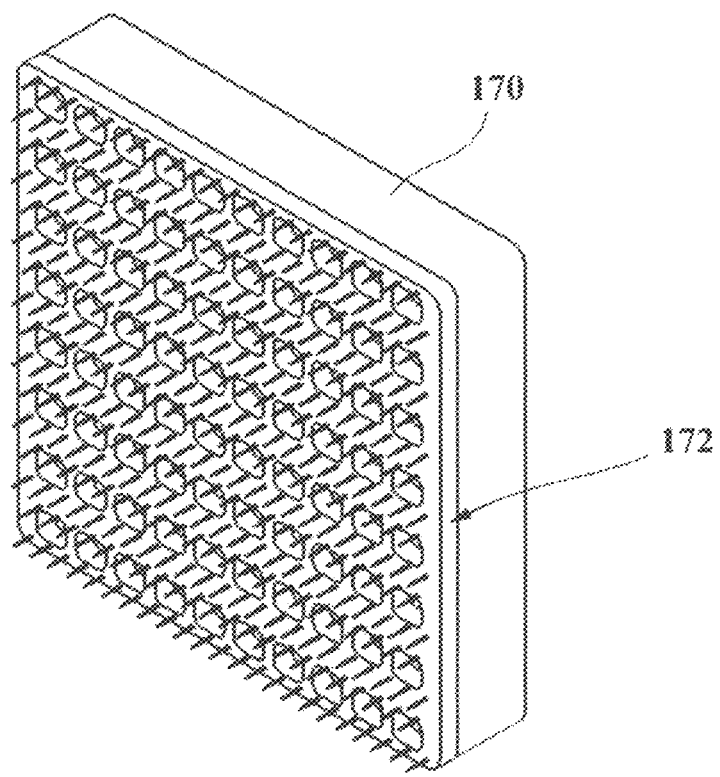
Figure 12C:
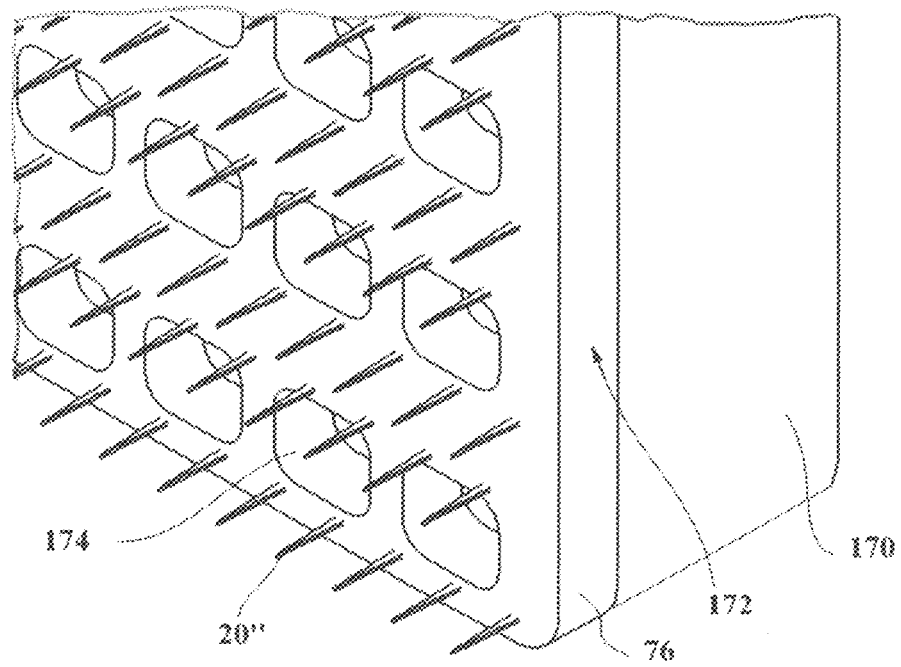

Embodiments of material engagement element devices wherein the devices are used as an adhesive for conventional bandages are disclosed hereafter. FIG. 12A shows a perforated material engagement element pad 172 being applied to conventional bandage material 170 through the use of an adhesive 168 applied to the surface of the conventional bandage material 170. The conventional bandage material may be any of the following: alginate material, collagen material, composite material, contact layer material, foam material, gauze material, binder material, hydrocollodid material, specialty absorptive material, transparent film material, or any other suitable conventional bandage material. FIG. 12B shows the perforated material engagement element pad 172 attached to the conventional bandage 170. FIG. 12C is a close up view of FIG. 12B showing the conventional bandage material 170, the perforated material engagement element pad 172, the material engagement elements in a perpendicular state 20", and holes 174 in the flexible base material 76 which allow for the communication of gasses and liquids between the wound site and the conventional bandage 170. The use of any of the conventional bandage materials 170 as a replacement for the flexible base material 76 could be applied to any material engagement element device embodiment including the cylindrical material engagement element devices (FIGS. 7P and 7Q), the spherical material engagement element device (FIG. 9T), or any other suitable material engagement element device configuration.

What is claimed is:

1. A method for manufacturing a material engagement element pad assembly comprising:
cutting a pattern of material engagement element slots and respective material engagement elements into a shape memory sheet material in a flat state thereby forming a material engagement element sheet;
forming each material engagement element from the flat state into a state which is perpendicular to a surface of the shape memory sheet material;
inserting the material engagement elements into a temporary stabilizing material such that a distal end of each material engagement element is partially deployed into the temporary stabilizing material; and
forming a flexible base material about a proximal end of each material engagement element such that the flexible base material encompasses the proximal end of each material engagement element thereby mechanically fixing each material engagement element into the flexible base material.

2. The method of claim 1 further comprising shape setting an engagement state into each material engagement element prior to forming each material engagement element into the state which is perpendicular to the surface of the shape memory sheet material.

3. The method of claim 2 wherein shape setting an engagement state into each material engagement element comprises sandwiching the material engagement element sheet between a top radius fixture and a bottom radius fixture, applying a force to the top radius fixture thereby conforming each material engagement element to profiles of a respective positive radius boss of the bottom radius fixture and respective radius slot of the top radius fixture, and applying a heat treatment cycle to shape set the material engagement elements into the engagement state.

4. A method for manufacturing a material engagement element pad assembly comprising;
cutting a pattern of material engagement element slots and respective material engagement elements into a sheet material thereby forming a material engagement element sheet wherein the sheet material comprises a composite sheet having two or more layers wherein at least one layer comprises a pre-strained shape memory material;
forming each material engagement element into a state which is perpendicular to a surface of the sheet material;
inserting the material engagement elements into a temporary stabilizing material such that a distal end of each material engagement element is partially deployed into the temporary stabilizing material; and forming a flexible base material about a proximal end of each material engagement element such that the flexible base material encompasses the proximal end of each material engagement element thereby mechanically fixing each material engagement element into the flexible base material.

5. The method of claim 1 wherein forming a flexible base material about a proximal end of each material engagement element further comprises forming the flexible base material about the sheet material.

6. A method for manufacturing a material engagement element pad assembly comprising;
cutting a pattern of material engagement element slots and respective material engagement elements into a sheet material thereby forming a material engagement element sheet;
forming each material engagement element into a state which is perpendicular to a surface of the sheet material wherein forming each material engagement element into the state which is perpendicular to the surface of the sheet material comprises sandwiching the material engagement element sheet between a top perpendicular fixture and a bottom perpendicular fixture, and applying a force to the top perpendicular fixture thereby conforming each material engagement element to surfaces of a respective positive perpendicular boss of the bottom perpendicular fixture and respective perpendicular slot of the top perpendicular fixture such that each material engagement element assumes the state perpendicular to the surface of the sheet material;
inserting the material engagement elements into a temporary stabilizing material such that a distal end of each material engagement element is partially deployed into the temporary stabilizing material; and
forming a flexible base material about a proximal end of each material engagement element such that the flexible base material encompasses the proximal end of each material engagement element thereby mechanically fixing each material engagement element into the flexible base material.

7. The method of claim 1 wherein prior to the step of forming the flexible base material about a proximal end of each material engagement element the method further comprises:
forming the material engagement element sheet and temporary stabilizing material around a cylindrical mandrel.

8. The method of claim 7 further comprising shape setting an engagement state into each material engagement element prior to forming each material engagement element into a state which is perpendicular to the surface of the shape memory sheet material.

9. The method of claim 8 wherein shape setting the engagement state into each material engagement element comprises sandwiching the material engagement element sheet between a top radius fixture and a bottom radius fixture, applying a force to the top radius fixture thereby conforming each material engagement element to profiles of a respective positive radius boss of the bottom radius fixture and respective radius slot of the top radius fixture, and applying a heat treatment cycle to shape set the material engagement elements into the engagement state.

10. The method of claim 7 wherein the shape memory sheet material comprises a composite sheet having two or more layers wherein at least one layer comprises a pre-strained shape memory material.

11. The method of claim 7 further comprising trimming excess sheet material from the material engagement element sheet prior to forming the flexible base material about the proximal end of each material engagement element.

12. The method of claim 7 wherein forming the material engagement element sheet and temporary stabilizing material around the cylindrical mandrel comprises forming the material engagement element sheet and temporary stabilizing material around the cylindrical mandrel such that the distal end of each material engagement element is directed toward a cylindrical mandrel axis.

13. The method of claim 12 further comprising removing the cylindrical material engagement element device from the cylindrical mandrel after forming the flexible base material about the proximal end of each material engagement element by inverting the cylindrical material engagement element device such the distal end of each material engagement element is directed away from the cylindrical mandrel axis upon inversion.

14. The method as defined in claim 1 wherein prior to the step of forming the flexible base material about the proximal end of each material engagement element the method further comprises:
forming the spherical material engagement element sheet and temporary stabilizing material over a surface of a spherical mold.

15. The method of claim 14 further comprising shape setting an engagement state into each material engagement element prior to forming each material engagement element into a state which is perpendicular to the surface of the shape memory sheet material.

16. The method of claim 15 wherein shape setting the engagement state into each material engagement element comprises sandwiching the spherical material engagement element sheet between a spherical top radius fixture and a spherical bottom radius fixture, applying a force to the spherical top radius fixture thereby conforming each material engagement element to profiles of a respective spherical positive radius boss of the spherical bottom radius fixture and respective spherical radius slot of the spherical top radius fixture, and applying a heat treatment cycle to shape set the material engagement elements into the engagement state.

17. The method of claim 14 wherein the shape memory sheet material comprises a composite sheet having two or more layers wherein at least one layer comprises a pre-strained shape memory material.

18. The method of claim 14 further comprising trimming excess sheet material from the spherical material engagement element sheet prior to forming the flexible base material about the proximal end of each material engagement element.

19. The method of claim 14 wherein forming the spherical material engagement element sheet and temporary stabilizing material around the spherical mold comprises forming the spherical material engagement element sheet and temporary stabilizing material around the spherical mold such that the distal end of each material engagement element is directed toward a center of the spherical material engagement element device.

20. The method of claim 19 further comprising removing the spherical material engagement element device from the spherical mold after forming the flexible base material about the proximal end of each material engagement element by inverting the spherical material engagement element device such the distal end of each material engagement element is directed away from the center of the spherical material engagement element device upon inversion.

\* \* \* \* \*